US010617609B2

(12) United States Patent
Shimizu et al.

(10) Patent No.: US 10,617,609 B2
(45) Date of Patent: Apr. 14, 2020

(54) COMPOSITION COMPRISING MICROCAPSULES CONTAINING REFLECTIVE PARTICLES

(71) Applicant: L'OREAL, Paris (FR)

(72) Inventors: Momoko Shimizu, Tokyo (JP); Qing Yu, Shanghai (CN)

(73) Assignee: L'OREAL, Paris (FR)

(*) Notice: Subject to any disclaimer, the term of this patent is extended or adjusted under 35 U.S.C. 154(b) by 81 days.

(21) Appl. No.: 15/306,931

(22) PCT Filed: Apr. 30, 2015

(86) PCT No.: PCT/IB2015/053165
§ 371 (c)(1),
(2) Date: Oct. 26, 2016

(87) PCT Pub. No.: WO2015/166454
PCT Pub. Date: Nov. 5, 2015

(65) Prior Publication Data

US 2017/0042774 A1 Feb. 16, 2017

(30) Foreign Application Priority Data

Apr. 30, 2014 (EP) .................................... 14305643

(51) Int. Cl.

| | |
|---|---|
| ***A61K 8/02*** | (2006.01) |
| ***A61K 8/73*** | (2006.01) |
| ***A61K 8/81*** | (2006.01) |
| ***A61K 8/34*** | (2006.01) |
| ***A61Q 1/02*** | (2006.01) |
| ***A61Q 19/00*** | (2006.01) |
| ***A61K 8/04*** | (2006.01) |
| ***A61K 8/06*** | (2006.01) |
| ***A61K 8/29*** | (2006.01) |

(52) U.S. Cl.
CPC ............ *A61K 8/0254* (2013.01); *A61K 8/042* (2013.01); *A61K 8/046* (2013.01); *A61K 8/062* (2013.01); *A61K 8/29* (2013.01); *A61K 8/345* (2013.01); *A61K 8/732* (2013.01); *A61K 8/8129* (2013.01); *A61K 8/8147* (2013.01); *A61Q 1/02* (2013.01); *A61Q 19/00* (2013.01); *A61K 2800/26* (2013.01); *A61K 2800/262* (2013.01); *A61K 2800/412* (2013.01); *A61K 2800/43* (2013.01); *A61K 2800/621* (2013.01); *A61K 2800/624* (2013.01); *A61K 2800/63* (2013.01); *A61K 2800/652* (2013.01)

(58) Field of Classification Search
CPC .................................................... A61K 8/0254
See application file for complete search history.

(56) References Cited

U.S. PATENT DOCUMENTS

| | | | |
|---|---|---|---|
| 5,236,986 A | 4/1993 | Sakuta | |
| 5,246,694 A | 9/1993 | Birthwistle et al. | |
| 5,412,004 A | 5/1995 | Tachibana et al. | |
| 5,538,793 A | 7/1996 | Inokuchi et al. | |
| 5,811,487 A | 9/1998 | Schulz et al. | |
| 5,837,793 A | 11/1998 | Harashima et al. | |
| 5,874,069 A | 2/1999 | Mendolia et al. | |
| 5,919,441 A | 7/1999 | Mendolia et al. | |
| 5,981,680 A | 11/1999 | Petroff et al. | |
| 6,051,216 A | 4/2000 | Barr et al. | |
| 6,280,748 B1 | 8/2001 | Morita et al. | |
| 6,299,979 B1 | 10/2001 | Neubauer et al. | |
| 6,387,498 B1 | 5/2002 | Coulter et al. | |
| 6,491,927 B1 | 12/2002 | Arnaud et al. | |
| 6,932,984 B1 | 8/2005 | Babtsov et al. | |
| 7,981,404 B2 * | 7/2011 | Dumousseaux ......... | A61K 8/11 424/63 |
| 2003/0031870 A1 | 2/2003 | Argoitia et al. | |
| 2004/0123779 A1 * | 7/2004 | Bagala, Sr. ........... | C09C 1/0024 106/415 |
| 2004/0156806 A1 | 8/2004 | Patil et al. | |
| 2004/0175338 A1 | 9/2004 | Filippi et al. | |
| 2004/0180011 A1 | 9/2004 | Schlosser | |

(Continued)

FOREIGN PATENT DOCUMENTS

| | | |
|---|---|---|
| EP | 0 242 219 A2 | 10/1987 |
| EP | 0 295 886 A2 | 12/1988 |

(Continued)

OTHER PUBLICATIONS

BASF: Cloisonne, Technical Information, 12 pages (Year: 2016).*
U.S. Appl. No. 14/372,862, filed Jul. 17, 2014, US 2014-0356402 A1, Cyril Lemoine, et al.
U.S. Appl. No. 14/372,872, filed Jul. 17, 2014, US 2014-0356403 A1, Rong Zhu, et al.
U.S. Appl. No. 14/372,888, filed Jul. 17, 2014, US 2014-0341987 A1, Yihao Chai, et al.
U.S. Appl. No. 14/772,929, filed Sep. 4, 2015, US 2016-0015610 A1, Audrey Ricard, et al.
U.S. Appl. No. 14/772,989, filed Sep. 4, 2015, US 2016-0015611 A1, Audrey Ricard, et al.

(Continued)

*Primary Examiner* — Kyle A Purdy
(74) *Attorney, Agent, or Firm* — Oblon, McClelland, Maier & Neustadt, L.L.P.

(57) ABSTRACT

The instant invention relates to a composition for caring for and/or making up keratin materials comprising, in a physiologically acceptable medium, at least one microcapsule containing at least one encapsulated releasable material(s) said microcapsule comprising at least one core and at least one layered coating surrounding said core, and said encapsulated material(s) being at least one reflective particle, and being only released from said microcapsule(s) when said composition is applied onto a keratin material, such as keratin fibers or skin. The invention further relates to a cosmetic process for caring for and/or making up keratinic materials, comprising application on said keratinic materials in particular on the skin of a composition as defined above.

22 Claims, 1 Drawing Sheet

(56) References Cited

U.S. PATENT DOCUMENTS

| | | | | |
|---|---|---|---|---|
| 2005/0220728 | A1 | 10/2005 | Kanji et al. | |
| 2006/0051425 | A1 | 3/2006 | Kvitnitsky et al. | |
| 2006/0225609 | A1 | 10/2006 | Rueger et al. | |
| 2009/0035365 | A1 | 2/2009 | Popplewell et al. | |
| 2010/0168251 | A1 | 7/2010 | Warr et al. | |
| 2010/0175587 | A1 | 7/2010 | Rueger et al. | |
| 2014/0335138 | A1 | 11/2014 | Goldstein et al. | |
| 2014/0341987 | A1 | 11/2014 | Chai et al. | |
| 2014/0356402 | A1 | 12/2014 | Lemoine et al. | |
| 2016/0015611 | A1* | 1/2016 | Ricard | A61Q 19/00 424/401 |

FOREIGN PATENT DOCUMENTS

| | | | | |
|---|---|---|---|---|
| EP | 0 765 656 | A1 | 4/1997 | |
| EP | 0 903 342 | A1 | 3/1999 | |
| EP | 2 204 155 | A1 | 7/2010 | |
| EP | 2277982 | A1 * | 1/2011 | A61K 8/11 |
| FR | 2 466 492 | A1 | 4/1981 | |
| FR | 2 841 155 | A1 | 12/2003 | |
| JP | 61-194009 | A | 8/1986 | |
| JP | 2-243612 | A | 9/1990 | |
| JP | 5-17710 | A | 1/1993 | |
| JP | 7-258460 | A | 10/1995 | |
| JP | 9-188830 | A | 7/1997 | |
| JP | 10-158450 | A | 6/1998 | |
| JP | 10-158541 | A | 6/1998 | |
| JP | 2001-11340 | A | 1/2001 | |
| JP | 2011-79804 | A | 4/2011 | |
| JP | 2012-530692 | A | 12/2012 | |
| WO | WO 97/25970 | A1 | 7/1997 | |
| WO | WO 97/35842 | A1 | 10/1997 | |
| WO | WO 99/36477 | A1 | 7/1999 | |
| WO | WO 01/35933 | A2 | 5/2001 | |
| WO | WO 02/051828 | A2 | 7/2002 | |
| WO | WO 2005/090444 | A1 | 9/2005 | |
| WO | WO 2008/139053 | A1 | 11/2008 | |
| WO | WO 2009/138978 | A2 | 11/2009 | |
| WO | WO2011/027960 | A2 | 3/2011 | |
| WO | WO 2012/156965 | A2 | 11/2012 | |
| WO | WO 2013/107350 | A1 | 7/2013 | |
| WO | WO 2013/107351 | A1 | 7/2013 | |
| WO | WO 2013/107352 | A1 | 7/2013 | |
| WO | WO 2013/107354 | A1 | 7/2013 | |

OTHER PUBLICATIONS

U.S. Appl. No. 15/306,944, filed Oct. 26, 2016, Momoko Shimizu, et al.

International Search Report and Written Opinion dated Jul. 14, 2015 in PCT/IB2015/053165.

European Search Report dated Oct. 29, 2014 in Patent Application No. EP 14 30 5643.

* cited by examiner

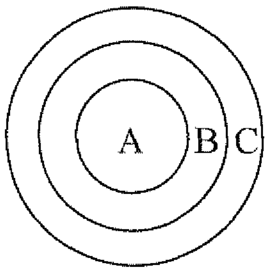
A
B
C

COMPOSITION COMPRISING MICROCAPSULES CONTAINING REFLECTIVE PARTICLES

FIELD OF THE INVENTION

The present invention relates to a composition in particular useful for care, hygiene and/or makeup of keratin materials comprising microcapsules containing at least one reflective particle, in particular in the form of flakes, and more particularly having a ratio d/e greater than 10.

BACKGROUND OF THE INVENTION

There is a growing interest in imparting care properties in cosmetic products especially in make-up compositions. These care properties are often associated with a smooth, creamy, rich appearance of the compositions. Such creamy compositions are also supposed to impart benefits like nourishing properties to the treated keratinous material, especially the skin.

Nevertheless, the introduction of some ingredients in cosmetic compositions may be detrimental towards the general appearance and comfort of use of the composition, in particular for skin-care products for which it is generally sought some codes which are an aesthetical purity of the composition associated with a good sensoriality, texture when the composition is picked up and applied onto the skin.

In particular, the introduction of some ingredients in cosmetic compositions may be detrimental towards the homogeneity of the composition with respect to the presence of such ingredients which may then be inhomogeneously dispersed typically when they are in the form of particles. And even the introduction of some ingredients may sometimes induce additional problems attached to this dispersion problem, such as the thickening of the composition, modification of the composition appearance when the ingredients are colored or exhibit iridescence. As far as such additional optical effects, for example in connection to the presence of reflective particles, are not necessary desired, there exists a need to reduce such drawbacks.

As representative of this kind of ingredient may in particular be reflective particles.

Moreover, some of them absorb a significant part of the composition in which they are introduced, this absorption leading to a thickening of the composition which may be undesirable.

Reflective particles are furthermore mainly used for their visual properties, particularly for the sparkle, glitter, or pearly effect they can confer to the composition and also to the users when applied.

Nevertheless a major technical problem with reflective particles is to obtain a homogeneous composition that is a composition wherein the reflective particles are uniformly distributed.

Indeed the reflective particles tend to migrate at the composition interfaces during the storage, namely at the surface and against the inside of the container wall.

This phenomenon may sometimes be desired, but homogenous compositions are generally preferred.

Accordingly, there is a need for compositions containing such reflective particles but wherein the reflective particles are homogenously distributed.

Surprisingly and advantageously, the compositions according to the invention meet these needs. Moreover, the inventors have stated that the compositions according to the invention act favorably with respect to desired optical effects on the skin, namely radiance and evenness.

SUMMARY OF INVENTION

Thus, according to one of its aspects, the invention is directed to a composition for caring for and/or making up keratin materials comprising, in a physiologically acceptable medium, at least one microcapsule containing at least one reflective particle said microcapsule comprising at least one core and at least one layered coating surrounding said core, and said reflective particle being only released from said microcapsule(s) when said composition is applied onto a keratin material, such as keratin fibers or skin.

The microcapsules according to the invention are particularly interesting for the following reasons.

The encapsulated reflective particles are kept in the microcapsules during the storage of the composition and only released upon application of said composition on the keratin material.

By this way, the microcapsules according to the invention are able to permanently retain the reflective particles in the microcapsule during storage of the composition, and thus efficiently prevent any undesirable modification of the stability of the composition and to keep a same long-term visual effect to said composition.

Particularly, the reflective particles either appear to be uniformly distributed in the composition or are not visible in the bulk. But in both cases, the composition is visually homogeneous.

By using said microcapsules, it is possible to achieve cosmetic compositions containing greater amount of reflective particle(s).

By this way, the microcapsules according to the invention allow to overcome incompatibility issues due to the use of reflective particle(s) with other ingredient(s) of the composition.

The microcapsules according to the invention are also advantageously stable with a large panel of solvent/ingredient associated.

They are also stable in the compositions according to the present invention, preferably at high temperatures, for instance greater than or equal to 40° C., for example for one month, better two months and still better three months in an oven at 45° C. or for 15 days in an oven at 60° C.

In a preferred embodiment, the microcapsules according to the present invention present appropriate softening kinetics.

That is preferably, at least three hours after being in contact with the other compounds of the formula, the hardness of the microcapsules is advantageously from 5 to 50 grams, more preferably from 6 to 20 grams and still more preferably from 7 to 10 grams. Such hardness is in conformity with an industrial process for preparing the cosmetic compositions including such microcapsules.

Such values of softening kinetics and hardness allow to provide not only aesthetic microcapsules but also overall aesthetic compositions.

Further some reflective particles, particularly nacres, may also lead to changing color compositions. Namely the encapsulated reflective particles may confer a color to the composition which is different from the color obtained after application of the composition, i.e., after the microcapsules containing reflective particles have been broken.

Advantageously, they have the ability of swelling or softening in contact of a liquid medium such as water and optionally at least one compound chosen from polyols, glycols and $C_2$-$C_8$ monoalcohols, and mixtures thereof, or alternatively in a liquid fatty phase (preferably an oily phase). By this way, they are advantageously deformable when applied on a keratin material and consequently provide a soft feeling to the user.

Furthermore, their size contributes to not create any discomfort or unfavorable, grainy feeling when applied. In particular, they are soft enough to rupture upon very slight rubbing or pressing on the skin in order to release their content.

They disintegrate rapidly immediately when applied, with a liquid feeling on the skin and leading to compositions devoid of any granular aspect.

However, they are durable enough to avoid destruction of the coating during manufacture, even during an industrial process, and storage of corresponding composition. Thus, they exhibit hardness sufficient to be compounded in an industrial process without alteration. Advantageously the hardness of the microcapsules does not significantly decrease during the preparation process. Thus, they allow the use of regular equipment for the preparation of the compositions of the invention.

Accordingly, the microcapsules of the present invention are particularly interesting since they increase the stability of the reflective particle against degradation, and prevent undesirable release of the encapsulated actives into the composition during the manufacturing process and prolonged storage.

The present invention further describes a process of preparing the microcapsules. The process includes:

- preparing an aqueous solution containing water, a first hydrophilic polymer,
- dispersing reflective particles in the aqueous solution;
- forming an inner layer on a core with the aqueous solution in which the reflective particles are dispersed;
- forming an intermediate layer on the inner layer with an intermediate layer solution containing water, a second hydrophilic polymer, and a pigment; and
- forming an outer layer on the intermediate layer with an outer layer solution containing water and a third hydrophilic polymer, provided that the aqueous solution advantageously does not include any hydrophobic solvent The present invention further describes the microcapsule obtained by this process.

A further object of the invention is composition for caring for and/or making up keratin materials comprising, in a physiologically acceptable medium, at least one microcapsule containing at least one reflective particle said microcapsule comprising at least one core and at least one layered coating surrounding said core, and said reflective particle, being only released from said microcapsule(s) when said composition is applied onto a keratin material, such as keratin fibers or skin, said microcapsule being obtained by a process comprising the following steps, in this order:

preparing an aqueous solution containing water, a first hydrophilic polymer, dispersing reflective particles in the aqueous solution;

forming an inner layer on a core with the aqueous solution in which the reflective particles are dispersed;

forming an intermediate layer on the inner layer with an intermediate layer solution containing water, a second hydrophilic polymer, and a pigment; and forming an outer layer on the intermediate layer with an outer layer solution containing water and a third hydrophilic polymer, provided that the aqueous solution advantageously does not include any hydrophobic solvent, the first, second, and third hydrophilic polymers being the same or different.

BRIEF DESCRIPTION OF THE DRAWINGS

FIG. 1 is a schematic diagram illustrating a typical structure of a microcapsule of the present invention wherein A represents a core and B, and C, being different layers concentrically surrounding said core.

FIG. 1 typically represents the microcapsule of example 12 wherein A represents the core comprising lecithin, mannitol, a corn starch binder and reflective particle(s), B represents the inner layer comprising lecithin, mannitol, a corn starch binder and reflective particle(s) and C represents the outer layer comprising lecithin and a corn starch binder.

DETAILED DESCRIPTION OF THE INVENTION

A composition according to one embodiment of the invention may comprise from 0.1% to 20% by weight and preferably from 0.5% to 15% by weight of microcapsules relative to the total weight of the said composition.

In particular for a skin care composition according to the invention, the amount of microcapsules will range from 0.1% to 5%, preferably from 0.2% to 3% by weight relative to the total weight of composition.

In particular for a make-up composition according to the invention, the amount of microcapsules will range from 0.5% to 30%, preferably from 1% to 15%, more preferably from 2% to 10% by weight relative to the total weight of composition.

Advantageously, in certain aspects the ratio between the microparticle volume and the composition volume ranges from 10 to 95.

Advantageously, a composition of the invention may comprise two or more microcapsules of the invention different from each other.

According to a first embodiment, the encapsulated reflective particle(s) is/are present in the core of the microcapsules. Particularly, the encapsulated reflective particle(s) is/are only present in the core of the microcapsules.

In on specific sub-embodiment, the core of said microparticles includes at least one or several reflective particles and at least one binder.

In another specific sub-embodiment, the reflective particle(s) is/are present in the core as a lipidic or aqueous dispersion.

According to a second embodiment, at least one inner layer surrounding the core includes the reflective particle(s).

Inner layer means that this layer is obligatory surrounded by another inner or outer layer. Further the layered coating advantageously comprises at least one inner layer and one outer layer.

Particularly, the encapsulated reflective particle(s) is/are only present in at least one inner layer of the microcapsules.

The term "encapsulated" means that the reflective particle is always entrapped inside the microcapsules according to the invention.

In other words, the outer layer of the microcapsules encapsulating the reflective particle is always free from any reflective particle. Advantageously, the outer layer is free from reflective particle(s) and preferably comprises at least one hydrophilic polymer and optionally a binder. Such a binder, i.e. a hydrophilic polymer, may be selected from hydrophilic polymer such as starch, cationic starch, cellulose, modified cellulose, Mannitol, sucrose, polyvinyl alcohol and carrageenan.

According to a third embodiment, the encapsulated reflective particle is present in the core of the microcapsules and in at least on inner layer.

Chemical Nature of Microcapsules

According to a preferred embodiment, the core is an organic core.

The core of the microparticles may consist in at least one or several reflective particles. If the core is not totally made of reflective particles, it comprises additional organic material(s).

Advantageously the core represents from 1% to 50% by weight, preferably 5 to 30% by weight, and in particular from 10 to 20% by weight relative to the total weight of the microcapsule.

Preferably the microcapsules have a double layer surrounded the core.

Preferably, the microcapsules contain at least one organic layer, preferably one inner organic layer.

According to a preferred embodiment, the microcapsules contain at least one layer, preferably at least one inner layer, comprising at least one binder.

According to another embodiment the outer layer comprises a binder.

Advantageously, the microcapsules have a size of from 50 μm to 800 μm, in particular from 60 μm to 600 μm, and in particular from 80 μm to 500 μm, and in particular from 100 μm to 400 μm.

Preferably the microcapsule comprises at least 5%, preferably at least 10%, more preferably at least 30%, better at least 40%, even better at least 50%, advantageously at least 60% and in particular between 30 and 80% preferably between 40 and 75% by weight of reflective particle(s) relative to the weight of the microcapsule.

According to a preferred embodiment, the microcapsules comprise:

- a core comprising at least one reflective particle and optionally at least one additional organic material,
- at least one layered coating surrounding said core, the layered coating comprising a binder selected from at least one polymer, at least one lipid-based material, and their mixture, preferably their mixture and optionally at least one reflective particle,
- an outer layer comprising a hydrophilic polymer.

According to another preferred embodiment, the microcapsules comprise

- a core comprising at least one organic material,
- at least one layered coating surrounding said core, the layered coating comprising a binder selected from at least one polymer, at least one lipid-based material, and their mixture, preferably their mixture and at least one reflective particle,
- an outer layer comprising a hydrophilic polymer.

Preferably, the core comprises at least one monosaccharide or its derivatives as said organic material, in particular a monosaccharide-polyol advantageously selected from mannitol, erythritol, xylitol, sorbitol and mixtures thereof, preferably mannitol.

Preferably, the layered coating surrounding said core comprises at least one hydrophilic polymer(s) selected from the group consisting of:

- acrylic or methacrylic acid homopolymers or copolymers or salts and esters thereof;
- copolymers of acrylic acid and of acrylamide and its salts and esters thereof;
- polyhydroxycarboxylic acids and its salts and esters thereof;
- polyacrylic acid/alkyl acrylate copolymers, preferably modified or unmodified carboxyvinyl polymers;
- AMPS;
- AMPS/acrylamide copolymers;
- polyoxyethylenated AMPS/alkyl methacrylate copolymers;
- anionic, cationic, amphoteric or nonionic chitin or chitosan polymers;
- cellulose polymers and derivatives;
- Starch polymers and derivatives, eventually modified;
- vinyl polymers and derivatives;
- polymers of natural origins and derivatives thereof;
- alginates and carrageenans;
- glycoaminoglycans, hyaluronic acid and derivatives thereof;
- mucopolysaccharides such as hyaluronic acid and chondroitin sulfates; and the mixtures thereof.

Advantageously the layered coating comprises at least hydrophilic polymer(s) selected from the group consisting of polysaccharides and derivatives, acrylic or methacrylic acid homopolymers or copolymers or salts and esters thereof, and their mixture; the polysaccharides and derivatives are preferably selected from chitosan polymers, chitin polymers, cellulose polymers, starch polymers, galactomannans, alginates, carrageenans, mucopolysaccharides, and their derivatives, and the mixture thereof, more preferably starch polymers and derivatives, cellulose polymers and derivatives, and their mixture.

Particularly the hydrophilic polymer(s) is selected from the polysaccharides and derivatives including one type of ose or several types of ose(s), preferably several types of ose(s) including at least D-glucose units.

Particularly the hydrophilic polymer is selected from starch or derivatives, celluloses or derivatives, preferably starch or derivatives.

Preferably, the core comprises at least one monosaccharide polyol, preferably selected from mannitol, erythritol, xylitol, sorbitol, and the layered coating comprises at least one polysaccharides (or its derivatives) including as oses at least D-Glucose unit(s), preferably selected from starch or derivatives, celluloses or derivatives, preferably starch or derivatives.

Preferably the outer layer of microcapsule is free from reflective particle and preferably comprises at least one hydrophilic polymer and optionally a binder.

Preferably the outer layer comprising at least one hydrophilic polymer defined in the above list. Preferably this hydrophilic polymer is at least one wall-forming polymer preferably selected from polysaccharides such as cellulose derivatives, in particular cellulose ether and cellulose ester, from (poly)(alkyl)(meth)acrylic acid and derivatives, notably (poly)(alkyl)(meth)acrylate and derivatives, and preferably from alkylacrylic/alkylmethacrylic acid copolymers and their derivatives.

Preferably, the microcapsules include at least one lipid based material, preferably with amphiphilic properties such as lecithins and in particular hydrogenated lecithin.

According to another of its aspects, the present invention is also directed to a cosmetic process comprising at least the steps consisting in applying at least part of a composition according to the invention on the surface of a keratin material, in particular the skin.

The term "physiologically acceptable medium" is intended to denote a medium that is particularly suitable for applying a product of the invention to keratin materials, especially the skin and more particularly facial skin.

The "physiologically acceptable medium" according to the present invention comprises the aqueous phase and or a liquid fatty phase.

For the purposes of the present invention, the term "keratin material" is intended to cover the skin, mucous membranes such as the lips, the nails and the eyelashes. The skin and the lips, in particular facial skin, are most particularly considered according to the invention.

Detailed Specification

I—Microcapsules

The term "microcapsule", as used herein, refers to a spherical microcapsule containing at least one layered coating and surrounding a core chemically different from the coating. Microcapsules are distinct from microspheres, which consist of spherical homogeneous matrix.

According to an embodiment, the "at least one layered coating" is a multi-layered coating preferably an organic multi-layered coating.

The term "multi-layer microcapsule" refers to a microcapsule consisting of a core surrounded by a coating based on one or more inner layer(s) and one outer layer. The one or more inner layer(s) forming the multi-layer coating of the multi-layer microcapsule and the single outer layer of the microcapsule may be formed of the same or different wall-forming organic compound(s).

The microcapsule according to the invention comprises a core also called "inner core" surrounded by a coating based on one or more layer(s). In a preferred embodiment, the microcapsule is a 'multi-layers' microcapsule, comprising at least one inner layer and one outer layer. The one or more inner layer(s) forming the multi-layer coating of the multi-layer microcapsule and the single outer layer of the microcapsule may be formed of the same or different wall-forming organic compound(s).

In a particular embodiment the inner layer and the outer layer are formed of the same wall forming organic compounds, the core is then surrounded by a one layer coating.

The term "wall-forming organic compound" refers to an organic compound or a combination of two or more different organic compounds as defined herein, which form a component of the layer(s) of the microcapsules. In a preferred embodiment, the 'wall-forming organic compound' comprises at least one polymer.

Generally, average particle sizes of up to about 800 μm in diameter of microcapsules are used according to the invention. Preferably the average particle size is less than about 400 μm in diameter of the microcapsules for skin care applications. Advantageously the average particle size is in the range of about 10 μm to 350 μm in diameter. Preferably, the average particle size will be from 50 μm to 800 μm, in particular from 60 μm to 600 μm, and in particular from 80 μm to 500 μm, and in particular from 100 μm to 400 μm in diameter.

In particular, the average particle size may be from 50 to 1,000 Mesh (around 400 μm to 10 μm), in particular from 60 to 200 Mesh (around 250 μm to 75 μm) as measured by the sieving test method or observed by microscope.

Ia) Core

The core is made of reflective particle and/or of at least an organic material. The size of said core preferably ranges from 500 nm to 150 μm in diameter.

Preferably the core is in a solid and/or crystal form at room temperature.

In a particular embodiment, the organic material is selected from organic materials having high water dissolvability. Preferably, the core is water-soluble or water-dispersible.

In a particular embodiment, the core is based on only one compound, preferably one organic compound.

This compound may be one reflective particle.

This compound may be a natural compound.

According to a preferred embodiment, the core is sugar-alcohol, preferably a monosaccharide-polyol advantageously selected from mannitol, erythritol, xylitol and sorbitol.

In a particular embodiment, the core is made of mannitol and more preferably exclusively made of mannitol.

According to an alternative embodiment, the core contains at least mannitol and at least one additional ingredient being preferably a polymer selected from hydrophilic polymers.

In particular, such a core may comprise mannitol and hydrophilic polymers chosen among cellulose polymers, starch polymers and their mixture, preferably their mixture.

In a preferred embodiment, the cellulose polymer is a carboxymethylcellulose and the starch polymer is a non-modified natural starch, for example corn starch.

The core may be constituted by a seed (or crystal) of one of the previous materials.

The core is preferably contained in an amount of from 1% to 50% by weight, preferably 4 to 40% by weight, in particular 5 to 30% by weight, and in particular from 10 to 20% by weight with respect to the total weight of the microcapsule.

The mannitol is preferably contained in an amount of from 2% to 100% by weight, preferably 5 to 100% by weight, and in particular 100% by weight with respect to the total weight of the core.

The mannitol is preferably contained in an amount of from 1% to 50% by weight, preferably 4% to 40% by weight, in particular 5% to 30% by weight, and in particular from 10% to 20% by weight with respect to the total weight of the microcapsule.

I b) External Layer(s) or Coating

As disclosed previously, the core is advantageously surrounded with a coating, or external layer(s) preferably comprising at least one inner layer and one outer layer. In this latter case, these layers preferably extend concentrically in respect with the core.

The layer(s) is/are preferably organic, i.e. contain(s) at least one organic compound as wall-forming material. Preferably, the inner and/or outer layer(s) include(s) at least one polymer, and in particular a hydrophilic polymer.

Polymer(s)

The composition according to the invention comprises one or more polymer(s). In a particular embodiment, the polymer(s) is/are hydrophilic polymer(s).

Such hydrophilic polymer(s) is/are soluble or dispersible in water or in alcohol compounds, in particular chosen from lower alcohols, glycols, polyols.

For the purposes of the present patent application, the term "hydrophilic polymer" means a (co)polymer that is capable of forming hydrogen bond(s) with water or alcohol compounds, in particular chosen from lower alcohols, glycols, polyols. In particular, polymers are concerned which are capable of forming O—H, N—H and S—H bonds.

According to a particular embodiment of the invention, the hydrophilic polymer may swell or soften in contact with water or alcohol compounds, in particular chosen from lower alcohols, glycols, polyols.

The hydrophilic polymer(s) may be chosen from the following polymer(s):

- acrylic or methacrylic acid homopolymers or copolymers or salts and esters thereof and in particular the products sold under the names Versicol F or Versicol K by the company Allied Colloid, Ultrahold 8 by the company Ciba-Geigy, and polyacrylic acids of Synthalen K type, and salts, especially sodium salts, of polyacrylic acids (corresponding to the INCI name sodium acrylate copolymer) and more particularly a crosslinked sodium polyacrylate (corresponding to the INCI name sodium acrylate copolymer (and) caprylic/capric triglycerides) sold under the name Luvigel EM by the company;
- copolymers of acrylic acid and of acrylamide sold in the form of the sodium salt thereof under the names Reten by the company Hercules, the sodium polymethacrylate sold under the name Darvan No. 7 by the company Vanderbilt, and the sodium salts of polyhydroxycarboxylic acids sold under the name Hydagen F by the company Henkel;
- polyacrylic acid/alkyl acrylate copolymers, preferably modified or unmodified carboxyvinyl polymers; the copolymers most particularly preferred according to the present invention are acrylate/$C_{10}$-$C_{30}$-alkylacrylate copolymers (INCI name: Acrylates/$C_{10-30}$ Alkyl acrylate Crosspolymer) such as the products sold by the company Lubrizol under the trade names Pemulen TR1, Pemulen TR2, Carbopol 1382 and Carbopol ETD 2020, and even more preferentially Pemulen TR-2;
- alkylacrylic/alkylmethacrylic acid copolymers and their derivatives notably their salts and their esters, such as the copolymer of ethyl acrylate, methyl methacrylate and low content of methacrylic acid ester with quaternary ammonium groups provided under the tradename of EUDRAGIT RSPO from Evonik Degussa;
- AMPS (polyacrylamidomethylpropanesulfonic acid partially neutralized with aqueous ammonia and highly crosslinked) sold by the company Clariant;
- AMPS/acrylamide copolymers such as the products Sepigel or Simulgel sold by the company SEPPIC, especially a copolymer of INCI name Polyacrylamide (and) C13-14 Isoparaffin (and) Laureth-7;
- polyoxyethylenated AMPS/alkyl methacrylate copolymers (crosslinked or non-crosslinked) of the type such as Aristoflex HMS sold by the company Clariant;
- polysaccharides and derivatives, such as:
  - anionic, cationic, amphoteric or nonionic chitin or chitosan polymers;
  - cellulose polymers and derivatives, preferably other than alkylcellulose, chosen from hydroxyethylcellulose, hydroxypropylcellulose, hydroxypropylmethylcellulose, hydroxymethylcellulose, ethylhydroxyethylcellulose and carboxymethylcellulose, and also quaternized cellulose derivatives; in a preferred embodiment, the cellulose polymers is a carboxymethylcellulose;
  - starch polymers and derivatives, eventually modified; in a preferred embodiment, the starch polymer is a natural starch;
  - optionally modified polymers of natural origin, such as galactomannans and derivatives thereof, such as konjac gum, gellan gum, locust bean gum, fenugreek gum, karaya gum, gum tragacanth, gum arabic, acacia gum, guar gum, hydroxypropyl guar, hydroxypropyl guar modified with sodium methylcarboxylate groups (Jaguar XC97-1, Rhodia), hydroxypropyltrimethylammonium guar chloride, and xanthan derivatives;
  - alginates and carrageenans;
  - glycoaminoglycans, hyaluronic acid and derivatives thereof,
  - mucopolysaccharides such as hyaluronic acid and chondroitin sulfates, and mixtures thereof;
- vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;
- and the mixtures thereof.

Preferably, the composition according to the invention, and in particular the external layer(s) comprise(s) hydrophilic polymers selected from the group consisting of polysaccharides and derivatives, acrylic or methacrylic acid homopolymers or copolymers or salts and esters thereof, and their mixture.

The said polymer(s) is (are) advantageously selected from (poly)(alkyl)(meth)acrylic acid and derivatives, notably (poly)(alkyl)(meth)acrylate and derivatives, preferably from alkylacrylic/alkylmethacrylic acid copolymers and their derivatives, and most preferably is a copolymer of ethyl acrylate, methyl methacrylate and low content of methacrylic acid ester with quaternary ammonium groups provided under the tradename of EUDRAGIT RSPO from Evonik Degussa.

Said polysaccharides and derivatives are preferably selected from chitosan polymers, chitin polymers, cellulose polymers, starch polymers, galactomannans, alginates, carrageenans, mucopolysaccharides, and their derivatives, and the mixture thereof.

In a preferred embodiment, the external layer(s) is/are devoid of microcrystalline cellulose.

According to one particularly preferred embodiment, said polysaccharides and their derivatives are preferably selected from the ones including one type of ose or several types of ose(s), preferably several types of oses, in particular at least D-Glucose unit(s) as ose(s), preferably starch polymers, cellulose polymers, and derivatives, and the mixture thereof.

According to a preferred embodiment, the microcapsule contains at least one hydrophilic polymer selected from the group consisting of starch and its derivatives, in particular corn starch, cellulose and its derivatives, homo- and/or co-polymer of methacrylic acid and/or methacrylic acid ester or co-polymer of (alkyl)acrylic acid and/or (alkyl) methacrylic acid and their derivatives, preferably their salts and their ester, and in particular the capsule contains polymethyl methacrylate.

Starch usable according to the present invention is usually issued from vegetable raw materials, such as rice, soybeans, potatoes, or corn. Starch can be unmodified or (by analogy with cellulose) modified starch. In a preferred embodiment, the starch is unmodified.

Preferred homo- and/or co-polymer of methacrylic acid and/or methacrylic acid ester are those wherein the copolymer of methyl methacrylate and ethyl acrylate has a molecular weight from 750 to 850 kDa.

Cellulose derivatives include, for example, alkali celluloses carboxymethyl cellulose (CMC), cellulose esters and ethers, and aminocelluloses. In a particular embodiment, the cellulose is a carboxymethyl cellulose (CMC).

According to a preferred embodiment, the capsule contains at least starch derivative, in particular corn starch, polymethyl methacrylate, co-polymer of (alkyl)acrylic acid and/or (alkyl)methacrylic acid and their derivatives preferably their salts and their ester, and/or cellulose derivative.

Preferably, the microcapsule contains polymer(s) which are not cross-linked.

The polymer(s) may be in one or several layer(s).

In another embodiment, the polymer(s) may be in the core.

The microcapsule may contain polymer(s) in the core and/or in the layer(s).

In a particular embodiment, the polymer(s) is (are) in the core and in the layer(s).

In an embodiment, the core contains at least starch and/or cellulose derivative as polymer(s). When the starch is contained within the core, it represents the main ingredient of such a core, i.e. the weight amount of starch is greater than the respective amount of other compounds of the core.

The polymer may represent from 0.5 to 20% by weight of the microcapsule, in particular from 1 to 10% by weight, preferably from 2 to 8% by weight of the microcapsule.

The different layers forming the coating may be based on identical or different polymers. Advantageously, they will be formed from the same polymer.

The microcapsules advantageously comprises at least:

- a core made of at least one reflective particle and or a monosaccharide-polyol, preferably mannitol,
- at least two different layers,
  - at least one hydrophilic polymer preferably selected from polysaccharide or derivatives, and more preferably from starch or derivatives,
- and advantageously at least one lipid based material, preferably an amphiphilic compound, more preferably a phospholipid, even more preferably phosphoacylglycerol such as hydrogenated lecithin.

Lipid-Based Material

The inner and/or outer layer(s) may also include advantageously at least one lipid-based material.

According to a particular embodiment of this invention, such a lipid-based material may have amphiphilic properties, that is to say having an apolar part and a polar part.

Such lipid-based material can include at least one or several $C_{12}$-$C_{22}$ fatty acid chain(s) such as those selected from stearic acid, palmitic acid, oleic acid, linoleic acid, linolenic acid, etc., and mixtures thereof. Preferably these fatty acids chains are hydrogenated. Eventually, these fatty acid chains may be the apolar part of a lipid-based material.

Such lipid-based material is preferably selected from phospholipids. These phospholipids are preferably selected from phosphoacylglycerol, more preferably selected from lecithins, and are in particular hydrogenated lecithin.

The lipid based material may represent from 0.05 to 5% by weight of the microcapsule, in particular from 0.1 to 1% by weight of microcapsule.

By combining three or more compounds (ex: sugar alcohols, polymers, lipid-based material) in the microcapsule of different hardness and/or water solubility, it is possible to adjust the time required for reflective particle-encapsulated microcapsules to break down on the skin. Thus, according to a preferred embodiment, the multi-layer coating contains at least starch as polymer and at least one lipid-based material, which is preferably lecithin.

According to an advantageous embodiment the microcapsules according to the invention include at least one monosaccharide or its derivative and at least one polysaccharide or its derivatives.

According to a preferred embodiment, the microcapsules include a core comprising a monosaccharide derivative and a coating comprising a polysaccharide (or its derivative) including one type of ose or several types of ose(s), preferably several types of oses.

According to a more preferably embodiment, the microcapsules include a core comprising a monosaccharide polyol, preferably selected from mannitol, erythritol, xylitol, sorbitol, and a coating comprising a polysaccharide (or its derivative) including as ose(s) at least one or more D-Glucose unit(s).

According to a preferred embodiment, the microcapsules additionally include a lipid-based material chosen from phospholipids, advantageously selected from phosphoacylglycerol and in particular from lecithins.

In a particular embodiment, the core contains mannitol, starch polymer and cellulose derivatives and optionally a lipid-based material. In such a case, the starch polymer is the main ingredient i.e. the weight amount of starch is greater than the respective amount of mannitol, cellulose derivative and lipid-based material of the core.

According to a particular embodiment of the invention, the microcapsules comprise at least:

- a core comprising at least one reflective particle, a monosaccharide-polyol, preferably mannitol, a lipid based material preferably lecithin and a hydrophilic polymer preferably starch,
- an inner layer comprising starch as a binder, a polymer selected form alkylacrylic/alkylmethacrylic acid copolymers and their derivatives, a lipid based material preferably hydrogenated lecithin, a plasticizer, microcrystalline cellulose, hydroxypropylcellulose and optionally at least one reflective particle which may be the same or different from the reflective particle contained ion the core,
- an outer layer comprising TiO2, a polymer preferably selected form alkylacrylic/alkylmethacrylic acid copolymers and their derivatives and a optionally a binder preferably starch.

According to another particular embodiment of the invention, the microcapsules comprise at least:

- a core comprising at least one, a monosaccharide-polyol, preferably mannitol, a lipid based material preferably lecithin and a hydrophilic polymer preferably starch,
- an inner layer made of comprising at least one reflective particle which may be the same or different from the refelective particle contained in the core, a monosaccharide-polyol, preferably mannitol, a lipid based material preferably hydrogenated lecithin,
- an outer layer made of a lipid based material preferably hydrogenated lecithin and a hydrophilic polymer preferably starch.

Reflective Particles

According to a particular embodiment, microcapsules used in the present invention comprise reflective particles in the form of flakes, more particularly having a ratio d/e greater than 10.

Reflective particles used in the present invention preferably have a refracting index greater or equal to 1.8. This allows to confer a light effect and radiance upon microcapsule rupture at the time of application of the composition.

The expression <<particles in the form of flakes>> means particles in a plate form. This means that these particles have a greatest dimension called <<d>> and a thickness called <<e>>, the ratio between the greatest dimension and the thickness of the particles that is "d/e" being greater than 10, preferably greater than 20, for example greater than 50.

The particles may have at least one plane face, or may have a radius of curvature that is greater than or equal to 60

μm. This may make it easier to stack the particles and to increase their specular reflective power.

A greatest dimension of the particles, whatever their shape, may lie in the range 5 μm to 100 μm, more preferably still in the range 10 μm to 60 μm. The size of the particles is preferably greater than or equal to 10 μm, better greater than or equal to 20 μm, still better greater than or equal to 40 μm.

The form factor "d/e" of said particles is advantageously greater than or equal to 10, better greater than or equal to 20, still better greater than or equal to 50.

Reflective particles in the form of flakes are preferably relatively monodispersed with regard to their greatest cross dimension, less or more 30%. This makes the particle deposit easier. Preferably their surface is regular, non-rough.

Measuring the Reflective Power of the Reflective Particles

The particles of reflective power that is to be measured is applied in uniform manner, at a rate of 0.2 milligrams per square centimeter ($mg/cm^2$), on a surface made of black Bioskin®, sold by Beaulax.

The reflective power is measured with the GP-5 goniophotometer sold by Murakami.

The angle of incidence is fixed at −45°, and the reflectance is measured over the range −90° to 90°. The reflectance maximum, corresponding to specular reflectance, is generally measured at 45°, and it is marked $R_{45}$. The reflectance minimum, corresponding to diffuse reflectance, is generally measured at −30°, and it is marked $R_{-30}$.

The reflective power of the particles is defined by $R_{45}/R_{-30}$.

The reflective power of the particles of the invention, may preferably be greater than 5, more preferably greater than 7, and better greater than 10.

The reflective particles, in particular particles in the form of flakes, are present at a content that is greater than or equal to 5% by weight, preferably greater than or equal to 10% by weight, better greater than or equal to 20% by weight, ETC and better still greater than or equal to 60% by weight, relative to the total weight of the powder composition, for example ranging from 10 to 90%, by weight relative to the total weight of the microcapsule.

According to a preferred embodiment, a bead according to the invention comprises reflective particles in the form of flakes and having a ratio d/e equal to or greater than 10 selected in the group consisting of:

- flake particles having at least two parallel faces that consist of a single material which is optically uniform; and
- flake particles that have a layered structure with at least two layers of material that are different optically preferably selected from pigments having a substrate and coating structure, or pigments that are multilayered without a substrate and their mixture, also called multilayer interference pigments,
- diffractive pigments,
- and mixtures thereof.

According to a preferred embodiment a bead according to the invention comprises particles in the form of flakes and having a ratio d/e equal to or greater than 10 selected in the group consisting of multilayer interference pigments and their mixture, preferably said multilayer interference pigments being selected from nacres, reflective interference particles, goniochromatic pigments and their mixture.

Preferably the Reflective Particles According to the Invention are Selected from Inorganic Particles Coated with Metallic (Poly)Oxydes.

As examples of substrates which may be coated by poly(oxydes), mica or synthetic fluorphologopite may be cited, preferably mica.

As examples of metallic (poly)oxydes, mention may be made of: titanium dioxide, iron oxide, tin oxide, and their mixture, and preferably of at least titanium dioxide.

According to a particular embodiment, such an inorganic particle is a mica-titanium dioxide, a mica-titanium dioxide-tin oxide or a mica-titanium dioxide-iron oxide particle.

Flake Particles Having at Least Two Parallel Faces that Consist of a Single Material that is Optically Uniform As examples of flake particles having at least two parallel faces that consist of a single material that is optically uniform, mention may be made of: metal-effect pigments, such as metal flakes, e.g. flakes of aluminum or of metal-alloy, e.g. copper-zinc alloy, silica, synthetic mica, or glass particles; or transparent-effect pigments such as crystalline bismuth oxychloride or polycrystalline titanium dioxide.

As examples of metal pigments, mention may be made of aluminum, bronze, or copper powders that are coated with $SiO_2$ and sold under the trade name VISIONAIRE by ECKART.

As examples of glass flakes, mention may be made of compositions sold under the name SILKYFLAKE by Nippon Sheet Glass.

As an example of bismuth oxychloride-based pigment, mention may be made of BIRON pigments sold by Merck, and PEARL compositions sold by FARMAQUIMIA.

Multilayer Interference Pigment

The expression "multilayer interference pigment" means a pigment that is capable of producing a color by an interference phenomenon between the light rays reflected by a plurality of superposed layers of different refractive indices, in particular a succession of layers of high and low refractive indices.

Any multilayer interference pigment may be envisaged.

Any color may be produced by the multilayer interference pigment, e.g. optionally being of dominant wavelength lying in the range 580 nm to 650 nm.

The composition may include a single multilayer interference pigment or a plurality of multilayer interference pigments having different dominant wavelengths.

The multilayer interference pigment may comprise a substrate (also known as a core) that is covered, on at least one face, by one or more layers made of materials and thicknesses that are selected such that a color is produced by interference.

Layers of the interference pigment may optionally surround the substrate which may present an optionally flat shape.

When reflective particles have a multilayer structure, they may comprise a natural or synthetic substrate, particularly a synthetic substrate at least partially coated by at least one layer of a reflective material in particular a layer made of metal or metallic material. The substrate may be made of a single material or a plurality of materials; it may be mineral or organic.

The substrate may include natural glass, ceramic, graphite, metal oxide, alumina, silica, silicates, particularly alumina-silicates, boro-silicates, synthetic mica, or their mixture.

The substrate may include natural mica, synthetic mica, glass, alumina, silica, or even any metal, alloy, or metal oxide.

The type of substrate could be selected as a function of the glossiness desired. For example, for a very glossy result, a substrate made of glass or of metal could be preferred.

The interference pigment may include more than four layers of different refractive indices.

The size of the particles of the multilayer interference pigment, given by the mean grain size at half the population, also referred to as $D_{50}$, lies in the range 1 μm to 2000 μm, for example, better in the range 5 μm to 2000 μm.

The proportion of multilayer interference pigment is greater than 7%, for example, and lies in the range 7% to 20%, for example, for a non-powder, liquid, or cast composition, e.g. a composition in stick form, and in the range 40% to 95%, for example, for a loose- or compacted-powder composition.

Nacres are examples of suitable multilayer interference pigments.

Nacres

The term "nacre" means colored particles of any form, which may optionally be iridescent, as produced in the shells of certain mollusks, or which are synthesized, and which exhibit a "pearlescent" coloring effect by optical interference.

Examples of nacres that may be mentioned are nacre pigments such as mica titanium coated with iron oxide, mica coated with bismuth oxychloride, mica titanium coated with chromium oxide, mica titanium coated with an organic colorant in particular, and nacre pigments based on bismuth oxychloride. "Mica titanium" means mica coated with $TiO_2$.

They may also be particles of mica on the surface of which at least two successive layers of metal oxides and/or organic coloring substances have been superimposed.

The nacres may have a yellow, pink, red, bronze, orangey, brown, gold, and/or coppery color or glint.

Illustrative examples of nacres suitable for being introduced as a multilayer interference pigment and that may be mentioned are gold color nacres, in particular those sold by ENGELHARD under the trade names Brillant gold 20 212G (Timica), Gold 222C (Cloisonne), Sparkle gold (Timica), Gold 4504 (Chromalite), and Monarch gold 233X (Cloisonne); bronze nacres, in particular those sold by MERCK under the trade names Bronze fine (17384) (Colorona) and Bronze (17353) (Colorona), and by ENGELHARD under the trade name Super bronze (Cloisonne); orange nacres in particular those sold by ENGELHARD under the trade names Orange 363C (Cloisonne) and Orange MCR 101 (Cosmica), and by MERCK under the trade names Passion orange (Colorona) and Matte orange (17449) (Microna); brown-tinted nacres in particular those sold by ENGELHARD under the trade names Nu-antique copper 340XB (Cloisonne) and Brown CL4509 (Chromalite); nacres with a copper glint in particular those sold by ENGELHARD under the trade name Copper 340A (Timica); nacres with a red glint, in particular those sold by MERCK under the trade name Sienna fine (17386) (Colorona); nacres with a yellow glint, in particular those sold by ENGELHARD under the trade name Yellow (4502) (Chromalite); red-tinted nacres with gold glints, in particular those sold by ENGELHARD under the trade name Sunstone G012 (Gemtone); pink nacres, in particular those sold by ENGELHARD under the trade name Tan opale G005 (Gemtone); black nacres with a gold glint, in particular those sold by ENGELHARD under the trade name Nu antique bronze 240 AB (Timica); blue nacres, in particular those sold by MERCK under the trade name Matte blue (17433) (Microna); white nacres with silvery glints, in particular those sold by MERCK under the trade name Xirona Silver; and orange-pink green-gold highlight nacres in particular those sold by MERCK under the trade names Indian summer (Xirona); and mixtures thereof.

Glass-based interference particles such as Ronastar sold by MERCK or synthetic mica-based interference particles such as Sunshine sold by SUN CHEMICAL or PROMINENCE sold by NIKON KOKEN and their mixture may also be cited.

By way of example, multilayer interference pigments presenting magnetic properties are those sold under the trade names: COLORONA BLACKSTAR BLUE, COLORONA BLACKSTAR GREEN, COLORONA BLACKSTAR GOLD, COLORONA BLACKSTAR RED, CLOISONNE NU ANTIQUE SUPER GREEN, MICRONA MATTE BLACK (17437), MICA BLACK (17260), COLORONA PATINA SILVER (17289), and COLORONA PATINA GOLD (117288) by MERCK; or indeed: FLAMENCO TWILIGHT RED, FLAMENCO 25 TWILIGHT GREEN, FLAMENCO TWILIGHT GOLD, FLAMENCO TWILIGHT BLUE, TIMICA NU ANTIQUE SILVER 110 AB, TIMICA NU ANTIQUE GOLD 212 GB, TIMICA NU-ANTIQUE COPPER 340 AB, TIMICA NU ANTIQUE BRONZE 240 AB, CLOISONNE NU ANTIQUE GREEN 828 CB, CLOISONNE NU ANTIQUE BLUE 626 CB, GEMTONE MOONSTONE G 004, CLOISONNE NU ANTIQUE RED 424 CB, CHROMA-LITE BLACK (4498), CLOISONNE NU ANTIQUE ROUGE FLAMBE (code 440 XB), CLOISONNE NU ANTIQUE BRONZE (240 XB), CLOISONNE NU ANTIQUE GOLD (222 CB), and CLOISONNE NU ANTIQUE COPPER (340 XB) by ENGELHARD.

The multilayer interference pigment may also be selected from the reflective interference particles.

Reflective Interference Particles

These particles may be selected from particles of synthetic substrate at least partially coated with at least one layer of at least one metal oxide selected, for example, from oxides of titanium, in particular $TiO_2$, of iron, in particular $Fe_2O_3$, of tin, or of chromium, barium sulfate, and the following materials: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_3$, $MoS_2$, and mixtures or alloys thereof.

More precisely as example of particle in the form of flakes having a layer structure, the following may be cited: particle in the form of flakes made of natural or synthetic mica coated with at least one layer of metal oxide, chosen from oxides of titanium, in particular $TiO_2$, of iron, in particular $Fe_2O_3$, of tin, or of chromium, barium sulfate, and the following materials: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$, and mixtures or alloys thereof.

Examples of such particles that may be mentioned are particles comprising a substrate of synthetic mica coated with titanium dioxide, or glass particles coated either with brown iron oxide, titanium oxide, tin oxide, or one mixture thereof such as those sold under the trade name REFLECKS® by ENGELHARD.

Other examples of such particles that may be mentioned are particles comprising a mineral substrate coated with a metal layer, particles having a boro-silicate substrate coated with silver sold under the trade name METASHINE® by Nippon Sheet Glass.

The multilayer interference pigment may also be a goniochromatic pigment.

Goniochromatic Pigment

The term "goniochromatic pigment" as used in the context of the present invention means a pigment that makes it possible, when the composition is spread on a substrate, to obtain a color path in the a*b* plane of the 1976 CIE color space which corresponds to a variation Dh° of the hue angle h° of at least 20° when the angle of observation is varied relative to the normal in the range 0 to 80° for light at an angle of incidence of 45°.

By way of example, the color path may be measured by means of a spectrogonioreflectometer, from INSTRUMENT SYSTEMS and referenced GON 360 GONIOMETER, after the composition has been spread in the fluid state to a thickness of 300 μm by means of an automatic spreader on a contrast card from ERICHSEN and referenced Typ 24/5, the measurements being performed on the black background of the card.

The goniochromatic pigment may, for example, be selected from multilayer interference structures and liquid crystal coloring agents.

By way of example, a multilayer structure may comprise at least two layers, each layer being produced, for example, from at least one material selected from the group constituted by the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_3$, $Ta_2O_5$, $TiO_2$, Ag, Al, Au, Cu, Rb, Ti, Ta, W, Zn, $MoS_2$, cryolite, alloys, polymers, and combinations thereof.

The multilayer structure may optionally be symmetrical with respect to a central layer as regards the chemical nature of the stacked layers.

Depending on the thickness and nature of the various layers, different effects are obtained.

Examples of symmetrical multilayer interference structures are as follows: $Fe_2O_3/SiO_2/Fe_2O_3/SiO_2/Fe_{23}$, a pigment having this structure being sold under the trade name SICOPEARL by BASF; $MoS_2/SiO_2$/mica-oxide/$SiO_2/MoS_2$; $Fe_2O_3/SiO_2$/mica-oxide/$SiO_2/Fe_2O_3$; $TiO_2/SiO_2/TiO_2$ and $TiO_2/Al_2O_3/TiO_2$, pigments having these structures being sold under the trade name XIRONA by MERCK (Darmstadt).

By way of example, liquid crystal coloring agents comprise silicones, or cellulose ethers onto which mesomorphic groups have been grafted. Examples of suitable liquid crystal goniochromatic particles are those sold by CHENIX, and those sold under the trade name HELICONE® HC by WACKER.

Suitable goniochromatic pigments are some nacres; pigments having effects on synthetic substrates, in particular alumina, silica, borosilicate, iron oxide, or aluminum type substrates; or interference flakes coming from a polyterephthalate film.

The material may further contain dispersed goniochromatic fibers. Such fibers could present a length that is less than 80 μm, for example.

Diffracting Pigment

The term "diffracting pigment" as used in the present invention means a pigment which is capable of producing a color variation depending on the angle of observation when illuminated with white light due to the presence of a structure which diffracts light.

Such a pigment is also sometimes termed a holographic pigment or rainbow effect pigment.

A diffracting pigment may comprise a diffraction matrix capable, for example, of diffracting an incident ray of monochromatic light in predetermined directions.

The diffraction matrix may comprise a periodic motif, in particular a line, the distance between two adjacent motifs being of the same order of magnitude as the wavelength of the incident light.

When the incident light is polychromatic, the diffraction matrix separates the various spectral components of the light and produces a rainbow effect. Concerning the structure of diffracting pigments, reference should be made to the article "*Pigments Exhibiting Diffractive Effects*" by Alberto Argoitia and Matt Witzman, 2002, Society of Vacuum Coaters, $45^{hh}$ Annual Technical Conference Proceedings, 2002, the contents of which are hereby incorporated by reference.

The diffracting pigment may be produced with motifs having different profiles, in particular triangular, symmetrical or unsymmetrical, crenellated, with a constant or non constant width, sinusoidal, or stepped.

The spatial frequency of the matrix and the motif depth will be selected as a function of the desired degree of separation of the various orders. As an example, the frequency may lie in the range 500 to 3000 lines per mm.

Preferably, the particles of diffracting pigment each have a flattened form, in particular in the form of a platelet. The same pigment particle may comprise two crossed diffraction matrices, which may or may not be perpendicular, and may or may not have the same spacing.

The diffracting pigment may have a multi-layered structure comprising a layer of reflective material, covered on at least one side by a layer of a dielectric material. This layer may provide the diffracting pigment with better rigidity and durability. The dielectric material may thus, for example, be selected from the following materials: $MgF_2$, $SiO_2$, $Al_2O_3$, $AlF_3$, $CeF_3$, $LaF_3$, $NdF_3$, $SmF_2$, $BaF_2$, $CaF_2$, LiF, and combinations thereof.

The reflective material may, for example, be selected from metals and their alloys and also from non-metallic reflective materials. Metals which may be mentioned include Al, Ag, Cu, Au, Pt, Sn, Ti, Pd, Ni, Co, Rd, Nb, Cr, and their materials, combinations or alloys. Such a reflective material may alone constitute the diffracting pigment which is then a monolayer.

In a variation, the diffracting pigment may comprise a multi-layered structure comprising a substrate of a dielectric material covered on at least one side by a reflective layer, or even completely encapsulating the substrate.

A layer of a dielectric material may also cover the reflective layer or layers. The dielectric material used is thus preferably inorganic and may, for example, be selected from metal fluorides, metal oxides, metal sulfides, metal nitrides, metal carbides and combinations thereof. The dielectric material may be in the crystalline, semi-crystalline or amorphous state. The dielectric material in this configuration may, for example, be selected from the following materials: $MgF_2$, SiO, $SiO_2$, $Al_2O_3$, $TiO_2$, WO, AlN, BN, $B_4C$, WC, TiC, TiN, $N_4Si_3$, ZnS, glass particles, diamond type carbons, and combinations thereof. In a variation, the diffracting pigment may be composed of a dielectric or preformed ceramic material such as a mineral in natural lamellae, for example mica peroskovite or talc, or synthetic lamellae formed from glass, alumina, $SiO_2$, carbon, an iron oxide/mica, mica coated with BN, BC, graphite, bismuth oxychloride, and combinations thereof.

Instead of a layer of a dielectric material, other materials which improve the mechanical properties may be suitable. Such materials may include silicone, metal silicides, semiconductor materials formed from elements from groups III, IV, and V, metals having a body-centered cubic crystal structure, Cermet compositions or materials, semiconductor glasses, and their various combinations. The diffracting pigment used may in particular be selected from those described in United States patent application US-2003/0031870 published on Feb. 13, 2003. A diffracting pigment may, for example, comprise the following structure: $MgF_2/Al/MgF_2$, a diffracting pigment having that structure being sold under the trade name SPECTRAFLAIR 1400 Pigment Silver by FLEX PRODUCTS, or SPECTRFLAIR 1400 Pigment Silver FG. The proportion by weight of $MgF_2$ may be in the range 80% to 95% of the total weight of the pigment. Other diffracting pigments are sold under the trade names METALURE® PRISMATIC by ECKART®.

Other possible structures are Fe/Al/Fe or Al/Fe/Al.

The dimension of the diffracting pigment may, for example, be in the range 5 μm to 200 μm, better in the range 5 μm to 100 μm, for example in the range 5 μm to 30 μm. The thickness of the particles of diffracting pigment may be 3 μm or less, preferably 2 rpm, for example of the order of 1 μm.

II—Methods for Preparing Microcapsules

The microcapsules may be produced by a process including preparing an aqueous solution containing water, and a first hydrophilic polymer, dispersing reflective particles in the aqueous solution;

forming an inner layer on a core with the aqueous solution in which the reflective particles are dispersed;

forming an intermediate layer on the inner layer with an intermediate layer solution containing water, a second hydrophilic polymer, and a pigment; and forming an outer layer on the intermediate layer with an outer layer solution containing water and a third hydrophilic polymer.

The hydrophilic polymer, the reflective particles, the pigment, and the core can be any one or combination of those listed above. The properties such as the size of the core or the reflective particles can be the same as those described above. The first, second, and third hydrophilic polymers can be the same or different.

Preferably, the microcapsules are produced by this process and comprise a combination of reflective particles and at least one polymer chosen from poly-vinyl Alcohol (PVA); starch polymers and derivatives, preferably hydroxypropylstarch phosphate; ethylcellulose; hydroxypropylmethylcellulose and their mixtures; preferably a combination of reflective particles, poly-vinyl Alcohol (PVA) and hydroxypropylstarch phosphate.

Preferably, the combination of reflective particles and at least one polymer chosen from poly-vinyl Alcohol (PVA); starch polymers and derivatives; ethylcellulose; hydroxypropylmethylcellulose and their mixtures is in the inner layer.

According to a particular embodiment of the invention, the microcapsules comprise at least:

a core comprising a monosaccharide-polyol, preferably mannitol, an inner layer comprising the combination of reflective particles and at least one polymer chosen from poly-vinyl Alcohol (PVA); starch polymers and derivatives; ethylcellulose; hydroxypropylmethylcellulose and their mixtures is in the inner layer, an outer layer comprising TiO2, a polymer and a optionally a binder.

Preferably the reflective particles is chosen among nacres.

The amount of each of water, the hydrophilic polymer, and the core can be any amount determined by a person of ordinary skill in the art. For example, the aqueous solution can be prepared by dissolving 100-200 weight parts of the hydrophilic polymer in 7,000-16,000 weight parts of water, and 500-1,500 weight parts of the reflective particles can be added to the solution. In another example, a mixture of water and alcohol can be used instead of water. For example, 500-1,000 g of the core is coated with a spray drying process. For example, the solution for the intermediate layer can contain 2,000-5,000 weight parts of water and 2-10 weight parts of the lipid, and 10-40 weight parts of the hydrophilic polymer. For example, the solution for the outer layer can contain 300-500 weight parts of water, 1-3 weight parts of the hydrophilic polymer, and optionally 0.5-1.5 weight parts of the lipid.

The aqueous solution can be prepared with an appropriate way. For example, the hydrophilic polymer can be dissolved in the solution at 50-100° C., preferably 75-99° C., for example, 95° C.

The aqueous solution can be prepared by mixing two solutions, each of which contains different hydrophilic solutions containing, for example, different hydrophilic polymers. For example, one contains a starch derivative, and another contains polyvinyl alcohol. The aqueous solution can contain another aqueous solvent, for example, a lower alcohol such as ethanol. At least one of the layers can contain a lipid such as one of those listed above.

The coating step can be carried out with a spray drying process.

The microcapsules may be produced by several methods known to the man skilled in the art within the coating or encapsulation domain, including spray drying, pelletization, granulation, coating, etc.

Spray drying processes may be carried out by any method e.g. tangential, bottom or top spray drying. It may also be combined with a drying in a fluidized bed process. These alternatives may further be combined in order to obtain microcapsules having the required properties.

Preferably at least one outer layer, more preferably all outer layers are obtained by a combination of one or several of these alternatives: tangential, bottom or top spray drying optionally combined with a fluidized bed process.

For example, the microcapsules may be obtained by a method comprising mixture of the compounds (reflective particles, other optional actives, polymers, solvents) and drying to form capsules as disclosed in WO01/35933 and WO2011/027960, or a method comprising granulation and coating by spray drying as disclosed in FR2841155, or by fluidized bed technology, which has been used in the food and pharmaceutical industry for a long time for coating and encapsulating ingredients. As an example may be cited WO2008/139053, which concerns the preparation of spheroid multilayer capsules comprising a core of sugar and concentric layers of pharmaceutical actives. Fixation of pharmaceutical actives on the core is achieved by impregnation, pulverization or projection, and then the $1^{st}$ layer is dried before application of a second one.

IIa—Fluid Bed Process

Fluid bed process is disclosed for example in Teunou et al. (Fluid-Bed Coating, Poncelet, 2005, D. *Food Science and Technology* (Boca Raton, Fla., United States), Volume 146 Issue Encapsulated and Powdered Foods, Pages 197-212). A specific feature of the fluid bed process is that it leads to coated particles wherein the core is well encapsulated, compared to spray drying, which leads to a matrix with the core material randomly dispersed in a polymer.

In a preferred embodiment, the microcapsules are obtained by fluid bed process.

According to this embodiment, preferably at least one layer of the microcapsules is obtained by fluid bed process.

In a particular embodiment, the outer layer is obtained by fluid bed process.

In another particular embodiment at least one inner layer is obtained by fluid process.

At least one layer, most preferably, all layers are obtained by fluid bed process.

The man skilled in the art knows how to adjust air quantity, liquid quantity and temperature allowing to reproduce a microcapsule according to the invention.

Preferably a fluid bed process implemented according to the invention includes Würster process and/or tangential spray process. Such a process allows, contrary to a pelletization process, to prepare spherical capsules with a core surrounded by one or more circumferential layers.

When the whole process for preparing the layers surrounding the core of the microcapsules according to the invention is carried out by fluid bed process, the microcapsule layers are advantageously regular, concentric and present a homogenous thickness.

Advantageously this water acts as a swelling agent or as a softening agent towards these microcapsules without breaking them. The microcapsules are not inert when placed in water either they swell: their diameter significantly increases with an optional softening of the microcapsules, or the microcapsules significantly soften without increasing of the diameter, they become more malleable and easier to break when applied onto the skin.

Water is able to act on the softening kinetics of the microcapsules and more particularly it allows to obtain a good balance between softening kinetics and hardness.

As a consequence, water is particularly advantageous for softening these microcapsules suitable for the present invention, in an appropriate way, since it plays a role on softening kinetics of said microcapsules.

Said microcapsules are preferably deformable in the presence of an aqueous phase, notably in the presence of water.

According to this embodiment of the invention, composition comprise water in a content ranging from 30% to 99% by weight, preferably from 40% to 95% more preferably from 50% to 90% by weight relative to the total weight of the said composition.

Optionally it also comprises at least one compound chosen from polyols, glycols and $C_2$-$C_8$ monoalcohols, and mixtures thereof.

Said polyol is preferably selected from the group consisting in glycerol, glycols, preferably propylene glycol, butylene glycol, pentylene glycol, hexylene glycol, dipropylene glycol, diethylene glycol, glycol ethers, preferably mono-, di- or tripropylene glycol of alkyl($C_1$-$C_4$)ether or mono-, di- or triethylene glycol of alkyl($C_1$-$C_4$)ether, and mixtures thereof.

Compositions according to this embodiment are advantageously in the form of an oil-in-water emulsion.

Two major alternative processes for preparing the microcapsules according to the invention may also be mentioned: microencapsulation and coacervation.

IIb—Microencapsulation

Any suitable microencapsulation method can be used according to the present invention. In most preferred embodiments, the microencapsulation method is based on the solvent removal method as described in U.S. Pat. No. 6,932,984 and U.S. patent application Ser. No. 11/208,007 (Publication US 2006/0051425).

Thus, microcapsules for use in the compositions of the present invention, encapsulating in their core one or more reflective particles, and comprising one or more layers of the same or different wall-forming polymer, are produced by a method comprising the steps of:

(a) preparing an organic solution comprising: (i) a reflective particle dissolved or dispersed therein; (ii) a wall-forming polymer selected from the group consisting of a polyacrylate, a polymethacrylate preferably of low molecular weight about 15,000 D, poly(methyl methacrylate)-co-(methacrylic acid), poly(ethyl acrylate)-co-(methyl methacrylate)-co-(trimethylammonium-ethyl methacrylate chloride), poly(butyl methacrylate)-co-(2-dimethylaminoethyl methacrylate)-co-(methyl methacrylate), poly(styrene)-co-(maleic anhydride), copolymer of octylacrylamide, cellulose ethers, cellulose esters and poly(ethylene glycol)-block-poly(propylene glycol)-block-poly(ethylene glycol); (iii) an organic solvent of a kind that is partially miscible with water and is capable of dissolving or dispersing the substances of (i) and (ii); and, optionally, (iv) an antioxidant, a plasticizer or both;

(b) preparing an aqueous continuous phase saturated with said organic solvent and comprising an emulsifier;

(c) while agitating, pouring the organic solution or dispersion of (a) into the aqueous continuous phase of (b) to form an emulsion;

(d) adding an excess amount of water to the emulsion obtained in (c) to initiate extraction of the organic solvent from the emulsion, and continuing the extraction by incubating the solvent, thus promoting the formation of solid single-layer microcapsules (hereinafter "the core microcapsules");

(e) isolating the core microcapsules, washing with water or an aqueous solution of alcohol and drying them, thus obtaining single-layer microcapsules; and, optionally (f) forming multi-layer microcapsules by treating the surface of the dried core single-layer microcapsules of (e) with a material that modifies the morphology of the core surface, increases its specific surface area and facilitates the adhesion of an additional polymeric shell, and either repeating steps (a) to (e) to form double layer microcapsules, or repeating steps (a) to (f) followed by steps (a) to (e) one or more times to add two or more additional layers surrounding the core microcapsule.

Preferably the so-obtained microcapsules comprise a core comprising at least one reflective particle, at least one layered coating surrounding said core, the layered coating comprising at least one hydrophilic polymer.

Preferably, the hydrophilic polymer(s) is selected from (poly)(alkyl)(meth)acrylic acid and derivatives, notably (poly)(alkyl)(meth)acrylate and derivatives, preferably from alkylacrylic/alkylmethacrylic acid copolymers and their derivatives, and most preferably is a copolymer of ethyl acrylate, methyl methacrylate and low content of methacrylic acid ester with quaternary ammonium groups.

According to a particular embodiment, at least one layer, preferably all layers of the microcapsules is/are obtained by a microencapsulation process.

IIc—Coacervation

Another preferred method for preparing the microcapsules is the technique of coacervation. Under this method, a liquid dispersion is emulsified in a continuous, external aqueous phase to form micro-sized droplets and a complex of colloidal material added to the external phase is reacted upon in such a way to form a deposit on and around each droplet thereby forming an outer wall or shell.

After the formation of the outer shells, the temperature of the aqueous coacervating solution is lowered causing gelation and hardening of the shell wall material.

The hardening may be accomplished by applying a condensate polymer and a cross-linking agent like glutaraldehyde.

The hardening should be sufficient so that the microencapsules may be removed from the continuous external phase and dehydrated to form a stable, dry, free flowing powder capable of being handled easily and further processed to make cosmetic products without undue rupture of the microcapsules.

When the preferred coacervation method is used to form the microcapsules, the size of the cores, as well as the wall thickness and strength of the outer walls or shells, may be controlled precisely by altering such factors as the pH of the aqueous phase, the relative concentration of the colloids in the aqueous phase, the degree of agitation of the coacervation solution, the temperature and duration of the reaction, the degree of cross-linking, and so on, all as is fully known and understood in the art.

Preferably the so-obtained microcapsules comprise

- a core comprising at least one reflective particle dispersed in water,
- at least one layered coating surrounding said core, the layered coating comprising at least one colloidal material and a crosslinking agent of said colloidal material.

Advantageously, the colloidal material is selected from gelatin, gum arabic, carboxy methylcellulose and polyphosphate.

The condensate polymer may be selected from urea formaldehyde polymer, melamine formaldehyde (MF), poly-vinyl Alcohol (PVA).

According to a particular embodiment at least one layer, preferably all layers of the microcapsules is/are obtained by a coacervation process.

The microcapsules obtained according to these processes of microencapsulation and coacervation may be deformable in the presence of a liquid fatty phase preferably an oily phase and/or in the presence of an aqueous phase.

The microcapsules obtained according to these processes of microencapsulation are advantageously deformable in the presence of a liquid fatty phase preferably an oily phase.

Advantageously this liquid fatty phase acts as a swelling agent or as a softening agent towards these microcapsules without breaking them. The microcapsules are not inert when placed in this liquid fatty phase either they swell: their diameter significantly increases with an optional softening of the microcapsules, or the microcapsules significantly soften without increasing of the diameter, they become more malleable and easier to break when applied onto the skin.

The liquid fatty phase is able to act on the softening kinetics of the microcapsules and more particularly it allows to obtain a good balance between softening kinetics and hardness.

As a consequence, the liquid fatty phase is particularly advantageous for softening these microcapsules suitable for the present invention, in an appropriate way, since it plays a role on softening kinetics of said microcapsules.

Said microcapsules are deformable in the presence of the liquid fatty phase.

According to this embodiment of the invention, composition comprise a liquid fatty phase in a content ranging from 30% to 99% by weight, preferably from 40% to 95% more preferably from 50% to 90% by weight relative to the total weight of the said composition.

Compositions according to this embodiment are advantageously in the form of an water-in-oil emulsion.

The so-prepared microcapsules will be integrated in the cosmetic formula generally at the latest stages of the formulation and after filtering stages if any, to avoid the microcapsules being broken. Preferably, the microcapsules according to the inventions are added and mixed uniformly at temperatures under 50° C. They are mixed gently with a paddle rather than a homogenizer.

III—Composition

A composition according to the invention is cosmetically acceptable that is it contains a physiologically acceptable medium which is non toxic and appropriate to be applied on the keratin material of human beings.

"Cosmetically acceptable" in the sense of the present invention means a composition with pleasant appearance, odor or feeling.

The "physiologically acceptable medium" is generally adapted to the form of under which the composition is intended to be conditioned.

Particularly the nature and the amount of the ingredients are adapted for example depending on whether the composition is formulated as a solid, a fluid or a powder.

Depending upon the form and the aim of the skin care or make-up preparation, the composition of the invention may comprise, in addition to the microcapsules, further additional cosmetic ingredient(s) such as the ones selected from volatile and non-volatile silicon or hydrocarbon oils, surfactants, fillers, thickening agents, film forming agents, polymers, preservatives, reflective particle, self-tanning agents, colorants, actives, UV filters, perfumes, pH regulators and mixtures thereof.

The pH of the cosmetic composition according to the present invention ranges preferably from 6.5 to 7.5. A preferred base to modify the pH is triethanolamine.

It is a matter of routine operations for a person skilled in the art to adjust the nature and amount of the additives present in the compositions in accordance with the invention such that the desired cosmetic properties thereof are not thereby affected.

Some of these conventional ingredients are detailed hereafter.

Aqueous Phase

As previously stated, an aqueous phase may be particularly advantageous for imparting and/or improving deformability to the microcapsules of the invention.

The aqueous phase comprises water and, where appropriate, a water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

As said, the compositions of the invention may advantageously contain an aqueous phase comprising water and at least one compound chosen among polyols, glycols, $C_2$-$C_8$ monoalcohols and mixtures thereof. It also may contain $C_4$ ketones and $C_2$-$C_4$ aldehydes.

The aqueous phase is preferably present in an amount of at least 3% by weight, preferably at least 5% by weight, more preferably at least 8% by weight and advantageously at least 10% by weight relative to the weight of the composition.

Advantageously, the aqueous phase is present in an amount of at least 30% by weight, preferably at least 40% by weight, more preferably at least 50% by weight relative to the weight of the composition. Generally water is present in an amount ranging from 30% to 90% by weight, preferably 40% to 85% by weight and more preferably from 50 to 80% by weight, relative to the weight of the composition.

Advantageously, the aqueous phase may be present in a content ranging from 30% to 99% by weight, preferably from 40% to 95% more preferably from 50% to 90% by weight relative to the total weight of the said composition.

The composition of the invention will generally comprise at least one compound chosen from polyols, glycols, $C_2$-$C_8$ monoalcohols, and mixtures thereof in amount ranging from 3% to 50% by weight, preferably from 5% to 45% by weight and more preferably from 10% to 45% by weight relative to the total weight of the composition.

In a preferred embodiment, the aqueous phase suitable for the present invention comprises at least one $C_2$-$C_8$ monoalcohols.

In another preferred embodiment, the aqueous phase suitable for the present invention comprises at least one polyol or glycol.

In another preferred embodiment, the aqueous phase suitable for the present invention comprises at least one $C_2$-$C_8$ monoalcohols and at least one polyol or glycol.

Monoalcohols or Lower Alcohols

Monoalcohol or lower alcohol that is suitable for use in the invention may be a compound of linear, branched or cyclic, saturated or unsaturated alkyl type, bearing only one —OH function.

Advantageously, $C_2$-$C_8$ monoalcohols are non cyclic monoalcohols, still preferably they are $C_2$-$C_8$ monoalcohols and preferably $C_2$-$C_3$ monoalcohols.

The lower monoalcohols that are advantageously suitable for formulating a composition according to the present invention are those especially containing from 2 to 5 carbon atoms such as ethanol, propanol, butanol, isopropanol, isobutanol preferably ethanol and/or isopropanol and more preferably at least ethanol.

A composition of the invention may comprise at least 1% by weight, preferably at least 2%, more preferably from 2% to 15%, advantageously from 3% to 10%, by weight and better still from 3% to 8% by weight, preferably from 4% to 6% by weight of mono-alcohol(s) relative to the total weight of said composition.

In a preferred embodiment, a composition of the invention comprises ethanol and/or isopropanol and more preferably at least ethanol, in a total concentration of 2 to 15% by weight and more preferably of 3 to 10% by weight relative to the total weight of said composition.

Lower monoalcohols such as ethanol can be advantageous used in many ways in the field of makeup and/or care of keratin material(s).

Such compounds are particularly useful for providing a fresh feeling to the user when he applied on the skin, a composition of the invention.

Furthermore, such a feeling of freshness, pleasant as such to the user, may also advantageously allow to activate blood circulation in the skin where it is felt, especially in the skin surrounding the eyes which forms a particularly well vascularized area. The fresh feeling accompanying the application of these lower monoalcohols thus reduces puffiness and dark circles present in this part of the face due to the high vascularity and thinness in this part of the face.

The application of lower monoalcohols can also advantageously avoid the need to apply other cooling agents such as menthol, ethyl menthane carboxamide, menthyl lactate, menthoxypropanediol around the eyes, which are generally raw material irritating to the eyes.

There is also a need to have at disposal compositions containing microcapsules in a physiological medium comprising a lower alcohol because some cosmetic ingredients are particularly soluble in hydroalcoholic media.

Furthermore, the lower monoalcohols such as ethanol allow to dissolve active agents, especially keratolytic agents, such as, for example, salicylic acid and its derivatives.

Some microcapsules of the prior art rapidly disintegrate in hydroalcoholic media, as a consequence there was a need to have at disposal compositions comprising microcapsules stable in hydroalcoholic media.

Polyols and Glycols

For the purposes of the present invention, the term “polyol” should be understood as meaning any organic molecule comprising at least two free hydroxyl groups. The term “polyol” according to the invention does not encompass monosaccharide-alcohol disclosed above.

Preferably, a polyol in accordance with the present invention is present in liquid form at room temperature.

The polyols/glycols are moisturizers or humectants.

They may have an effect towards the stability of other ingredients of the composition particularly towards microcapsules of the prior art.

There is thus a need to have at disposal stable compositions containing microcapsules in a physiological medium comprising a polyol and/or a glycol because these compositions present a noticeable moisturizing or humecting effect.

This technical problem is solved by the compositions according to the invention. A polyol that is suitable for use in the invention may be a compound of linear, branched or cyclic, saturated or unsaturated alkyl type, bearing on each alkyl chain at least two —OH functions, in particular at least three —OH functions and more particularly at least four —OH functions.

The polyols that are advantageously suitable for formulating a composition according to the present invention are those especially containing from 2 to 32 carbon atoms preferably 2 to 20 carbon atoms and more preferably 2 to 16 carbon atoms, advantageously 2 to carbon atoms, more advantageously 2 to 6 carbon atoms.

According to another embodiment, a polyol that is suitable for use in the invention may be advantageously chosen from polyethylene glycols.

According to one embodiment, a composition of the invention may comprise a mixture of polyols.

Advantageously, the polyol may be chosen from polyhydric alcohols, preferably of $C_2$-$C_8$ and more preferably $C_3$-$C_6$. The polyol may be chosen from glycerol, pentaerythritol, trimethylolpropane, ethylene glycol, propylene glycol, 1,3-butylene glycol, 1,3-propanediol, pentylene glycol, hexylene glycol, isoprene glycol, dipropylene glycol, diethylene glycol and diglycerol, ethylhexylglycerine, caprylyl glycol and mixtures thereof, glycerol and derivatives thereof, polyglycerols, such as glycerol oligomers, for instance diglycerol, and polyethylene glycols, glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

Particularly, the polyol is selected from the group consisting in glycerol, glycols, preferably propylene glycol, butylene glycol, pentylene glycol, hexylene glycol, dipropylene glycol, diethylene glycol, ethylhexylglycerine, caprylyl glycol, glycol ethers, preferably mono-, di- or tripropylene glycol of alkyl(C1-C4)ether or mono-, di- or triethylene glycol of alkyl(C1-C4)ether, and mixtures thereof.

According to one preferred embodiment of the invention, the said polyol is chosen from ethylene glycol, pentaerythritol, trimethylolpropane, propylene glycol, butylene glycol, glycerol, polyglycerols and polyethylene glycols, and mixtures thereof.

In a particular embodiment, the polyol is selected from the group consisting in glycerol, and glycols chosen from propylene glycol, butylene glycol, ethylhexylglycerine, caprylyl glycol and mixtures thereof.

According to one particular embodiment, the composition of the invention comprises at least butylene glycol, glycerol or a mixture thereof.

In a preferred embodiment, the composition comprises at least glycerol.

According to one particular embodiment, the composition of the invention comprises glycerol as sole polyol.

Advantageously the composition may comprise from 1 to 10, preferably from 2 to 8 weight percent of glycerol based on the total weight of the composition Advantageously the composition may comprise from 1 to 10, preferably from 2 to 8 weight percent of butylene glycol based on the total weight of the composition.

Advantageously the composition may comprise from 1 to 10, preferably from 2 to 8 weight percent of propylene glycol based on the total weight of the composition.

When the composition comprises glycerol and at least one glycol, the weight ratio of glycerol/glycol is advantageously from 1/2 to 3/2, preferably from 2/3 to 1/1 more preferably around 1.

In a preferred embodiment, the composition comprises glycerol and at least one glycol chosen from propylene glycol, butylene glycol, ethylhexylglycerine, caprylyl glycol, the weight ratio of glycerol/glycol is advantageously from 1/2 to 3/2, preferably from 2/3 to 1/1 more preferably around 1.

A composition according to the invention may advantageously comprise at least 10% by weight, preferably between 10 and 45% by weight and in particular between 10% and 40% by weight of polyol(s) and/or glycols, preferably one $C_2$-$C_{32}$ polyol and/or glycol, based on weight of the composition.

A composition according to the invention may advantageously comprise at least 10% by weight, preferably from 12% to 50% by weight and in particular from 13% to 40%, more preferably from 14 to 35% and better from 15% to 30% by weight of polyol(s) and/or glycols based on weight of the composition.

A composition according to the invention may advantageously comprise at least 10% by weight, preferably from 12% to 50% by weight and in particular from 13% to 40%, more preferably from 14 to 35% and better from 15% to 30% by weight of polyol(s) and/or glycols based on weight of the aqueous phase.

Preferably the polyol is a $C_2$-$C_{32}$ polyol and/or glycol.

Advantageously the weight ratio of polyol and glycol/composition is from 1/10 to 1/2 preferably from 1/8 to 1/3, more preferably from 1/6 to 1/4. More particularly the weight ratio of polyol and glycol/aqueous phase is from 1/10 to 1/2 preferably from 1/8 to 1/3, more preferably from 1/6 to 1/4.

As detailed here-after, a composition may comprised a gelified aqueous phase.

The composition according to the invention may also be anhydrous or non-anhydrous.

In anhydrous compositions according to the invention, the "at least one compound chosen from polyols, glycols, $C_2$-$C_8$ monoalcohols, and mixtures thereof" is present in an amount of at least 3% by weight, preferably at least 5% by weight, more preferably at least 8% by weight and advantageously at least 10% by weight relative to the weight of the composition, and the composition is devoid of water.

"Devoid of water" means that the composition comprises less than 3% preferably less than 1% more preferably less than 0.5% of water and is especially free of water.

Where appropriate, such small amounts of water may especially be introduced by ingredients of the composition that may contain residual amounts thereof.

In non-anhydrous compositions according to the invention, the "at least one compound chosen from polyols, glycols, $C_2$-$C_8$ monoalcohols, and mixtures thereof" is advantageously present in an amount of at least 10% by weight, preferably at least 12% by weight, more preferably at least 15% by weight relative to the weight of the composition.

Liquid Fatty Phase

A composition according to the invention may also advantageously comprise at least one fatty phase that is liquid at room temperature and atmospheric pressure, and especially at least one oil as mentioned below.

Specifically, the presence of at least one oil is advantageous insofar as it facilitates the application of the composition and affords emollience.

According to the present invention, the term "oil" means a water-immiscible non-aqueous compound that is liquid at room temperature (25° C.) and at atmospheric pressure (760 mmHg).

An oily phase that is suitable for preparing an anhydrous cosmetic composition according to the invention may comprise hydrocarbon-based oils, silicone oils, fluoro oils or non-fluoro oils, or mixtures thereof.

The oils may be volatile or non-volatile.

They may be of animal, plant, mineral or synthetic origin. According to one embodiment variant, oils of plant origin are preferred.

The term "volatile oil" means any non-aqueous medium that is capable of evaporating on contact with the skin or the lips in less than one hour, at room temperature and atmospheric pressure. The volatile oil is a cosmetic volatile oil, which is liquid at room temperature. More specifically, a volatile oil has an evaporation rate of between 0.01 and 200 $mg/cm^2/min$, limits inclusive.

The term "non-volatile oil" means an oil that remains on the skin or the keratin fibre at room temperature and atmospheric pressure. More specifically, a non-volatile oil has an evaporation rate strictly less than 0.01 $mg/cm^2/min$.

To measure this evaporation rate, 15 g of oil or oil mixture to be tested are placed in a crystallizing dish 7 cm in diameter, placed on a balance that is in a large chamber of about 0.3 $m^3$ which is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area ($cm^2$) and per unit of time (minutes).

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

Advantageously, an anhydrous composition of the invention may comprise from 10% to 50% by weight and preferably from 20% to 40% by weight of oil(s) relative to the total weight of the said composition.

a) Volatile Oils

The volatile oils may be chosen from hydrocarbon-based oils containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, for instance the oils sold under the trade names Isopar® or Permethyl®, or especially linear $C_8$-$C_{14}$ alkanes.

Volatile oils that may also be used include volatile silicones, for instance volatile linear or cyclic silicone oils, especially those with a viscosity ≤8 centistokes (cSt) ($8\times10^{-6}$ $m^2/s$), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

Advantageously, a liquid fatty phase of the invention may comprise from 1% to 50% by weight, preferably from 2% to 40% by weight and better still from 5% to 30% by weight of volatile oil(s) relative to the total weight of the said liquid fatty phase.

b) Non-Volatile Oils

The non-volatile oils may be chosen especially from nonvolatile hydrocarbon-based, fluoro and/or silicone oils.

Non-volatile hydrocarbon-based oils that may especially be mentioned include:

- hydrocarbon-based oils of animal origin,
- hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from C4 to C36 and especially from C18 to C36, these oils possibly being linear or branched, and saturated or unsaturated; these oils may especially be heptanoic or octanoic triglycerides, shea oil, alfalfa oil, poppy oil, millet oil, barley oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camellina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, *quinoa* oil, musk rose oil, sesame oil, soybean oil, sunflower oil, castor oil and watermelon oil, and mixtures thereof, or alternatively caprylic/capric acid triglycerides, such as those sold by the company Stearineries Dubois or those sold under the names Miglyol 810®, 812® and 818® by the company Dynamit Nobel;
- linear or branched hydrocarbons, of mineral or synthetic origin, such as liquid paraffins and derivatives thereof, petroleum jelly, polydecenes, polybutenes, hydrogenated polyisobutene such as Parleam, and squalane,
- synthetic ethers containing from 10 to 40 carbon atoms, such as dicaprylyl ether,
- synthetic esters, for instance oils of formula R1COOR2, in which R1 represents a linear or branched fatty acid residue containing from 1 to 40 carbon atoms, and R2 represents a hydrocarbon-based chain that is especially branched, containing from 1 to 40 carbon atoms provided that R1+R2≥10. The esters may be chosen especially from esters of alcohol and of fatty acid, for instance cetostearyl octanoate, esters of isopropyl alcohol, such as isopropyl myristate, isopropyl palmitate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic acid esters, for instance isodecyl neopentanoate, isotridecyl neopentanoate, and isononanoic acid esters, for instance isononyl isononanoate and isotridecyl isononanoate.
- polyol esters and pentaerythritol esters, for instance dipentaerythrityl tetrahydroxystearate/tetraisostearate,
- esters of diol dimers and of diacid dimers, such as Lusplan DD-DA5® and Lusplan DD-DA7® sold by the company Nippon Fine Chemical and described in patent application US 2004-175 338,
- copolymers of a diol dimer and of a diacid dimer and esters thereof, such as dilinoleyl diol dimer/dilinoleic dimer copolymers and esters thereof, for instance Plandool-G,
- copolymers of polyols and of diacid dimers, and esters thereof, such as Hailuscent ISDA or the dilinoleic acid/butanediol copolymer,
- fatty alcohols that are liquid at room temperature, with a branched and/or unsaturated carbon-based chain containing from 12 to 26 carbon atoms, for instance 2-octyldodecanol, isostearyl alcohol and oleyl alcohol,
- C12-C22 higher fatty acids, such as oleic acid, linoleic acid or linolenic acid, and mixtures thereof,
- dialkyl carbonates, the two alkyl chains possibly being identical or different, such as dicaprylyl carbonate sold under the name Cetiol CC® by Cognis,
- oils of high molar mass, in particular with a molar mass ranging from about 400 to about 2000 g/mol and in particular from about 650 to about 1600 g/mol. As oils of high molar mass that may be used in the present invention, mention may be made especially of linear fatty acid esters with a total carbon number ranging from 35 to 70, for instance pentaerythrityl tetrapelargonate, hydroxylated esters, such as polyglyceryl-2 triisostearate, aromatic esters, such as tridecyl trimellitate, esters of branched C24-C28 fatty alcohols or fatty acids, such as those described in patent U.S. Pat. No. 6,491,927, and pentaerythritol esters, and especially triisoarachidyl citrate, glyceryl triisostearate, glyceryl tris(2-decyl)tetradecanoate, polyglyceryl-2 tetraisostearate or pentaerythrityl tetrakis(2-decyl)tetradecanoate; phenyl silicones, such as Belsil PDM 1000 from the company Wacker (MM=9000 g/mol), non-volatile polydimethylsiloxanes (PDMS), PDMSs comprising alkyl or alkoxy groups that are pendent and/or at the end of the silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, dimethicones or phenyl trimethicones with a viscosity of less than or equal to 100 cSt, and mixtures thereof, and also mixtures of these various oils, and mixtures thereof.

According to one embodiment, the composition of the invention comprises at least one non-volatile oil chosen from non-volatile hydrocarbon-based oils such as:

hydrocarbon-based oils of animal origin;

hydrocarbon-based oils of plant origin;

synthetic ethers containing from 10 to 40 carbon atoms;

synthetic esters, for instance oils of formula R1COOR2, in which R1 represents a linear or branched fatty acid residue containing from 1 to 40 carbon atoms, and R2 represents a hydrocarbon-based chain that is especially branched, containing from 1 to 40 carbon atoms provided that $R1+R2\geq10$;

polyol esters and pentaerythritol esters;

fatty alcohols that are liquid at room temperature, with a branched and/or unsaturated carbon-based chain containing from 12 to 26 carbon atoms;

dialkyl carbonates, the two alkyl chains possibly being identical or different;

oils of high molar mass; and mixtures thereof.

Advantageously, a liquid fatty phase of the invention may comprise at least 40% by weight, preferably at least 60% by weight or even 100% by weight of non-volatile oil(s) relative to the total weight of the said liquid fatty phase.

Additional Ingredients of the Compositions

Compositions according to the present invention may also comprise at least one additional ingredient like some additional pulverulent phase materials besides the microcapsules defined above.

For the purposes of the present invention, this pulverulent phase may comprise, besides the microcapsules required according to the invention, at least one non-encapsulated particulate material chosen from fillers; pigments; nacres; particles with a metallic tint; and mixtures thereof.

Obviously these additional ingredients are used in appropriate amounts and conditions in order not to be detrimental to the compositions.

The following ranges preferably take into consideration the amount of microcapules within the amount of pulverulent phase given here-below. A composition according to the invention may comprise at least 1% by weight and more particularly at least 5% by weight of pulverulent phase relative to the total weight of the said composition.

More particularly, a composition according to the invention may comprise at least 15% by weight and more particularly at least 20% by weight of pulverulent phase relative to the total weight of the said composition.

Thus, a composition according to the invention advantageously may comprise from 1% to 70% by weight, preferably from 5% to 60% by weight and better still from 10% to 50% by weight of pulverulent phase relative to the total weight of the said composition.

Thus, a composition according to the invention advantageously may comprise from 15% to 70% by weight, preferably from 20% to 60% by weight and better still from 25% to 50% by weight of pulverulent phase relative to the total weight of the said composition.

Silicone Elastomers

One or several silicone elastomers (non-encapsulated) may additionally be present in the compositions of the present invention in an amount of from 0.1% to 30% by weight, more preferably from 0.5% to 25% by weight, more preferably from 1% to 20%, more preferably from 1% to 15% and even more preferably from 3% to 10% by weight based on the weight of the composition.

Any suitable silicone elastomer can be used in accordance with the present invention. Suitable silicone elastomers include, for example, emulsifying silicone elastomers such as polyglycerolated and/or hydrophilic emulsifying silicone elastomers such as alkoxylated silicone elastomers, and non-emulsifying silicone elastomers. Such silicone elastomers can be spherical or non-spherical.

Polyglycerolated Silicone Elastomers

Suitable polyglycerolated silicone elastomers include, for example, crosslinked elastomeric organopolysiloxanes that may be obtained by a crosslinking addition reaction of diorganopolysiloxane containing at least one hydrogen atom linked to silicon and of polyglycerolated compounds containing ethylenically unsaturated groups, especially in the presence of a platinum catalyst.

Polyglycerolated silicone elastomers that may be used include, but are not limited to, those sold under the names "KSG-710", "KSG-810", "KSG-820", "KSG-830" and "KSG-840" by the company Shin-Etsu. Suitable polygycerolated silicone elastomers are also disclosed in U.S. Ser. No. 11/085,509, filed Mar. 22, 2005 (published as U.S. patent application publication no. 2005/0220728), the entire disclosure of which is hereby incorporated by reference.

Hydrophilic Emulsifying Silicone Elastomers

The term "hydrophilic emulsifying silicone elastomer" means a silicone elastomer comprising at least one hydrophilic chain other than a polyglycerolated chain as described above.

In particular, the hydrophilic emulsifying silicone elastomer may be chosen from polyoxyalkylenated silicone elastomers.

Suitable polyoxyalkylenated elastomers are described in patents U.S. Pat. Nos. 5,236,986, 5,412,004, 5,837,793 and 5,811,487.

Suitable polyoxyalkylenated silicone elastomers that may be used include those sold under the names "KSG-21", "KSG-20", "KSG-30", "KSG-31", "KSG-32", "KSG-33", "KSG-210", "KSG-310", "KSG-320", "KSG-330", "KSG-340" and "X-226146" by the company Shin-Etsu, or "DC9010" and "DC9011" by the company Dow Corning.

Suitable hydrophilic emulsifying silicone elastomers are also disclosed in U.S. Ser. No. 11/085,509, filed Mar. 22, 2005 (published as U.S. patent application publication no. 2005/0220728).

Non-Emulsifying Silicone Elastomers

The term "non-emulsifying" defines elastomers not containing a hydrophilic chain, such as polyoxyalkylene or polyglycerolated units.

The non-emulsifying silicone elastomer is preferably an elastomeric crosslinked organopolysiloxane that may be obtained by a crosslinking addition reaction of diorganopolysiloxane containing at least one hydrogen linked to silicon and of diorganopolysiloxane containing ethylenically unsaturated groups linked to silicon, especially in the presence of a platinum catalyst; or by dehydrogenation crosslinking coupling reaction between a diorganopolysiloxane containing hydroxyl end groups and a diorganopolysiloxane containing at least one hydrogen linked to silicon, especially in the presence of an organotin compound; or by a crosslinking coupling reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Suitable non-emulsifying silicone elastomers are described in patent applications JP61-194009 A, EP0242219 A, EP0295886 A and EP0765656 A.

Suitable non-emulsifying silicone elastomers that may be used include, but are not limited to, those sold under the names “DC 9040”, “DC 9041”, “DC 9509”, “DC 9505” and “DC 9506” by the company Dow Corning.

Mention should also be made of DC 9701 a spherical silicone elastomer powder coated with silica (INCI name: dimethicone/vinyl dimethicone cross-polymer (and) silica) and DC EP 9261Ti an elastomer powder coated with titanium dioxide.

Suitable non-emulsifying silicone elastomers are also disclosed in U.S. Ser. No. 11/085,509, filed Mar. 22, 2005 (published as U.S. patent application publication no. 2005/0220728).

The non-emulsifying silicone elastomer may also be in the form of elastomeric crosslinked organopolysiloxane powder coated with silicone resin, especially with silsesquioxane resin, as described, for example, in patent U.S. Pat. No. 5,538,793, the entire content of which is herein incorporated by reference. Such elastomers are sold under the names “KSP-100”, “KSP-101”, “KSP-102”, “KSP-103”, “KSP-104” and “KSP-105” by the company Shin-Etsu.

Other elastomeric crosslinked organopolysiloxanes in the form of powders include hybrid silicone powders functionalized with fluoroalkyl groups, sold especially under the name “KSP-200” by the company Shin-Etsu; hybrid silicone powders functionalized with phenyl groups, sold especially under the name “KSP-300” by the company Shin-Etsu.

Mention should also be made of the following hybrid silicone powders “KSP-441” and “KSP-411” by the company Shin-Etsu. INCI names of “KSP-441” and “KSP-411” are respectively Polysilicone-22 and Polysilicone-1 Crosspolymer.

Film-Forming Agents

Silicone Polyamide

The compositions according to the invention comprise at least one silicone polyamide.

The silicone polyamides of the composition are preferably solid at room temperature (25° C.) and atmospheric pressure (760 mmHg).

The silicone polyamides of the composition of the invention may be polymers of the polyorganosiloxane type, for instance those described in documents U.S. Pat. Nos. 5,874,069, 5,919,441, 6,051,216 and 5,981,680. According to the invention, the silicone polymers may belong to the following two families:

(1) polyorganosiloxanes comprising at least two amide groups, these two groups being located in the polymer chain, and/or (2) polyorganosiloxanes comprising at least two amide groups, these two groups being located on grafts or branches.

A) According to a first variant, the silicone polymers are polyorganosiloxanes as defined above in which the amide units are located in the polymer chain.

The silicone polyamides may be more particularly polymers comprising at least one unit corresponding to the general formula I:

(I)

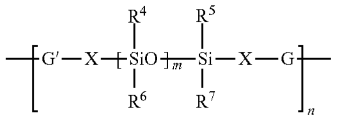

1) in which: G' represents C(O) when G represents —C(O)—NH—Y—NH—, and G' represents —NH— when G represents —NH—C(O)—Y—C(O)—, 2) $R^4$, $R^5$, $R^6$ and $R^7$, which may be identical or different, represent a group chosen from:

- linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms,
- C6-C10 aryl groups, optionally substituted with one or more C1-C4 alkyl groups,
- polyorganosiloxane chains possibly containing one or more oxygen, sulfur and/or nitrogen atoms, 3) the groups X, which may be identical or different, represent a linear or branched C1 to C30 alkylenediyl group, possibly containing in its chain one or more oxygen and/or nitrogen atoms;

4) Y is a saturated or unsaturated C1 to C50 linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, C3 to C8 cycloalkyl, C1 to C40 alkyl, C5 to C10 aryl, phenyl optionally substituted with one to three C1 to C3 alkyl, C1 to C3 hydroxyalkyl and C1 to C6 aminoalkyl groups, or 5) Y represents a group corresponding to the formula:

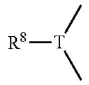

in which:

- T represents a linear or branched, saturated or unsaturated, C3 to C24 trivalent or tetravalent hydrocarbon-based group optionally substituted with a polyorganosiloxane chain, and possibly containing one or more atoms chosen from O, N and S, or T represents a trivalent atom chosen from N, P and Al, and
- R8 represents a linear or branched C1-C50 alkyl group or a polyorganosiloxane chain, possibly comprising one or more ester, amide, urethane, thiocarbamate, urea, thiourea and/or sulfonamide groups, which may possibly be linked to another chain of the polymer, 6) n is an integer ranging from 2 to 500 and preferably from 2 to 200, and m is an integer ranging from 1 to 1000, preferably from 1 to 700 and better still from 6 to 200.

According to the invention, 80% of the groups $R^4$, $R^5$, $R^6$ and $R^7$ of the polymer are preferably chosen from methyl, ethyl, phenyl and 3,3,3-trifluoropropyl groups. According to another embodiment, 80% of the groups $R^4$, $R^5$, $R^6$ and $R^7$ of the polymer are methyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) branched C30 to $C_{56}$ alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

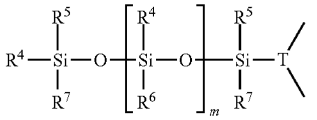

or

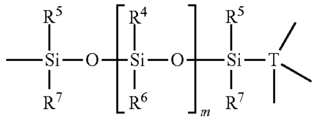

in which $R^4$, $R^5$, $R^6$, $R^7$, T and m are as defined above.

B) According to the second variant, the silicone polyamides may be polymers comprising at least one unit corresponding to formula (II):

(II)

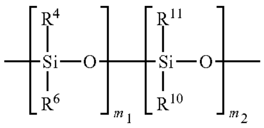

in which:

R4 and R6, which may be identical or different, are as defined above for formula (I), R10 represents a group as defined above for R4 and R6, or represents a group of formula —X-G"-R12 in which X is as defined above for formula (I) and R12 represents a hydrogen atom or a linear, branched or cyclic, saturated or unsaturated, C1-C50 hydrocarbon-based group optionally comprising in its chain one or more atoms chosen from O, S and N, optionally substituted with one or more fluorine atoms and/or one or more hydroxyl groups, or a phenyl group optionally substituted with one or more C1-C4 alkyl groups, and G" represents —C(O)NH— and —HN—C(O)—, R11 represents a group of formula —X-G"-R12 in which X, G" and R12 are as defined above, m1 is an integer ranging from 1 to 998, and m2 is an integer ranging from 2 to 500.

According to the invention, the silicone polymer may be a homopolymer, i.e. a polymer comprising several identical units, in particular units of formula (I) or of formula (II).

According to the invention, it is also possible to use a silicone polymer formed from a copolymer comprising several different units of formula (I), i.e. a polymer in which at least one of the groups $R^4$, $R^5$, $R^6$, $R^7$, X, G, Y, m and n is different in one of the units. The copolymer may also be formed from several units of formula (II), in which at least one of the groups $R^4$, $R^6$, $R^{10}$, $R^{11}$, $m_1$ and $m_2$ is different in at least one of the units.

It is also possible to use a polymer comprising at least one unit of formula (I) and at least one unit of formula (II), the units of formula (I) and the units of formula (II) possibly being identical to or different from each other.

These copolymers may be block polymers or grafted polymers.

In this first embodiment of the invention, the silicone polymer may also consist of a grafted copolymer. Thus, the polyamide containing silicone units may be grafted and optionally crosslinked with silicone chains containing amide groups. Such polymers may be synthesized with trifunctional amines.

According to one advantageous embodiment of the invention, the groups capable of establishing hydrogen interactions are amide groups of formulae —C(O)NH— and —HN—C(O)—. In this case, the structuring agent may be a polymer comprising at least one unit of formula (III) or (IV):

(III)

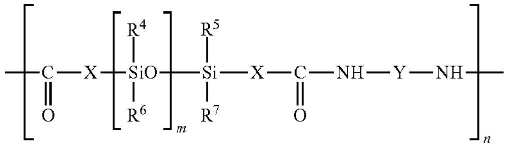

or (IV)

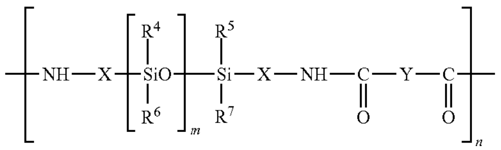

in which $R^4$, $R^5$, $R^6$, $R^7$, X, Y, m and n are as defined above.

In these polyamides of formula (III) or (IV), m is in the range from 1 to 700, in particular from 15 to 500 and especially from 50 to 200, and n is in particular in the range from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following members:

1) 1 to 5 amide, urea, urethane or carbamate groups, 2) a $C_5$ or $C_6$ cycloalkyl group, and 3) a phenylene group optionally substituted with 1 to 3 identical or different $C_1$ to $C_3$ alkyl groups.

In formulae (III) and (IV), the alkylene groups may also be substituted with at least one member chosen from the group consisting of:

a hydroxyl group, a $C_3$ to $C_8$ cycloalkyl group, one to three $C_1$ to $C_{40}$ alkyl groups, a phenyl group optionally substituted with one to three $C_1$ to $C_3$ alkyl groups, a $C_1$ to $C_3$ hydroxyalkyl group, and a $C_1$ to $C_6$ aminoalkyl group.

In these formulae (III) and (IV), Y may also represent:

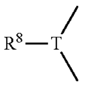

in which $R^8$ represents a polyorganosiloxane chain and T represents a group of formula:

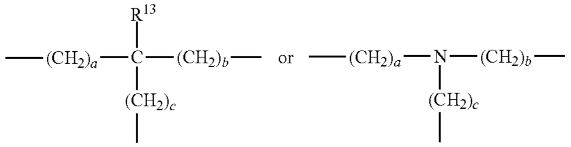

in which a, b and c are, independently, integers ranging from 1 to 10, and $R^{13}$ is a hydrogen atom or a group such as those defined for $R^4$, $R^5$, $R^6$ and $R^7$.

In formulae (III) and (IV), $R^4$, $R^5$, $R^6$ and $R^7$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different units of formula (III) or (IV).

Thus, the polymer may be a polyamide containing several units of formula (III) or (IV) of different lengths, i.e. a polyamide corresponding to formula (V):

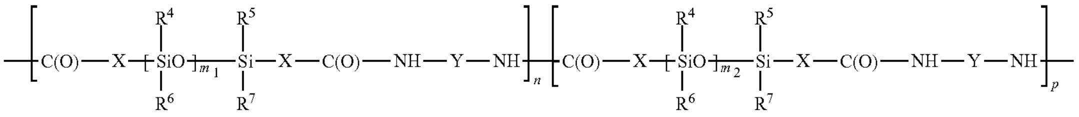

(V)

in which X, Y, n and $R^4$ to $R^7$ have the meanings given above, $m_1$ and $m_2$, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula VI:

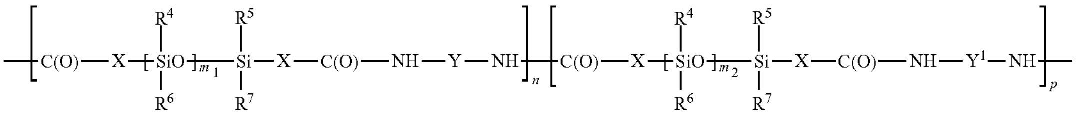

(VI)

in which $R^4$ to $R^7$, X, Y, $m_1$, $m_2$, n and p have the meanings given above and $Y^1$ is different from Y but chosen from the groups defined for Y. As previously, the various units may be structured to form either a block copolymer, or a random copolymer or an alternating copolymer.

In this first embodiment of the invention, the structuring agent may also consist of a grafted copolymer. Thus, the polyamide containing silicone units may be grafted and optionally crosslinked with silicone chains containing amide groups. Such polymers may be synthesized with trifunctional amines.

In this case, the polymer may comprise at least one unit of formula (VII):

(VII)

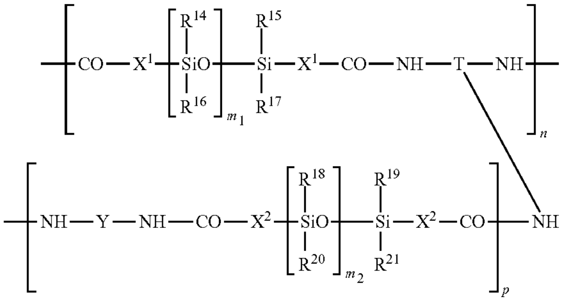

in which $X^1$ and $X^2$, which are identical or different, have the meaning given for X in formula (I), n is as defined in formula (I), Y and T are as defined in formula (I), $R^{14}$ to $R^{21}$ are groups chosen from the same group as $R^4$ to $R^7$, $m_1$ and $m_2$ are numbers in the range from 1 to 1000, and p is an integer ranging from 2 to 500.

In formula (VII), it is preferred that:

p is in the range from 1 to 25 and better still from 1 to 7, $R^{14}$ to $R^{21}$ are methyl groups, T corresponds to one of the following formulae:

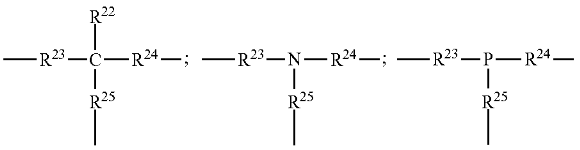

-continued

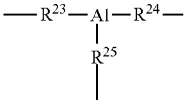

in which $R^{22}$ is a hydrogen atom or a group chosen from the groups defined for $R^4$ to $R^7$, and $R^3$, $R^{24}$ and $R^{25}$ are, independently, linear or branched alkylene groups, and more preferably correspond to the formula:

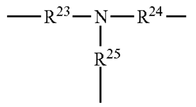

in particular with $R^{23}$, $R^{24}$ and $R^{25}$ representing $—CH_2—CH_2—$, $m_1$ and $m_2$ are in the range from 15 to 500 and better still from 15 to 45, $X^1$ and $X^2$ represent $—(CH_2)_{10}—$, and Y represents $—CH_2—$.

These polyamides containing a grafted silicone unit of formula (VII) may be copolymerized with polyamide-silicones of formula (II) to form block copolymers, alternating copolymers or random copolymers. The weight percentage of grafted silicone units (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to one embodiment variant of the invention, a copolymer of silicone polyamide and of hydrocarbon-based polyamide, or a copolymer comprising units of formula (III) or (IV) and hydrocarbon-based polyamide units, may be used. In this case, the polyamide-silicone units may be located at the ends of the hydrocarbon-based polyamide.

According to one preferred embodiment, the silicone polyamide comprises units of formula III, preferably in which the groups R4, R5, R6 and R7 represent methyl groups, one from among X and Y represents an alkylene group of 6 carbon atoms and the other represents an alkylene group of 11 carbon atoms, n representing the degree of polymerization DP of the polymer.

Examples of such silicone polyamides that may be mentioned include the compounds sold by the company Dow Corning under the name DC 2-8179 (DP 100) and DC 2-8178 (DP 15), the INCI name of which is Nylon-611/dimethicone copolymers.

Advantageously, the silicone polyamides are compounds having the INCI name Nylon-611/dimethicone copolymers.

Advantageously, the composition according to the invention comprises at least one polydimethylsiloxane block polymer of general formula (I) with an index m of about 100. The index "m" corresponds to the degree of polymerization of the silicone part of the polymer.

More preferably, the composition according to the invention comprises at least one polymer comprising at least one unit of formula (III) in which m ranges from 50 to 200, in particular from 75 to 150 and is more particularly about 100.

Preferably also, $R^4$, $R^5$, $R^6$ and $R^7$ independently represent, in formula (III), a linear or branched $C_1$-$C_{40}$ alkyl group, preferably a $CH_3$, $C_2H_5$, n-$C_3H_7$ or isopropyl group.

As examples of polymers that may be used, mention may be made of one of the silicone polyamides obtained in accordance with Examples 1 to 3 of document U.S. Pat. No. 5,981,680.

Preferably, the nylon-611/dimethicone copolymer sold under the reference DC 2-8179 by Dow Corning is used as silicone polyamide.

The silicone polyamide may be present in the composition in a total content ranging from 0.5% to 45% by weight relative to the total weight of the composition, preferably ranging from 1% to 30% by weight and better still ranging from 2% to 20% by weight relative to the total weight of said composition.

Silicone Resin

Examples of these silicone resins that may be mentioned include:

siloxysilicates, which may be trimethylsiloxysilicates of formula $[(CH_3)_3SiO]_x(SiO_{4/2})_y$ (units MQ) in which x and y are integers ranging from 50 to 80, polysilsesquioxanes of formula $(CH_3SiO_{3/2})_x$ (units T) in which x is greater than 100 and at least one of the methyl radicals of which may be substituted with a group R as defined above, polymethylsilsesquioxanes, which are polysilsesquioxanes in which none of the methyl radicals is substituted with another group. Such polymethylsilsesquioxanes are described in document U.S. Pat. No. 5,246,694.

As examples of commercially available polymethylsilsesquioxane resins, mention may be made of those sold:

by the company Wacker under the reference Resin MK, such as Belsil PMS MK: polymer comprising CH3SiO3/2 repeating units (units T), which may also comprise up to 1% by weight of (CH3)2SiO2/2 units (units D) and having an average molecular weight of about 10 000 g/mol, or by the company Shin-Etsu under the reference KR-220L, which are composed of units T of formula CH3SiO3/2 and contain Si—OH (silanol) end groups, under the reference KR-242A, which comprise 98% of units T and 2% of dimethyl units D and contain Si—OH end groups, or under the reference KR-251, comprising 88% of units T and 12% of dimethyl units D and contain Si—OH end groups.

Siloxysilicate resins that may be mentioned include trimethyl siloxysilicate resins (TMS) optionally in the form of powders. Such resins are sold under the reference SR1000 by the company Momentive Performance Materials or under the reference TMS 803 by the company Wacker. Mention may also be made of trimethyl siloxysilicate resins sold in a solvent such as cyclomethicone, sold under the name KF-7312J by the company Shin-Etsu or DC 749 and DC 593 by the company Dow Corning.

Advantageously, the silicone resin, for instance the trimethyl siloxysilicate resin, is present in a content ranging from 0.5% to 30%, or better still from 1% to 25% or even better still from 5% to 25% relative to the total weight of the composition.

Preferably, nylon-611/dimethicone is used as silicone polyamide and a trimethyl siloxysilicate resin is used as silicone resin.

According to another embodiment, the silicone resins are propylphenylsilsesquioxane resins.

Silsesquioxane resins are a specific form of film forming silicone resins. Silicone resins are crosslinked organopolysiloxanes which are solid at room temperature and generally soluble in organic solvents. When they are soluble in volatile solvents, silicone resins are capable of forming a film once the solvent has evaporated. Furthermore, if the solvent dissolving the silicone resin is absorbed on the substrate onto which it is applied, the silicone resin which remains on the substrate may also form a film.

The compositions of the present invention may comprise propylphenylsilsesquioxane resins, which have been disclosed in patent publications WO2005/090444, published on Sep. 29, 2005; US20040180011, published on Sep. 16, 2004; and US20040156806, published on Aug. 12, 2004.

The propylphenylsilsesquioxane resin comprises at least about 70 mole % of propyl siloxy units ($C_3H_7SiO_{3/2}$), based on the total mole % siloxy units of the resin, and at most about mole % of phenyl siloxy units ($C_6H_5SiO_{3/2}$), based on the total mole % siloxy units of the resin.

The mole % of propyl siloxy units to phenyl siloxy units can be adjusted depending on an intended application. As such, it is possible to have propylphenylsilsesquioxane resins having a mole % propyl siloxy units:phenyl siloxy units ranging from about 70:30 to about 100:0, such as 70:30; 80:20; 90:10; and 100:0; and subranges therebetween. When the mole % of the propyl siloxy units is about 100 mole %, the propylphenylsilsesquioxane resin is referred to as a propylsilsesquioxane resin.

A suitable example of a propylphenylsilsesquioxane resin for use in cosmetic compositions of the present invention includes, but is not limited to, a propylsilsesquioxane resin commercially available from Dow-Corning under the tradename DC 670 Fluid.

The propylphenylsilsesquioxane film forming resin may be present in an amount ranging from about 0.5% to about 50% by weight, such as from about 1% to about 40% by weight, such as from about 2% to about 30% by weight, such as from about 3% to about 20% by weight, and such as from about 4% to about 10% by weight, all weights based on the weight of the composition as a whole.

Silicone Acrylate Copolymers

The composition of the present invention may contain silicone acrylate copolymers.

Silicone acrylate copolymers are another specific form of film forming silicone resins. They are available as silicone acrylate copolymers with a (meth)acrylate backbone grafted with a silicone chain or as a silicone backbone grafted with a (meth)acrylate, or as a silicone acrylate dendrimer.

Silicone acrylate dendrimers, such as those described and claimed in U.S. Pat. No. 6,280,748, the entire contents of which is hereby incorporated by reference, are preferred for use in the composition of the present invention. The silicone acrylate dendrimer is comprised of a vinyl polymer having a carbosiloxane dendrimer structure in its side molecular chain. It is characterized by a vinyl-type polymer which has in its side molecular chain a carbosiloxane dendrimer structure. The term "carbosiloxane dendrimer structure" is a structure with high-molecular-weight groups branched with high regularity in a radial direction from a single core.

The vinyl polymer backbone is formed from a vinyl-type monomer which contains a radical polymerizable vinyl group. In its broadest definition, there are no particular limitations with regards to the type of such a monomer. A particularly preferred vinyl polymer is a (meth)acrylate.

The number-average molecular weight of the silicone acrylate dendrimers for use in the composition of the present invention ranges from about 3,000 to about 2,000,000, such as from about 5,000 to about 800,000.

Particularly preferred silicone acrylate dendrimers for use in the composition of the present invention are available from Dow Corning as FA-4001 CM silicone acrylate, a 30% solution in cyclomethicone, and as FA-4002 ID silicone acrylate, a 40% solution in isododecane, under the INCI name of Acrylates/Polytrimethylsiloxymethacrylate Copolymer.

The silicone acrylate copolymer may be present in the composition of the invention in an amount ranging from about 0.5% to about 20% by weight, such as from about 0.7% to about 15% by weight, such as from about 1% to about 10% by weight, all weights based on the weight of the composition as a whole.

Pulverulent Material

Compositions according to the present invention may also comprise at least one non-encapsulated reflective particle.

The total reflective particle content that is encapsulated and non-encapsulated reflective particle content preferably ranges from 0.1% to 95% by weight, preferably from 0.1% to 75% by weight, more preferably from 0.1 to 50% by weight, more preferably from 0.1% to 40% by weight based on the weight of the composition.

Advantageously, the composition according to the invention contains less than 1%, preferably less than 0.5% of non-encapsulated reflective particle; preferably, the composition is devoid of any non-encapsulated reflective particle.

a) Filler

For the purposes of the present invention, the term "fillers" should be understood as meaning colourless or white solid particles of any form, which are in an insoluble and dispersed form in the medium of the composition.

These fillers, of mineral or organic, natural or synthetic nature, give the composition containing them softness and give the makeup result a matt effect and uniformity.

A composition according to the invention may comprise from 0.5% to 50% by weight and preferably from 1% to 30% by weight of fillers relative to the total weight of the said composition.

This amount of fillers does not include the amount of hollow particles required in parallel according to the invention.

Among the mineral fillers that may be used in the compositions according to the invention, mention may be made of natural or synthetic mica, talc, kaolin, natural or synthetic sericite, silica, hydroxyapatite, boron nitride, calcium carbonate, hollow silica microspheres (Silica beads from Maprecos), glass or ceramic microcapsules; composites of silica and titanium dioxide, such as the TSG series sold by Nippon Sheet Glass, and mixtures thereof.

Among the organic fillers that may be used in the compositions according to the invention, mention may be made of polyamide powders (Nylon® Orgasol from Atochem), poly-β-alanine powder and polyethylene powder, polytetrafluoroethylene (Teflon®) powder, lauroyllysine, tetrafluoroethylene polymer powders, spherical powders of crosslinked elastomeric organopolysiloxane, described especially in document JP-A-02-243612, such as those sold under the name Trefil Powder E 2-506C or DC9506 or DC9701 by the company Dow Corning, silicone resins, which are products of hydrolysis and polycondensation of siloxane mixtures of formulae (R)3SiOHCH3 and Si(OCH3)4, R representing an alkyl group containing from 1 to 6 carbon atoms (for example KSP100 from Shin-Etsu), silicone resin microbeads (for example Tospearl® from Toshiba), Polypore® L200 (Chemdal Corporation), polyurethane powders, in particular crosslinked polyurethane powders comprising a copolymer, the said copolymer comprising trimethylol hexyl lactone, for instance the polymer of hexamethylene diisocyanate/trimethylol hexyl lactone, sold under the name Plastic powder D-400@ or Plastic Powder D-800® by the company Toshiki, and mixtures thereof.

Among the other organic fillers that may be used in the compositions according to the invention, mention may be made of starch-based or cellulose-based powders. Examples of such fillers that may be mentioned include the Dry Flo products sold by Akzo Nobel and the Cellubeads products sold by the company Daito Kasei.

Advantageously, the fillers in accordance with the invention are mineral fillers, preferably chosen from mica, sericite, kaolin, talc and silica, and mixtures thereof.

b) Particulate Materials for Colouring Purposes.

These additional colouring particulate materials may be present in a proportion of from 0 to 40% by weight, preferably from 1% to 30% by weight or even 5% to 30% by weight relative to the total weight of the composition containing them.

They may especially be pigments, nacres and/or particles with metallic tint products, these materials possibly being surface-treated.

The term “pigments” should be understood as meaning white or coloured, mineral or organic particles that are insoluble in an aqueous solution, which are intended to colour and/or opacify the composition containing them.

A composition according to the invention may comprise from 0.01% to 40% by weight, preferably from 0.1% to 20% by weight and better still from 1% to 15% by weight of pigments relative to the total weight of said composition.

The pigments may be white or coloured, and mineral and/or organic.

As mineral pigments that may be used in the invention, mention may be made of titanium oxide, titanium dioxide, zirconium oxide, zirconium dioxide, cobalt oxides, nickel oxides, tin oxides, zinc oxides, cerium oxide or cerium dioxide and also zinc oxide, aluminium, oxide, iron oxide or chromium oxide, ferric blue, manganese violet, ultramarine blue and chromium hydrate, and mixtures thereof.

According to a specific embodiment, the composition of the invention contain at least inorganic pigments chosen from titanium dioxide, zinc oxide, cerium oxide, and/or fillers chosen from bismuth oxychloride or boron nitride, in order to improve the white color of the composition.

According to a specific embodiment, the compositions of the invention contain at least $TiO_2$.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is the product sold by the company Miyoshi under the reference PC Ball PC-LL-100 P, this pigment being constituted of silica microspheres containing yellow iron oxide.

Advantageously, the pigments in accordance with the invention are iron oxides and/or titanium dioxides.

The term “nacres” should be understood as meaning iridescent or non-iridescent coloured particles of any shape, especially produced by certain molluscs in their shell or alternatively synthesized, which have a colour effect via optical interference.

A composition of the invention may comprise from 1% to 80% by weight, preferably from 5% to 60% by weight and better still from 100% to 40% by weight of nacres relative to the total weight of said composition.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery colour or tint.

As illustrations of nacres that may be used in the context of the present invention, mention may be made of gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company Engelhard under the name Super bronze (Cloisonne); the orange nacres sold especially by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold especially by the company Engelhard under the names Nuantique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red-tinted nacres with a golden tint sold especially by the company Engelhard under the name Sunstone G012 (Gemtone); the pink nacres sold especially by the company Engelhard under the name Tan opale 0005 (Gemtone); the black nacres with a golden tint sold especially by the company Engelhard under the name Nu antique bronze 240 AB (Timica); the blue nacres sold especially by the company Merck under the name Matte blue (17433) (Microna); the white nacres with a silvery tint sold especially by the company Merck under the name Xirona Silver; and the golden-green pinkish-orange nacres sold especially by the company Merck under the name Indian summer (Xirona), and mixtures thereof.

Advantageously, the nacres in accordance with the invention are micas coated with titanium dioxide or with iron oxide, and also bismuth oxychloride.

The term “particles with a metallic tint”, within the meaning of the present invention, denotes particles whose nature, size, structure and surface state allow them to reflect the incident light, especially in a non-iridescent manner.

A composition according to the invention may comprise from 1% to 50% by weight and preferably from 1% to 20% by weight of particles with a metallic tint relative to the total weight of said composition.

Particles with a substantially flat outer surface are also suitable, since they can, if their size, structure and surface state allow it, more easily give rise to a strong specular reflection, which may then be termed a mirror effect.

The particles with a metallic tint that may be used in the invention may, for example, reflect light in all the components of the visible region without significantly absorbing one or more wavelengths. The spectral reflectance of these particles may, for example, be greater than 70% and better still at least 80%, or even 90% or 95%, in the range 400-700 nm.

These particles generally have a thickness of less than or equal to 1 μm, especially less than or equal to 0.7 μm and in particular less than or equal to 0.5 μm.

The particles with a metallic tint that may be used in the invention are in particular chosen from:

- particles of at least one metal and/or of at least one metal derivative,
- particles comprising a monomaterial or multimaterial organic or mineral substrate, at least partially coated with at least one layer with a metallic tint comprising at least one metal and/or at least one metal derivative, and
- mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulfides.

Among the metal derivatives that may be present in said particles, mention may be made especially of metal oxides, for instance titanium oxide, especially $TiO_2$, iron oxide, especially $Fe_2O_3$, tin oxide, chromium oxide, barium sulfate and the following compounds: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$, and mixtures or alloys thereof.

Illustrations of these particles that may be mentioned include aluminum particles, such as those sold under the names Starbrite 1200 EAC® by the company Siberline and Metalure® by the company Eckart.

Mention may also be made of metal powders of copper or of alloy mixtures such as the references 2844 sold by the company Radium Bronze, metallic pigments, for instance aluminum or bronze, such as those sold under the names Rotosafe 700 from the company Eckart, silica-coated aluminum particles sold under the name Visionaire Bright Silver from the company Eckart, and metal alloy particles, for instance the silica-coated bronze (alloy of copper and zinc) powders sold under the name Visionaire Bright Natural Gold from the company Eckart.

As illustrations of particles of this second type, mention may be made more particularly of:

Glass particles coated with a metallic layer, especially those described in documents JP-A-09188830, JP-A-10158450, JP-A-10158541, JP-A-07258460 and JP-A-05017710.

As illustrations of these particles comprising a glass substrate, mention may be made of those coated, respectively, with silver, gold or titanium, in the form of platelets, sold by the company Nippon Sheet Glass under the name Microglass Metashine. Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company. Those coated either with brown iron oxide or with titanium oxide, tin oxide or a mixture thereof, for instance those sold under the name Reflecks by the company Engelhard or those sold under the name Metashine MC 2080GP by the company Nippon Sheet Glass.

These metal-coated glass particles may be coated with silica, for instance those sold under the name Metashine series PSS1 or GPS1 by the company Nippon Sheet Glass.

Particles comprising a spherical glass substrate optionally coated with a metal, especially those sold under the name Prizmalite Microsphere by the company Prizmalite Industries.

Pigments of the Metashine 1080R range sold by the company Nippon Sheet Glass Co. Ltd are also suitable for the invention. These pigments, more particularly described in patent application JP 2001-11340, are C-Glass glass flakes comprising 65% to 72% $SiO_2$, coated with a layer of titanium oxide of rutile type ($TiO_2$). These glass flakes have a mean thickness of 1 micron and a mean size of 80 microns, i.e. a mean size/mean thickness ratio of 80. They have blue, green or yellow tints or a silver shade depending on the thickness of the $TiO_2$ layer.

Particles comprising a silver-coated borosilicate substrate, are also known as "white nacres".

Particles comprising a metal substrate such as aluminum, copper or bronze, in the form of platelets, are sold under the trade name Starbrite by the company Silberline and under the name Visionaire by the company Eckart.

Particles comprising a synthetic mica substrate coated with titanium dioxide, and for example particles with a size of between 80 and 100 μm, comprising a synthetic mica (fluorophlogopite) substrate coated with titanium dioxide representing 12% of the total weight of the particle, sold under the name Prominence by the company Nihon Koken.

The particles with a metallic tint may also be chosen from particles formed from a stack of at least two layers with different refractive indices. These layers may be of polymeric or metallic nature and may especially include at least one polymer layer.

Thus, the particles with a metallic effect may be particles derived from a multilayer polymer film.

The choice of materials intended to constitute the various layers of the multilayer structure is obviously made so as to give the particles thus formed the desired metallic effect.

Such particles are especially described in WO 99/36477, U.S. Pat. Nos. 6,299,979 and 6,387,498 and more particularly identified below in the goniochromatic section.

Advantageously, the particles with a metallic tint in accordance with the invention are particles with a spherical or non-spherical glass substrate, and also particles with a metallic substrate.

According to a specific embodiment, a composition according to the invention contains at least reflective particles in particular selected the nacres, particles with a metallic tint, and bismuth oxichloride and their mixtures.

As illustrations of particles of this second type, mention may be made more particularly of:

- Particles comprising a synthetic mica substrate coated with titanium dioxide coated or particles comprising a spherical glass substrate optionally coated with either with brown iron oxide or with titanium oxide, tin oxide or a mixture thereof, for instance those sold under the name Reflecks by the company Engelhard or those sold under the name Metashine MC 2080GP by the company Nippon Sheet Glass. Such particles are detailed in JP-A-09188830, JP-A-10158450, JP-A-10158541, JP-A-07258460 and JP-A-05017710.

- Particles with metallic effect comprising mineral substrate coated with a metal. It may be a particles having a silver-coated borosilicate substrate, are also known as "white nacres.
- Particles comprising a spherical glass substrate coated with silver, especially those sold under the name MICROGLASS METASHINE REFSX 2025 PS by TOYAL. Particles comprising a spherical glass substrate coated with nickel/chrome/molybdene alloy especially those sold under the name CRYSTAL STAR GF 550, GF 2525 by the same company.
- Particles having metallic effect and having on surface a metallic compound optionally coated particles sold under the names METASHINE® LE 2040 PS, METASHINE® 5 MC5090 PS or METASHINE® MC280GP (2523) by the company NIPPON SHEET GLASS, SPHERICAL SILVER POWDER® DC 100, SILVER FLAKE® JV 6 or GOLD POWDER® A1570 by the company ENGELHARD, STARLIGHT REFLECTIONS FXM® by the company ENERGY STRATEGY ASSOCIATES INC, BRIGHT SILVER® 1 E 0.008X0.008 by the company MEADOWBROOK INVENTIONS, ULTRAMIN® (ALUMINUM POUDRE FINE LIVING), and COSMETIC METALLIC POWDER VISIONNAIRE BRIGHT SILVER SEA®, COSMETIC METALLIC POWDER VISIONAIRE NATURAL GOLD® (60314) or COSMETIC METALLC POWDER VISIONAIRE HONEY® 560316° by the company ECKART.

More preferably, these reflective particles are chosen in the group consisting of bismuth oxichloride particles, mica particles coated with titanium oxide, and mixtures thereof.

According to a specific embodiment, a composition of the invention contains at least bismuth oxichloride (CI 77163).

Advantageously, a composition of the invention may also contains at least nacres comprising a silver-coated borosilicate substrate, are also known as "white nacres". Such particles are sold by the firm MERCK under the tradename Xirona Silver.

The composition may comprise reflective particles predispersed in one oil selected from mineral, vegetable oils and ester oils.

According to a preferred embodiment, these reflective particles are present in the compositions of the invention under a pre-dispersed form in at least one oil selected in the group consisting of

- Mineral oils
- Vegetable oils like sweet almond oil, wheat germ oil, jojoba oil, apricot oil, soybean oil, canola oil, castor oil
- Esters such as octyl dodecanol, octyldodecyl neopentanoate, caprylic/capric triglycerides, pentaerythrityl tetraisostearate, isodecyl neopentanoate, diisopropyl sebacate, $C_{12}$-$C_{15}$ alkyl benzoate, ethylhexyl ethylhexanoate, ethylhexyl hydroxystearate,
- and mixture thereof.

More preferably, the oil is chosen in the group consisting of ethyl (2) hexyl hydroxystearate, or castor oil, and preferably ethyl (2) hexyl hydroxystearate.

Thus, according to a specific and preferred embodiment, a composition of the invention comprises, in a physiologically acceptable medium,

- (i) at least microcapsules of the invention and
- (ii) at least reflective particles under a pre-dispersed form in at least one oil selected in the group consisting of ethyl (2) hexyl hydroxystearate or castor oil and preferably ethyl (2) hexyl hydroxystearate.

Advantageously, the reflective particles are chosen among bismuth oxichloride particles and mica particles covered with titanium oxide, said particles being pre-dispersed ethyl (2) hexylhydroxystearate.

According to a specific embodiment, the composition of the invention comprises a pre-dispersion comprising from 68% to 72% by weight of bismuth oxichloride in 28% to 32% by weight of ethyl (2) hexylhydroxystearate, with respect to the total weight of the pre-dispersion i.e a weight ratio bismuth oxichloride/oil(s) greater or equal to 2, and preferably ranging from 2 to 2.6.

Such a dispersion is sold by the firm MERCK under the tradename Xirona Silver Biron® Liquid Silver.

The present compositions may also comprise at least one microcapsule comprising at least one encapsulated colorant as the microcapsule described in WO 2009/138978 A2 filed by Tagra Biotechnologies Ltd or WO 2013/107350 filed by L'OREAL.

Colorant(s)

Additional coloured material may be any organic or inorganic colorant approved for use in cosmetics by CTFA and the FDA used in cosmetic formulations.

Thus the term "colorant" refers to organic pigments such as synthetic or natural dyes selected from any of the well known FD&C or D&C dyes, to inorganic pigments such as metal oxides, or lakes such as the ones based on cochineal carmine, barium, strontium, calcium or aluminum and any combination (blend) thereof. Such colorants are detailed here-after.

In a particular embodiment, the colorant may be water-soluble or water-dispersible.

In another embodiment, the colorant useful according to the present invention may be oil-soluble or oil-dispersible or with limited solubility in water.

The compositions may also contain lakes corresponding to an organic colorant secured to a substrate. Such (a) lake(s) is (are) advantageously chosen among the here-below material, and their mixture(s):

- carmin of cochineal;
- organic pigments of azoic, anthraquinonic, indigoid, xanthenic, pyrenic, quinolinic, triphenylmethane, fluoran colorants; Among the organic pigments may be cited those known under the following trademark references: D&C Blue no 4, D&C Brown no 1, D&C Green no 5, D&C Green no 6, D&C Orange no 4, D&C Orange no 5, D&C Orange no 10, D&C Orange no 11, D&C Red no 6, D&C Red no 7, D&C Red no 17, D&C Red no 21, D&C Red no 22, D&C Red no 27, D&C Red no 28, D&C Red no 30, D&C Red no 31, D&C Red no 33, D&C Red no 34, D&C Red no 36, D&C Violet no 2, D&C Yellow no 7, D&C Yellow no 8, D&C Yellow no 10, D&C Yellow no 11, FD&C Blue no 1, FD&C Green no 3, FD&C Red no 40, FD&C Yellow no 5, FD&C Yellow no 6;
- the water-insoluble salts of sodium, potassium, calcium, baryum, aluminum, zirconium, strontium, titanium, of acid colorants such as azoic, anthraquinonic, indigoids, xanthenic, pyrenic, quinolinic, triphenylmethane, fluoran colorants, these colorants may include at least one carboxylic or sulfonic acid group.

The organic lakes may also be protected by an organic support such as rosin or aluminum benzoate.

Among the organic lakes, we may in particular cite those known under the following names: D&C Red no 2 Aluminum lake, D&C Red no 3 Aluminum lake, D&C Red no 4 Aluminum lake, D&C Red no 6 Aluminum lake, D&C Red no 6 Barium lake, D&C Red no 6 Barium/Strontium lake, D&C Red no 6 Strontium lake, D&C Red no 6 Potassium lake, D&C Red no 6 Sodium lake, D&C Red no 7 Aluminum lake, D&C Red no 7 Barium lake, D&C Red no 7 Calcium lake, D&C Red no 7 Calcium/Strontium lake, D&C Red no 7 Zirconium lake, D&C Red no 8 Sodium lake, D&C Red no 9 Aluminum lake, D&C Red no 9 Barium lake, D&C Red no 9 Barium/Strontium lake, D&C Red no 9 Zirconium lake, D&C Red no 10 Sodium lake, D&C Red no 19 Aluminum lake, D&C Red no 19 Barium lake, D&C Red no 19 Zirconium lake, D&C Red no 21 Aluminum lake, D&C Red no 21 Zirconium lake, D&C Red no 22 Aluminum lake, D&C Red no 27 Aluminum lake, D&C Red no 27 Aluminum/Titanium/Zirconium lake, D&C Red no 27 Barium lake, D&C Red no 27 Calcium lake, D&C Red no 27 Zirconium lake, D&C Red no 28 Aluminum lake, D&C Red no 28 Sodium lake D&C Red no 30 lake, D&C Red no 31 Calcium lake, D&C Red no 33 Aluminum lake, D&C Red no 34 Calcium lake, D&C Red no 36 lake, D&C Red no 40 Aluminum lake, D&C Blue no 1 Aluminum lake, D&C Green no 3 Aluminum lake, D&C Orange no 4 Aluminum lake, D&C Orange no 5 Aluminum lake, D&C Orange no 5 Zirconium lake, D&C Orange no 10 Aluminum lake, D&C Orange no 17 Barium lake, D&C Yellow no 5 Aluminum lake, D&C Yellow no 5 Zirconium lake, D&C Yellow no 6 Aluminum lake, D&C Yellow no 7 Zirconium lake, D&C Yellow no 10 Aluminum lake, FD&C Blue no 1 Aluminum lake, FD&C Red no 4 Aluminum lake, FD&C Red no 40 Aluminum lake, FD&C Yellow no 5 Aluminum lake, FD&C Yellow no 6 Aluminum lake.

The chemistry material corresponding to each of these organic colorants previously cited are mentioned in the book called <<International Cosmetic Ingredient Dictionnary and Handbook>>, Edition 1997, pages 371 to 386 and 524 to 528, published by <<The Cosmetic, Toiletry, and Fragrance Association>>, of which the content is hereby incorporated by reference in the present specification.

According to a preferred embodiment, the lake(s) is/are selected from carmin of cochineal and the water-insoluble salts of sodium, potassium, calcium, barium, aluminum, zirconium, strontium, titanium, of acid colorants such as azoic, anthraquinonic, indigoid, xanthenic, pyrenic, quinolinic, triphenylmethane, fluoran colorants, being given that these colorants may include at least one carboxylic or sulfonic acid group, and their mixture.

According to a preferred embodiment, the lake(s) is/are selected from carmin of cochineal and the water-insoluble salts of sodium, calcium, aluminum, and their mixture.

As lake incorporating carmine we may cite the commercial references: CARMIN COVALAC W 3508, CLOISONNE RED 424C et CHROMA-LITE MAGENTA CL4505.

The water-insoluble aluminum salts are preferably selected from FDC Yellow No 5 aluminum lake, le FDC Blue No 1 aluminum lake, le FDC Red No 40 aluminum lake, le FDC Red No 30 aluminum lake, le FDC Green No 5 aluminum lake, and their mixtures. As compound incorporating such inorganic lake may notably be cited the commercial references: INTENZA FIREFLY C91-1211, INTENZA AZURE ALLURE C91-1251, INTENZA THINK PINK C91-1236

The water-insoluble calcium salts are preferably selected from Red No 7 calcium lake. As compound incorporating such inorganic lake may notably be cited the commercial references: INTENZA MAGENTITUDE C91-1234, INTENZA HAUTE PINK C91-1232, INTENZA RAZZLED ROSE C91-1231, INTENZA AMETHYST FORCE C91-7231, INTENZA PLUSH PLUM C91-7441, INTENZA ELECTRIC CORAL C91-1233, FLORASOMES-JOJOBA-SMS-10% CELLINI RED-NATURAL and their mixture.

The water-insoluble sodium salts are preferably selected from Red No 6 sodium lake and Red No 28 sodium lake, and their mixture. E As compound incorporating such inorganic lake may notably be cited the commercial references: INTENZA MANGO TANGO C91-1221 and INTENZA NITRO PINK C91-1235.

The composition according to the invention may also be non-colored, "non-colored" or "uncolored" composition meaning a transparent or white composition.

For the purposes of the invention, the term "transparent composition" means a composition which transmits at least 40% of light at a wavelength of 750 nm without scattering it, i.e. a composition in which the scattering angle of the light is less than 5° and is better still about 0°.

The transparent composition may transmit at least 50%/a, especially at least 60% and especially at least 70% of light at a wavelength of 750 nm.

The transmission measurement is made with a Cary 300 Scan UV-visible spectrophotometer from the company Varian, according to the following protocol:

- the composition is poured into a square-sided spectrophotometer cuvette with a side length of 10 mm;
- the sample of the composition is then maintained in a thermostatically-regulated chamber at 20° C. for 24 hours;
- the light transmitted through the sample of the composition is then measured on the spectrophotometer by scanning wavelengths ranging from 700 nm to 800 nm, the measurement being made in transmission mode;
- the percentage of light transmitted through the sample of the composition at a wavelength of 750 nm is then determined.

The transparent compositions, when they are placed 0.01 m in front of a black line 2 mm thick in diameter drawn on a sheet of white paper, allow this line to be seen; in contrast, an opaque composition, i.e. a non-transparent composition, does not allow the line to be seen.

Tanning Agents

For the purposes of the present invention, the expression "skin self-tanning agent" means a compound that is capable of producing, on contact with the skin, a coloured reaction with the free amine functions present in the skin, such as amino acids, peptides or proteins.

The self-tanning agents are generally chosen from certain monocarbonyl or polycarbonyl compounds, for instance isatin, alloxan, ninhydrin, glyceraldehyde, mesotartaric aldehyde, glutaraldehyde, erythrulose, pyrazolin-4,5-dione derivatives as described in patent application FR 2 466 492 and WO 97/35842, dihydroxyacetone (DHA), and 4,4-dihydroxypyrazolin-5-ones as described in patent application EP 903 342. DHA will preferably be used.

DHA may be used in free and/or encapsulated form, for example in lipid vesicles such as liposomes, especially described in patent application WO 97/25970.

The self-tanning agent(s) is (are) generally present in proportions ranging from 0.1% to 15% by weight, preferably from 0.2% to 10% by weight and more preferentially from 1% to 8% by weight relative to the total weight of the composition.

Additional Moisturizers

For a particular care application, a composition according to the invention may comprise at least one additional moisturizer (also known as a humectant).

The moisturizer(s) may be present in the composition in a content ranging from 0.1% to 15% by weight, especially from 0.5% to 10% by weight or even from 1% to 6% by weight, relative to the total weight of the said composition.

Polyhydric alcohols, preferably of $C_2$-$C_8$ and more preferably $C_3$-$C_6$, preferably such as glycerol, propylene glycol, 1,3-butylene glycol, pentylene glycol, hexylene glycol, dipropylene glycol, diethylene glycol and diglycerol, and mixtures thereof, glycerol and derivatives thereof are known as moisturizers or humectants.

The composition according to the invention may also comprise an additional moisturizers or humectants.

These additional moisturizers or humectants that may especially be mentioned include sorbitol, glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, urea and derivatives thereof, especially Hydrovance (2-hydroxyethylurea) sold by National Starch, lactic acids, hyaluronic acid, AHAs, BHAs, sodium pidolate, xylitol, serine, sodium lactate, ectoin and derivatives thereof, chitosan and derivatives thereof, collagen, plankton, an extract of *Imperata cylindra* sold under the name Moist 24 by the company Sederma, acrylic acid homopolymers, for instance Lipidure-HM® from NOF Corporation, beta-glucan and in particular sodium carboxymethyl beta-glucan from Mibelle-AG-Biochemistry, a mixture of passionflower oil, apricot oil, corn oil and rice bran oil sold by Nestle under the name Nutra-Lipids®; a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product manufactured by Chimex under the trade name Mexoryl SBB®; an oil of musk rose sold by Nestle; spheres of collagen and of chondroitin sulfate of marine origin (Atelocollagen) sold by the company Engelhard Lyon under the name Marine Filling Spheres; hyaluronic acid spheres such as those sold by the company Engelhard Lyon; arginine, argan oil, and mixtures thereof.

Preferably, use will be made of a moisturizer chosen from glycerol, urea and derivatives thereof, especially Hydrovance® sold by National Starch, a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product manufactured by Chimex under the trade name Mexoryl SBB®; argan oil, and mixtures thereof.

More preferably, glycerol will be used.

Sunscreen/Sunblock Agents

Sunscreens are important skin-care products used to prevent photoaging and skin cancer. There are two groups of sunscreens: UVA sunscreens, which block UV radiation in the wavelength range of about 320 to 400 nm, and UVB sunscreens, which block radiation in the range of 290 to 320 nm.

The compositions in accordance with the invention comprise organic and/or inorganic UV sunscreen ingredients active in the UV-A and/or UV-B region which are hydrophilic and/or lipophilic.

In particular, the UV sunscreen ingredients according to the invention might have a solubility parameter ranging from 8.0 to 9.5. Said UV sunscreen ingredients have a good plasticizer function.

Advantageously, the UV sunscreen agent according to the invention might have a molecular weight ranging from 150 to 500 g/mol and contain hydrophobic sites and benzene nucleus or electron resonance group binding with polar sites.

The hydrophilic and/or lipophilic organic UV sunscreen ingredients are selected in particular from benzylidene camphor derivatives, dibenzoylmethane derivatives; cinnamic derivatives; salicylic derivatives; benzophenone derivatives; β,β-diphenylacrylate derivatives; p-aminobenzoic acid (PABA) derivatives; and their mixtures.

Mention may be made, as examples of organic UV sunscreen ingredients, of those denoted below under their INCI names:

para-Aminobenzoic acid derivatives:
PABA,
Ethyl PABA,
Ethyl Dihydroxypropyl PABA,
Ethylhexyl Dimethyl PABA, marketed in particular under the trademark "Escalol 507" by ISP,
Glyceryl PABA,
Dibenzoylmethane Derivatives:
Butyl Methoxydibenzoylmethane, marketed in particular under the trademark "Parsol 1789" by Hoffmann-LaRoche,
Isopropyl Dibenzoylmethane,
Salicylic Derivatives:
Homosalate, marketed under the trademark "Eusolex HMS" by Rona/EM Industries,
Ethylhexyl Salicylate, marketed under the trademark "Neo Heliopan OS" by Haarmann and Reimer,
Dipropyleneglycol Salicylate, marketed under the trademark "Dipsal" by Scher,
TEA Salicylate, marketed under the trademark "Neo Heliopan TS" by Haarmann and Reimer,
Cinnamic Derivatives:
Ethylhexyl Methoxycinnamate, marketed in particular under the trademark "Parsol MCX" by Hoffmann-LaRoche,
Isopropyl Methoxycinnamate,
Isoamyl Methoxycinnamate, marketed under the trademark "Neo Heliopan E 1000" by Haarmann and Reimer,
Cinoxate,
DEA Methoxycinnamate,
Diisopropyl Methylcinnamate,
Glyceryl Ethylhexanoate Dimethoxycinnamate,
β,β-Diphenylacrylate Derivatives:
Octocrylene, marketed in particular under the trademark "Uvinul N539" by BASF,
Etocrylene, marketed in particular under the trademark "Uvinul N35" by BASF,
Benzophenone Derivatives:
Benzophenone-1, marketed under the trademark "Uvinul 400" by BASF,
Benzophenone-2, marketed under the trademark "Uvinul D50" by BASF,
Benzophenone-3 or Oxybenzone, marketed under the trademark "Uvinul M40" by BASF,
Benzophenone-4, marketed under the trademark "Uvinul MS40" by BASF,
Benzophenone-5,
Benzophenone-6, marketed under the trademark "Helisorb 11" by Norquay,
Benzylidene camphor derivatives:
Terephthalylidene dicamphor sulfonic acid,
4-Methylbenzylidene camphor
and their mixtures.

The organic UV filter is selected from an aminobenzoic acid derivative, a dibenzoylmethane derivative, a salicylic acid derivative, a cinnamic derivative, a β,β diphenylacrylate derivative, a benzophenone derivative, benzylidene camphor derivative, and mixtures thereof.

The preferred UV sunscreen ingredients are selected in the group consisting of cinnamic derivatives, β,β diphenylacrylates derivatives, salicylic derivatives, and their mixtures.

The preferred UV sunscreen ingredients are especially selected in the group consisting of ethylhexyl methoxycinnamate, octocrylene and ethylhexyl salicylate, and their mixtures.

Mention may be made especially of ethylhexyl methoxycinnamate sold under the tradename UVINUL MC 80® by the company BASF, of ethylhexyl salicylate sold under the tradename NEO HELIOPAN OS® by the company SYMRISE and of octocrylene sold under the tradename NEO HELIOPAN 303® by the company SYMRISE.

The composition in accordance with the invention may comprise from 0.1% to 30% by weight, for example from 0.5 to 20% by weight, for example from 1 to 15% by weight, and for example at least 1% by weight, of UV sunscreen ingredient relative to the total weight of the composition.

According to one exemplary embodiment, the composition may comprise the microcapsules and at least one UV sunscreen ingredient in a weight ratio [mineral filler/UV sunscreen ingredient] ranging from 0.20 to 10, for example from 1 to 9.5, preferably from 3 to 9.

Advantageously, the composition of the invention comprises at least one UV filter and eventually an active agent.

Other Active Agents

For application in particular for caring for or making up skin, the composition according to the invention may comprise at least one active agent chosen from:

According to one advantageous embodiment, the combination according to the invention may be combined with one or more supplementary cosmetic active agents.

These active agents may be chosen from antiwrinkle agents vitamins, in particular B3, B8, B12 and B9, moisturizers, desquamating agents, anti-ageing active agents, depigmenting agents, antioxidants, etc.

These active agents may be present in the composition in a content ranging from 0.001% to 20% by weight, preferably from 0.01% to 10% by weight, and more preferably from 0.01% to 5% by weight, relative to the total weight of the composition.

Antiwrinkle agents: mention may be made to ascorbic acid and derivatives thereof, such as magnesium ascorbyl phosphate and ascorbyl glucoside; tocopherol and derivatives thereof, such as tocopheryl acetate; nicotinic acid and precursors thereof, such as nicotinamide; ubiquinone; glutathione and precursors thereof, such as L-2-oxothiazolidine-4-carboxylic acid; C-glycoside compounds and derivatives thereof, as described in particular hereinafter: extracts of plants, and in particular extracts of sea fennel and of olive leaf; and also plant proteins and hydrolysates thereof, such as rice or soybean protein hydrolysates; algal extracts and in particular of *laminaria*; bacterial extracts; sapogenins, such as diosgenin and extracts of *Dioscorea* plants, in particular of wild yam, containing them; α-hydroxy acids; β-hydroxy acids, such as salicylic acid and 5-n-octanoylsalicylic acid; oligopeptides and pseudodipeptides and acyl derivatives thereof; in particular {2-[acetyl-(3-trifluoromethylphenyl) amino]-3-methyl-butyrylamino}acetic acid and the lipopeptides sold by the company Sederma under the trade names Matrixyl 500 and Matrixyl 3000; lycopene; manganese salts and magnesium salts, in particular manganese and magnesium gluconates; and mixtures thereof;

Desquamating agents: mention will be made of beta-hydroxy acids, in particular salicylic acids and derivatives thereof other than 5-n-octanoylsalicylic acid; urea; glycolic acid, citric acid, lactic acid, tartaric acid, malic acid or mandelic acid; 4-(2-hydroxyethyl)piperazine-1-propanesulphonic acid (HEPES); extract of Saphora *japonica*; honey; N-acetylglucosamine; sodium methylglycine diacetate, alpha-hydroxy acids (AHAs), beta-hydroxy acids (BHAs), and mixtures thereof;

Depigmenting agents: mention may be made of ceramides, vitamin C and derivatives thereof, in particular vitamin CG, CP and 3-O ethyl vitamin C, alpha- and beta-arbutin, ferulic acid, kojic acid, resorcinol and derivatives thereof, calcium D-pantetheine sulphonate, lipoic acid, ellagic acid, vitamin B3, phenylethyl resorcinol, for instance Symwhite 377® from the company Symrise, a kiwi fruit (*Actinidia chinensis*) juice sold by Gattefosse, an extract of *Paeonia suffructicosa* root, such as the product sold by the company Ichimaru Pharcos under the name Botanpi Liquid B®, an extract of brown sugar (*Saccharum officinarum*), such as the extract of molasses sold by the company Taiyo Kagaku under the name Molasses Liquid, a mixture of undecylenic acid and undecylenoyl phenyl alanine, such as Sepiwhite MSHI from Seppic;

Antioxidants: mention may more particularly be made of tocopherol and esters thereof, in particular tocopheryl acetate; EDTA, ascorbic acid and derivatives thereof, in particular magnesium ascorbyl phosphate and ascorbyl glucoside; chelating agents, such as BHT, BHA, N,N'-bis(3,4,5-trimethoxybenzyl)ethylenediamine and its salts, and mixtures thereof.

When the active principle ascorbyl glucoside is present in the cosmetic composition according to the present invention, it is present in an amount lower than 0.05% by weight, and more preferably of 0.01% by weight relative to the total weight of the composition.

IV—Galenic Formulation

A composition according to the invention may be in the form of makeup compositions and/or care compositions for keratin materials, in particular for skin or lips. Particularly, a composition according to the invention may be a BB product or a foundation especially to be applied on the face or neck, a product for masking dark circles, a concealer product, a tinted cream, a colored composition for care or for making up the skin, especially for the face or body or an after-sun composition.

In the case of caring composition, the composition according to the invention comprises from 0.1% to 5% by weight and preferably from 0.1% to 3% by weight of microcapsules relative to the total weight of the said composition.

In a preferred embodiment, a composition according to the present invention is a non-rinsing composition. Thus, the composition may not intend to be rinsed after application on the skin.

In another preferred embodiment, the composition according to the present invention is not contained in a dispenser comprising a pump. This is advantageous since it avoids the risk for the microcapsules to be broken. Indeed, when using such a dispenser, said microcapsules could be crushed before their application on the keratin materials.

It is understood that the compositions according to the invention can be in any galenical form conventionally used for topical application, especially in the form of liquid or semi-liquid consistency of the milk type, or of soft, semisolid or solid consistency of the cream or gel type, or alternatively, an emulsion obtained by dispersing a fatty phase in an aqueous phase (O/W), an emulsion obtained by dispersing an aqueous phase in a fatty phase in (W/O), a multiple emulsion (W/O/W, O/W/O), or a foam.

Particularly the composition is in the form selected from the group consisting in a gel and in particular a transparent gel, a water-in-oil emulsion, an oil-in-water emulsion and a foam.

Surfactants

A composition according to the invention may comprise at least one surfactant (emulsifier), chosen especially from amphoteric, anionic, cationic and nonionic surfactants, used alone or as a mixture.

The surfactants are generally present in the composition in a proportion that may range, for example, from 0.3% to 20% by weight, in particular from 0.5% to 15% by weight and more particularly from 1% to 10% by weight of surfactants relative to the total weight of the composition.

Needless to say, the surfactant is chosen so as to effectively stabilize the emulsions more particularly under consideration according to the invention, namely of O/W, W/O or O/W/O type. This choice falls within the competence of a person skilled in the art.

For example, when the emulsifier potassium cetyl phosphate is present in the cosmetic composition according to the present invention, it is in a proportion that may range, for example, from 0.2% to 3% by weight, more particularly from 0.5% to 1.5% by weight and more preferably from 0.8% to 1.2% by weight, and even more preferably 1% by weight relative to the total weight of the composition.

O/W Emulsifiers

Examples that may be mentioned for the O/W emulsions include nonionic surfactants, and especially esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof; the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof; the sugar (sucrose, glucose or alkylglucose) esters of $C_8$-$C_{24}$ fatty acids, and the oxyalkylenated derivatives thereof; fatty alcohol ethers; the sugar ethers of $C_8$-$C_{24}$ fatty alcohols, and mixtures thereof.

Glyceryl esters of fatty acids that may especially be mentioned include glyceryl stearate (glyceryl monostearate, distearate and/or tristearate) (CTFA name: glyceryl stearate) or glyceryl ricinoleate, and mixtures thereof.

Polyethylene glycol esters of fatty acids that may especially be mentioned include polyethylene glycol stearate (polyethylene glycol monostearate, distearate and/or tristearate) and more especially polyethylene glycol 50 OE monostearate (CTFA name: PEG-50 stearate) and polyethylene glycol 100 OE monostearate (CTFA name: PEG-100 stearate), and mixtures thereof.

Mixtures of these surfactants may also be used, for instance the product containing glyceryl stearate and PEG-100 stearate, sold under the name Arlacel 165 by the company Uniqema, and the product containing glyceryl stearate (glyceryl mono-distearate) and potassium stearate, sold under the name Tegin by the company Goldschmidt (CTFA name: glyceryl stearate SE).

Fatty acid esters of glucose or of alkylglucose that may be mentioned in particular include glucose palmitate, alkylglucose sesquistearates, for instance methylglucose sesquistearate, alkylglucose palmitates, for instance methylglucose palmitate or ethylglucose palmitate, fatty esters of methylglucoside and more especially the diester of methylglucoside and of oleic acid (CTFA name: methyl glucose dioleate); the mixed ester of methylglucoside and of the oleic acid/hydroxystearic acid mixture (CTFA name: methyl glucose dioleate/hydroxysterate); the ester of methylglucoside and of isostearic acid (CTFA name: methyl glucose isostearate); the ester of methylglucoside and of lauric acid (CTFA name: methyl glucose laurate); the mixture of the monoester and diester of methylglucoside and of isostearic acid (CTFA name: methyl glucose sesquiisostearate); the mixture of the monoester and diester of methylglucoside and of stearic acid (CTFA name: methyl glucose sesquistearate) and in particular the product sold under the name Glucate SS by the company Amerchol, and mixtures thereof.

Examples of oxyethylenated ethers of a fatty acid and of glucose or of alkylglucose that may be mentioned include the oxyethylenated ethers of a fatty acid and of methylglucose, and in particular the polyethylene glycol ether of the diester of methyl glucose and of stearic acid containing about 20 mol of ethylene oxide (CTFA name: PEG-20 methyl glucose distearate), such as the product sold under the name Glucam E-20 distearate by the company Amerchol; the polyethylene glycol ether of the mixture of monoester and diester of methylglucose and of stearic acid containing about 20 mol of ethylene oxide (CTFA name: PEG-20 methyl glucose sesquistearate) and in particular the product sold under the name Glucamate SSE-20 by the company Amerchol, and the product sold under the name Grillocose PSE-20 by the company Goldschmidt, and mixtures thereof.

Examples of sucrose esters that may be mentioned include sucrose palmitostearate, sucrose stearate and sucrose monolaurate.

Examples of fatty alcohol ethers that may be mentioned include polyethylene glycol ethers of fatty alcohols containing from 8 to 30 carbon atoms and especially from 10 to 22 carbon atoms, such as polyethylene glycol ethers of cetyl alcohol, of stearyl alcohol or of cetearyl alcohol (mixture of cetyl alcohol and stearyl alcohol). Examples that may be mentioned include ethers comprising from 1 to 200 and preferably from 2 to 100 oxyethylene groups, such as those of CTFA name Ceteareth-20 and Ceteareth-30, and mixtures thereof.

Sugar ethers that may especially be mentioned are alkylpolyglucosides, for example decylglucoside, for instance the product sold under the name Mydol 10 by the company Kao Chemicals, the product sold under the name Plantaren 2000 by the company Henkel, and the product sold under the name Oramix NS 10 by the company SEPPIC; caprylyl/capryl glucoside, for instance the product sold under the name Oramix CG 110 by the company SEPPIC or under the name Lutensol GD 70 by the company BASF; laurylglucoside, for instance the products sold under the names Plantaren 1200 N and Plantacare 1200 by the company Henkel; cocoglucoside, for instance the product sold under the name Plantacare 818/UP by the company Henkel; cetostearyl glucoside optionally as a mixture with cetostearyl alcohol, sold, for example, under the name Montanov 68 by the company SEPPIC, under the name Tego-Care CG90 by the company Goldschmidt and under the name Emulgade KE3302 by the company Henkel; arachidyl glucoside, for example in the form of the mixture of arachidyl alcohol and behenyl alcohol and arachidyl glucoside, sold under the name Montanov 202 by the company SEPPIC; cocoylethylglucoside, for example in the form of the mixture (35/65) with cetyl alcohol and stearyl alcohol, sold under the name Montanov 82 by the company SEPPIC; and mixtures thereof.

W/O Emulsifiers

For the W/O emulsions, hydrocarbon-based or silicone surfactants may be used.

According to one embodiment variant, hydrocarbon-based surfactants are preferred.

Examples of hydrocarbon-based surfactants that may be mentioned include polyester polyols, for instance PEG-30 dipolyhydroxystearate sold under the reference Arlacel P 135 by the company Uniqema, and polyglyceryl-2 dipolyhydroxystearate sold under the reference Dehymuls PGPH by the company Cognis.

Examples of silicone surfactants that may be mentioned include alkyl dimethicone copolyols such as lauryl methicone copolyol sold under the name Dow Corning 5200 Formulation Aid by the company Dow Corning and cetyl dimethicone copolyol sold under the name Abil EM 90 by the company Goldschmidt, or the polyglyceryl-4 isostearate/cetyl dimethicone copolyol/hexyl laurate mixture sold under the name Abil WE 09 by the company Goldschmidt.

One or more co-emulsifiers may also be added thereto. The co-emulsifier may be chosen advantageously from the group comprising polyol alkyl esters. Polyol alkyl esters that may especially be mentioned include glycerol and/or sorbitan esters, for example the polyglyceryl-3 diisostearate sold under the name Lameform TGI by the company Cognis, polyglyceryl-4 isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

These compositions are prepared according to the usual methods.

The compositions of this type may be in the form of a facial and/or body care or makeup product, and may be conditioned, for example, in the form of cream in a jar or of fluid in a tube.

The compositions according to the invention may be solid or more or less fluid and having the appearance of a cream, a gel particularly a transparent gel, an ointment, a milk, a lotion, a serum, a paste, a foam (with or without associated propellant), a stick.

According to an embodiment, the composition is in the form of a gel and in particular a transparent gel, and comprising from 1 to 10% by weight relative to the weight of the composition of microcapsules.

Preferably, the viscosity of the gel according to the invention is superior or equal to 20UD (Mobile 3) by Rheomat at 25° C.

The viscosity is generally measured at 25° C. with a viscosimeter RHEOMAT RM 180 with Mobile 3 adapted to the viscosity of the product to be tested (mobile is chosen for having a measure between 10 and 90 for UD Unit Deviation), the measure being made after 10 mn rotating the mobile inside the composition, with a cisaillement from 200 s−1. The UD values may then be converted in Poises (1 Poise=0.1 Pa·s) with a correspondence table.

More preferably, such a composition contains a gelified aqueous phase.

Hydrophilic Gelifying Agent(s)

Hydrophilic gelifying agents that may be mentioned in particular include water-soluble or water-dispersible thickening polymers. These polymers may be chosen especially from:

- modified or unmodified carboxyvinyl polymers, such as the products sold under the name Carbopol (CTFA name: Carbomer) by the company Goodrich; polyacrylates
- polymethacrylates such as the products sold under the names Lubrajel and Norgel by the company Guardian or under the name Hispagel by the company Hispano Chimica;
- polyacrylamides; optionally crosslinked and/or
- neutralized 2-acrylamido-2-methylpropanesulfonic acid polymers and copolymers, for instance the poly(2-acrylamido-2-methylpropanesulfonic acid) sold by the company Clariant under the name Hostacerin AMPS (CTFA name: ammonium polyacryldimethyltauramide);
- crosslinked anionic copolymers of acrylamide and of AMPS, which are in the form of a W/O emulsion, such as those sold under the name Sepigel 305 (CTFA name: Polyacrylamide/C13-14 isoparaffin/Laureth-7) and under the name Simulgel 600 (CTFA name: Acrylamide/Sodium acryloyldimethyltaurate copolymer/Isohexadecane/Polysorbate 80) by the company SEPPIC;
- polysaccharide biopolymers, for instance xanthan gum, guar gum, carob gum, acacia gum, scleroglucans, chitin and chitosan derivatives, carrageenans, gellans, alginates,
  - celluloses such as microcrystalline cellulose, carboxymethylcellulose, hydroxymethylcellulose and hydroxypropylcellulose; and mixtures thereof. Preferably, these polymers may be chosen from Acrylates/C10-30 Alkyl Acrylate Crosspolymer such as, Carbopol ultrez 20, Carbopol ultrez 21, Permulen TR-1, Permulen TR-2, Carbopol 1382, Carbopol ETD 2020, Carbomer such as Synthalen K, carbopol 980, Ammonium acryloyldimethyl Taurate/Steareth-8 Methacrylate copolymer such as Aristoflex SNC, Acrylates copolymer such as Carbopol Aqua SF-1, Ammonium acryloyldimethyl taurate/steareth-25 Methacrylate Crosspolymer such as Aristoflex HMS, Ammonium acryloyldimethyl taurate such as Arisfoflex AVC, and xanthan gum such as Keltrol CG, etc, and also any polymers which contribute not only to sustain a proper viscosity, to further make capsule suspension very well and further to make it stable in shelf lives, but also to deliver a transparency.

According to a specific embodiment, the aqueous phase of the composition contains at least one neutralized 2-acrylamido-2-methylpropanesulfonic acid polymers and copolymers and one polysaccharide biopolymer.

Preferably, the hydrophilic gelifying agents suitable in the present invention include carboxyvinyl polymers such as the Carbopol products (carbomers) such as Carbopol Ultrez 20 Polymer@ marketed by Lubrizol and the Pemulen products (acrylate/$C_{10}$-C30-alkylacrylate copolymer); polyacrylamides, for instance the crosslinked copolymers marketed under the trademarks Sepigel 305 (CTFA name: polyacrylamide/$C_{13-14}$ isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) marketed by Hoechst under the trademark Hostacerin AMPS (CTFA name: ammonium polyacryloyldimethyltaurate) or Simulgel 800 marketed by SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 marketed by SEPPIC; cellulose-based derivatives such as hydroxyethylcellulose; polysaccharides and especially gums such as xanthan gum; and mixtures thereof.

More preferably, the hydrophilic gelifying agents are chosen among an acrylate/$C_{10}$-$C_{30}$-alkylacrylate copolymer, carbomer, xanthan gum, carboxyvinylic polymer synthetized in methylene chloride, and ammonium polyacryloyldimethyltaurate, and mixtures thereof.

These gelifying agents may be present in an amount ranging for example from 0.001 to 10% by weight, preferably 0.01 to 5% by weight and more preferably from 0.05 to 3% by weight relative to the total weight of said composition.

A composition according to the invention having a gelified aqueous phase may comprises from 1 to 10%, preferably from 1 to 5% by weight of one or more hydrophilic gelifying agents relative to the weight of the composition of microcapsules.

Such aqueous gel may also be transparent. This transparency may be evaluated as disclosed previously.

A composition in the form of a transparent gel according to the invention preferably comprises water and multi-layered microcapsules containing releasable material(s).

In a first preferred embodiment, a transparent gel according to the invention comprises at least one hydrophilic or lipophilic gelling agent and at least one water soluble emollient(s) and/or lipid(s) with a polar moiety.

In a first preferred embodiment, a transparent gel according to the invention comprises at least two types of different multi-layered microcapsules containing releasable material(s).

A transparent gel according to the invention, which is preferably a BB product or a foundation, provides very strong moisturizing sensation, transparent, cleaning bulk appearance with very comfortable feeling during application and sheer natural make-up result after application. These features help to deliver both skincare efficacy perception (watery, moisturization and transparent) as well as make-up efficacy (proper coverage).

Advantageously, a transparent gel contains a swelling agent, this agent allows a better swelling of the microcapsules thus rendering the microcapsules easier to break during application. Water, alcohols, glycols polyols may be used as swelling agent. Examples of swelling agents are disclosed above.

The moisturization may further be enhanced by introduction of one or more water soluble emollient(s) and/or lipid(s) with a polar moiety. PEG modified silane and silicone such as Bis-PEG-18 Methyl ether dimethyl silane, and/or PEG modified ester such as PEG-7 Olivate, PEG-7 Glyceryl Cocoate, PEG-30 Glyceryl Cocoate, PEG-80 Glyceryl Cocoate, may be used to enhance moisturization.

A solubilizer may also be added in order to keep the properties of the transparent gel on storage, in particular to make emollients solubilized in water phase, to make and keep gel transparent and stable in shelf lives. Polysorbate 20, PEG-60 hydrogenated castor oil may be mentioned as examples of solubilizers.

A transparent gel according to the invention presents a very beautiful, clean and tidy appearance, with pigments releasing during application without any particle feeling. Makeup results are perfectly and evenly provided after application.

A preferred embodiment of a transparent gel according to the invention comprises:

at least one of the polymers chosen from Acrylates/C10-30 Alkyl Acrylate Crosspolymer such as Permulen TR-1, Permulen TR-2, Carbopol 1382, Carbopol ETD 2020, preferably in a concentration from 0 to 10% wgt, more preferably from 0 to 2% wgt, Carbomer such as Synthalen K, carbopol 980 preferably in a concentration from 0 to 10% wgt, more preferably from 0 to 2% wgt, Ammonium acryloyldimethyl Taurate/Steareth-8 Methacrylate copolymer such as Aristoflex SNC, preferably in a concentration from 0 to 10% wgt, more preferably from 0 to 2% wgt, Acrylates copolymer such as Carboplol Aqua SF-1 preferably in a concentration from 0 to 10% wgt, more preferably from 0 to 2% wgt, Ammonium acryloyldimethyl taurate/steareth-25 Methacrylate Crosspolymer such as Aristoflex HMS, preferably in a concentration from 0 to 10% wgt, more preferably from 0 to 2% wgt, Ammonium acryloyldimethyl taurate such as Arisfoflex AVC, preferably in a concentration from 0 to 10% wgt, more preferably from 0 to 4% wgt and xanthan gum such as Keltrol CG, preferably in a concentration from 0 to 10% wgt, more preferably from 0 to 4% wgt.

Moreover, a transparent gel may contain at least one of the following swelling agent, water such as deionized water, preferably in a concentration from 0 to 90% wgt, more preferably from 30 to 70% wgt, alcohols preferably in a concentration from 0 to 50% wgt, more preferably from 1 to 20% wgt, glycols such as propyl glycol, butyl glycol, preferably in a concentration from 0 to 50% wgt, more preferably from 1 to 15% wgt, polyols such as glycerin, tetraols, preferably in a concentration from 0 to 50% wgt, more preferably from 1 to 10% wgt.

In addition, a transparent gel may contain at least one water soluble emollients chosen from Bis-PEG-18 Methyl ether dimethyl silane, PEG-7 Olivate, PEG-7 Glyceryl Cocoate, PEG-30 Glyceryl Cocoate, PEG-80 Glyceryl Cocoate, in a concentration from 0 to 20% wgt, more preferably from 0 to 5% wgt, and at least one solubilizers such as polysorbate 20, PEG-60 hydrogenated castor oil, in a concentration from 0 to 100 wgt, more preferably from 1 to 5% wgt.

Such obtained transparent gel with microcapsules presents a pure and clean appearance, with perfect stability under −20/20° C. (5 cycles), room temperature (25° C., 2 months), 37° C. (2 months) and 45° C. (2 months). The microcapsules release material during application without any particle feeling. Makeup results are perfectly and evenly provided after application.

However, a transparent gel could also by slightly colored.

In this case, a transparent gel comprises at least one colorant, preferably in an amount of less than 1% by weight based on the total weight of the total composition.

The composition may also be in a form of a gelly cream, or emulsionated gel, comprising oils and surfactants.

According to another embodiment, the composition according to the invention is in the form of a foam comprising from 1 to 30% by weight relative to the weight of the composition of microcapsules.

The term “composition in (the) foam form” and the term “foam type formulation” have the same meaning and are understood to mean a composition comprising a gas phase (for example air) in the form of bubbles; another equivalent term is “composition expanded in volume”.

In one embodiment, a foam composition is obtained without any propellant (non aerosol foam).

In another preferred embodiment, a foam composition is obtained with a propellant (aerosol foam) The composition in the foam form according to the invention may be obtained from a composition of the invention used as "base composition" packaged in a product. This product may contain, besides the base composition, a propellant.

Thus, the present invention further relates to a product comprising:

a. a container defining at least one compartment;

b. a composition of the invention contained in said compartment, c. a propellant to pressurize said composition inside said compartment; and d. a dispensing head having an opening to be selectively put in fluid communication with said compartment in order to deliver said pressurized composition in the form of a foam.

According to yet another embodiment, the present invention relates to a kit comprising one of the product defined above and an applicator.

The compositions in the foam form according to the invention are formed stably in the form of mousse using a composition of the invention and air or an inert gas.

The air or the inert gas may represent especially from 10% to 500% and preferably from 20% to 200%, for example from 30% to 100% of the volume of the composition in the foam form.

This volume may be calculated by comparing the density of the base composition and of the in the foam form composition.

Besides air, gases that allow the composition in the foam form to be obtained are in particular inert gases, for example nitrogen, carbon dioxide, nitrogen oxides, noble gases or a mixture of the said gases. When the composition comprises an oxidation-sensitive compound, it is preferable to use an oxygen-free gas such as nitrogen or carbon dioxide.

The amount of gas introduced into the base composition contributes towards adjusting the density of the composition in the foam form to the desired value, for example less than or equal to 0.12 $g/cm^3$.

The composition in the foam form of the invention may have for example a density of less than or equal to 0.12 $g/cm^3$, for example ranging from 0.02 to 0.11 $g/cm^3$ and preferably from 0.06 to 0.10 $g/cm^3$, this density being measured at a temperature of about 20° C. and at atmospheric pressure according to the following protocol.

Density Measurement

The test is performed on 50 ml of composition introduced into a 50 ml polished Plexiglas® goblet ($V_1$) defining a cylindrical filling space 30 mm high having a base with a diameter of 46 mm. The goblet has a bottom wall 10 mm thick and a side wall 12 mm thick.

Before measurement, the composition to be characterized and the goblet are maintained at a temperature of about 20° C. The goblet is tared and the weight value ($M_1$) is recorded. The composition in the foam form is then introduced into the goblet so as to occupy the total volume, while avoiding the formation of air bubbles during the filling of the goblet. The assembly is left to stand for 10 seconds to allow the mousse to expand fully. The top of the goblet is then skimmed before weighing ($M_2$). The density is assessed according to the convention $\rho=(M_2-M_1)/50$.

Stability Measurement

The composition in the foam form according to the invention shows satisfactory stability, which may be calculated by measuring the volume of mousse ($V_2$) remaining in the goblet after 10 minutes according to the protocol described above for the density measurement.

The ratio $V_2/V_1$ corresponds to the ratio between the volume of the composition in the foam form after 10 minutes and the volume of the composition in the foam form after 10 seconds.

The expression "satisfactory stability" applies especially to compositions in the foam form with a ratio $$\frac{V_2}{V_1}$$

of greater than 0.85 and especially greater than 0.90, for example greater than 0.95.

For a given weight of composition in the foam form, the volume of the composition in the foam form is inversely proportional to the density of the composition in the foam form. Thus, the ratio between the density of the composition in the foam form measured after 10 seconds and the density of the composition in the foam form measured after 10 minutes may be greater than 0.85 and especially greater than 0.90, for example greater than 0.95.

Within the composition in the foam form according to the invention, the air pause may advantageously have a number-average size ranging from 20 μm to 500 μm and preferably ranging from 100 μm to 300 μm.

The composition in the foam form may be obtained from a composition of the invention in a distributor. This distributor may be an aerosol containing, besides the base composition, a propellant.

This propellant may represent less than 20% by weight of the base composition and in particular may represent from 1% to 10% by weight, for example from 2 to 8% by weight, for example at least 5% by weight of the total weight of the base composition. The propellant that may be used may be chosen from carbon dioxide, nitrogen, nitrous oxide and volatile hydrocarbons such as butane, isobutane, propane, ethane, pentane, isododecane or isohexadecane, and mixtures thereof.

It may especially be a propane/butane mixture (Liquified Petroleum Gas or LPG) in a weight ratio [propane/butane] ranging from 0.1 to 1, especially of 0.31.

The pressure of the propellant, and for example of said propane/butane mixture, in the aerosol may range from 0.20 to 0.50 MPa, for example from 0.20 to 0.40, and especially from 0.25 to 0.35 MPa.

The compositions in the foam form employed in the invention can be prepared by processes for mixing, stirring or dispersing compressed gases, such as air, chlorofluorocarbon-based compounds, nitrogen, carbon dioxide, oxygen or helium, a process for mixing and stirring in the presence of a foaming agent, such as a surfactant.

In particular, the composition in the foam form is prepared by mixing the ingredients with stirring, generally under hot conditions, and by then expanding in volume under the action of a gas, it being possible for the gas to be introduced during the stage of cooling the composition or after preparation of the composition, for example using a device for expanding in volume of Mondomix type, a beater of Kenwood type, a scraped-surface exchanger or a dynamic mixer (of IMT type, for example). The gas is preferably air or nitrogen.

The composition according to the invention can be packaged in a container delimiting at least one compartment which comprises the composition, the container being closed by a closure part. The container can be equipped with a means for the dispensing of the product.

The container can be a pot.

The container can be at least partly made of thermoplastic. Mention may be made, as examples of thermoplastics, of polypropylene or polyethylene. Alternatively, the container is made of nonthermoplastic material, in particular of glass or metal (or alloy).

The composition can be applied, e.g., by finger or using an applicator.

The container is preferably used in combination with an applicator comprising at least one application component configured in order to apply the composition to keratinous substances.

According to another advantageous embodiment, the applicator comprises an application nozzle.

The foam composition according to the invention comprises from 1 to 30%, preferably from 3 to 10% by weight relative to the weight of the composition of microcapsules.

The obtained foam is fine (small bubbles) and contains The foam composition may also comprise calcium carbonate ($CaCO_3$) in order to avoid coloration of the water phase.

The foam composition according to the invention comprises from 1 to 10%, preferably from 3 to 8% by weight relative to the weight of the composition of fillers and/or pigments advantageously $TiO_2$, The foam composition according to the invention comprises from 0.5 to 5%, preferably from 1 to 3% by weight relative to the weight of the composition of calcium carbonate.

According to another embodiment, a composition according to the invention is an oil in water (O/W) emulsion.

This make up composition, which is preferably a makeup BB product for face or a foundation, provides very strong moisturizing sensation, creamy texture with very comfortable feeling during application, and sheer natural makeup result after application. After application, all these features help to deliver a very good balance of skincare efficacy perception (creamy and moisturization) as well as makeup efficacy (proper coverage and natural radiance). Advantageously, an appropriate sunscreen agent may be added.

This composition mainly comprises water, at least one non-volatile oil at least one O/W emulsifier and microcapsules.

The non-volatile oil(s) used in this preferred embodiment are the ones previously cited.

Advantageously the O/W emulsion contains a swelling agent, this agent allow a better swelling of the microcapsules thus rendering the microcapsules easier to break during application. Water, alcohols, glycols, polyols may be used as swelling agent.

Preferably the O/W emulsion also contains a co-emulsifier and/or a solubilizer.

Cetyl alcohol and stearyl alcohol may be cited as co-emulsifiers.

The solubilizer may be added in order to keep the properties of the O/W emulsion on storage, in particular to solubilize the ingredients of the water phase, to make and keep the composition stable in shelf lives. Polysorbate 20, PEG-60 hydrogenated castor oil may be mentioned as examples of solubilizers.

An O/W emulsion with perfect stable capsules in storage, with pigments releasing during application without any particle feeling is obtained. Makeup results are perfectly and evenly provided after application.

Moreover O/W emulsion may contain at least one of the following swelling agent, water such as deionized water, preferably in a concentration from 0 to 90% wgt, more preferably from 30 to 70% wgt, alcohols preferably in a concentration from 0 to 50% wgt, more preferably from 1 to 20% wgt, glycols such as propylene glycol, butylenes glycol, preferably in a concentration from 0 to 50% wgt, more preferably from 1 to 15% wgt, polyols such as glycerin, tetraols, preferably in a concentration from 0 to 50% wgt, more preferably from 1 to 10% wgt, co-emulsifier such as cetyl alcohol and stearyl alcohol, at high temperature above 60° C., preferably in a concentration from 0 to 20% wgt, more preferably from 1 to 5% wgt and solubilizer such as PEG-60 hydrogenated castor oil in a concentration from 0 to 10% wgt, more preferably from 1 to 5% wgt.

O/W emulsion can be obtained with pure and clean appearance of bulk, with perfect stability under −20/20° C. (5 cycle), room temperature (25° C., 2 months), 37° C. (2 months) and 45° C. (2 months). However, capsules would release pigments during application without any particle feeling. Makeup results are perfectly and evenly provided after application.

Moreover, organic sun filter can be added in the system and provide additional sun care benefit.

Throughout the description, including the claims, the term "comprising a" should be understood as being synonymous with "comprising at least one", unless otherwise mentioned.

The terms "between . . . and . . . " and "ranging from . . . to . . . " should be understood as being inclusive of the limits, unless otherwise specified.

The invention is illustrated in greater detail by the examples according to the invention described below. Unless otherwise mentioned, the amounts indicated are expressed as mass percentages of active material.

EXAMPLES

I. Microcapsules

Different examples of preparation of microcapsules according to the invention are here below described for illustrating the invention.

The following particles according to the invention are implemented in the examples:

- bismuth oxychloride (Ronaflair LF 2000 de Merck), entitled <<A>> in the following examples,
- mica-titanium dioxide-iron oxide (COLORONA ORIENTAL BEIGE sent by MERCK, entitled <<B>> in the following examples,
- mica-titanium dioxide-iron oxide (Timica® Terra Yellow MN4502 sent by BASF), entitled <<C>> in the following examples,
- mica-titanium dioxide-iron oxide (Timica® Terra Red MN4506 sent by BASF), entitled <<D>> in the following examples,
- MICA AND IRON OXIDE AND TITANIUM DIOXIDE AND TIN OXIDE (PRESTIGE SOFT BEIGE sent by SUDARCHAN CHEMICAL), entitled <<E>> in the following examples,
- TITANIUM DIOXIDE (and) MICA (Timiron Silk Red (Merck), entitled <<F>> in the following examples,
- mica-titanium dioxide-tin oxide-yellow 5 lake (INTENZA FIREFLY C91-1211 de SUN), entitled <<G>> in the following examples,
- TITANIUM DIOXIDE AND SYNTHETIC FLUORPHLOGOPITE (Sunshine Spectral Gold ore Red sent by SUN), entitled <<H>> in the following examples, TITANIUM DIOXIDE AND SYNTHETIC FLUORPHLOGOPITE (unshine Fine White sent by SUN), entitled <<I>> in the following examples, ALUMINUM FLAKE COVERED BY SILICA AS INTERFERENTIAL LAYER AND COATED WITH SILVER PARTICLE AS OUTER LAYER (60/29/9) (COSMICOLOR CELESTE AQUA GREEN sent by TOYAL), entitled <<J>> in the following examples.

Examples 1

Example 1a

Mannitol (spray dried mannitol: Pearlitol 100SD) is used as a core.

To a solution of 7,382 g of water and 66 g of Starch derivative (Structure XL) is completely dissolved at room temperature to prepare a first solution. To a mixed solutions of 418 g of water with 22 g of Polyvinyl alcohol (SELVOL™ (Celvol®) Polyvinyl alcohol 205S) is completely dissolved at 95° C. to prepare a second solution. These solutions are combined to form a mixture. At this stage, 1,080 g of Syncrystal almond (a reflective particle) is added to the mixture and well dispersed with a homogenizer (3000 rpm, 20 min.) to prepare an inner charged coating solution.

832 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This yields particles with the size range of approximately 75 μm~212 μm.

Thereafter, to a solution of 5,000 g of water, 32.8 g of cornstarch and 6.6 g of hydrogenated lecithin (Lipoid P75-3) are added and dissolved at 40° C. To the resulting mixture, 1,300 g of titanium dioxide particles (HOMBITAN FF-PHARMA) are added and well dispersed with a homogenizer (3000 rpm, 20 min.) to prepare a titanium dioxide particle coating solution.

A coating with the resulting titanium dioxide particle coating solution is generated by a fluidized bed process to obtain particles having an inner charged layer coated with a titanium dioxide particle layer.

Then, 2.0 g of cornstarch is dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. The resulting coated particles produced according to this process are obtainable with a size ranging from approximately 75 μm~250 μm.

Example 1b

Mannitol (spray dried mannitol: Pearlitol 100SD) is used as a core.

To a solution of 14382.5 g of water and 130 g of Starch derivative (Structure XL) is completely dissolved at room temperature to produce a first solution. To a mixed solution of 617.5 g of water with 32.5 g of Polyvinyl alcohol (SELVOL™ (Celvol®) Polyvinyl alcohol 205S) is completely dissolved at 95° C. to produce a second solution. After mixing the first and second solutions, 1080 g of Timica® Terra White (a reflective particle) is added and well dispersed with a homogenizer (3000 rpm, 20 min.) to prepare an inner charged coating solution.

537.5 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This process yields particles with the size range 75 μm~212 μm.

Thereafter, to a solution of 2200 g of water, 14 g of cornstarch and 2.8 g of hydrogenated lecithin (Lipoid P75-3) are added and dissolved at 40° C. To the resulting mixture, 560 g of titanium dioxide particles (HOMBITAN FF-PHARMA) are added and well dispersed with a homogenizer (3000 rpm, 20 min.) to prepare a titanium dioxide particle coating solution.

A coating with the resulting titanium dioxide particle coating solution is generated by a fluidized bed process to obtain particles having an inner charged layer coated with a titanium dioxide particle layer.

Then, 2.0 g of cornstarch is dissolved in 400 g of water at 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. Coated particles produced according to this method are obtainable with a size range of approximately 75 μm~250 μm.

Example 1c

Mannitol (spray dried mannitol: Pearlitol 100SD) is used as a core.

132 g of Starch derivative (Structure XL) is completely dissolved in 11,837 g of water at room temperature to produce a first solution. 33 g of Polyvinyl alcohol (SELVOL™ (Celvol®) Polyvinyl alcohol 205S) is completely dissolved in 627 g of water at 95° C. to produce a second solution. After mixing the first and second solutions, 1800 g of Syncrystal almond (a reflective particle) is added and well dispersed with a homogenizer (3000 rpm, 20 min.) to prepare an inner charged coating solution.

535 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This method generates particles with a size range of approximately 75 μm~212 μm.

Thereafter, to a solution of 2600 g of water, 14.0 g of cornstarch and 2.8 g of hydrogenated lecithin (Lipoid P75-3) are added and dissolved at 40° C. To the resulting mixture, 560 g of titanium dioxide particles (HOMBITAN FF-PHARMA) are added and well dispersed with a homogenizer (3000 rpm, 20 min.) to prepare a titanium dioxide particle coating solution.

A coating with the resulting titanium dioxide particle coating solution is realized by a fluidized bed process to obtain particles having an inner charged layer coated with a titanium dioxide particle layer.

Then, 1.2 g of cornstarch is dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. Coated particles produced according to this method are obtainable with a size range of approximately 75 m-250 μm.

Example 1d

Mannitol (spray dried mannitol: Pearlitol 100SD) is used as a core.

66 g of Starch derivative (Structure XL) is completely dissolved in 7,382 g of water at room temperature to produce a first solution. 22 g of Polyvinyl alcohol (SELVOL™ (Celvol®) Polyvinyl alcohol 205S) is completely dissolved in 421 g of water at 95° C. to produce a second solution. After mixing the first and second solutions, Syncrystal almond (a reflective particle) is added and well dispersed with a homogenizer (3000 rpm, 20 min.) to prepare an inner charged coating solution.

832 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This process generates particles with the size range of approximately 75 μm~212 μm.

Thereafter, to a solution of 5200 g of water, 27.6 g of cornstarch and 5.6 g of hydrogenated lecithin (Lipoid P75-3) are added and dissolved at 40° C. To the resulting mixture, 1100 g of titanium dioxide particles (HOMBITAN FF-PHARMA) are added and well dispersed with a homogenizer (with 3000 rpm, 20 min.) to prepare a titanium dioxide particle coating solution.

A coating with the resulting titanium dioxide particle coating solution is realized by a fluidized bed process to obtain particles having an inner charged layer coated with a titanium dioxide particle layer.

Then, 2.0 g of cornstarch is dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. Coated particles produced according to this method are obtainable with a size range of approximately 75 μm~250 μm Example 1e Mannitol (spray dried mannitol: Pearlitol 100SD) is used as a core.

144 g of Starch derivative (Structure XL) is completely dissolved at room temperature in 14,566 g of water to produce a first solution. 36 g of polyvinyl alcohol (SELVOL™ (Celvol®) Polyvinyl alcohol S325) is completely dissolved in 684 g of water at 95° C. to produce a second solution. After mixing the first and second solution, 1800 g of Colorona® Oriental Beige (a reflective particle) is added and well dispersed with a homogenizer (3000 rpm, 20 min.) to prepare an inner charged coating solution.

520 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This process yields articles with a size range of approximately 75 μm-212 μm.

Thereafter, to a solution of 2600 g of water, 14.0 g of cornstarch and 2.8 g of hydrogenated lecithin (Lipoid P75-3) are added and dissolved at 40° C. To the resulting mixture, 560 g of titanium dioxide particles (HOMBITAN FF-PHARMA) are added and well dispersed with a homogenizer (3000 rpm, 20 min.) to prepare a titanium dioxide particle coating solution.

A coating with the resulting titanium dioxide particle coating solution is realized by a fluidized bed process to obtain particles having an inner charged layer coated with a titanium dioxide particle layer.

Then, 1.2 g of cornstarch and 0.6 g of hydrogenated lecithin (Lipoid P 75-3) are dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. This method generates coated particles with a size range of approximately 75 μm~250 μm Example 1f Mannitol (spray dried mannitol: Pearlitol 100SD) is used as a core.

5750.0 g of ethanol, 75.0 g of ethyl cellulose (Ethocel standard 10 premium) and 150 g of FCC (SE-06) are completely dissolved in 1437.5 g of water at room temperature.

To the resulting mixture, 1800 g of Colorona® Oriental Beige (a reflective particles) are added and well dispersed with a homogenizer (3000 rpm, 20 min) to prepare an inner charged coating solution.

469.5 g of Mannitol is introduced into a fluidized bed coating system (Glatt GPOG 1, bottom spray) as a seed and subjected to a coating at 500 m/h of feeding rate of the inner color charged solution to obtain particles having a mannitol core coated with an inner charged layer. This process yields particles with the size range of approximately 75 μm~212 μm.

Thereafter, to a solution of 2400 g of water, 14.0 g of cornstarch and 2.8 g of hydrogenated lecithin (Lipoid P75-3) are added and dissolved at 40° C. To the resulting mixture, 560 g of titanium dioxide particles (KRONOS1171) are added and well dispersed with a homogenizer (3000 rpm, 20 min.) to prepare a titanium dioxide particle coating solution.

A coating with the resulting titanium dioxide particle coating solution is generated by a fluidized bed process to obtain particles having an inner charged layer coated with a titanium dioxide particle layer.

Then, 1.2 g of cornstarch and 0.6 g of hydrogenated lecithin (Lipoid P75-3) are dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. Coated particles prepared according to this method are obtainable with the size range of approximately 75 μm~250 μm Example 1g Mannitol (spray dried mannitol: Pearitol 100SD) is used as core.

To a mixed solution of 1600.0 g of methylene chloride and 1600.0 g of ethanol, 120.0 g of ceramide (Ceramide PC 104) and 120.0 g of hydrogenated lecithin (Lipoid S 100-3) are added and completely dissolved at 40° C. To the resulting mixture, 2000 g of reflective particles B are added and well dispersed with a homogenizer to prepare an inner charged coating solution.

347.70 g of Mannitol is introduced into a fluidized bed coating system (Glatt GPCG 1, bottom spray) as a seed and subjected to a coating at 500 ml/h of feeding rate of the inner color charged solution to obtain particles having a mannitol core coated with an inner charged layer.

Thereafter, to a mixed solution of 720.0 g of methylene chloride and 720.0 g of ethanol, 36.0 g of ceramide and 36.0 g of hydrogenated lecithin are added and dissolved at 40° C. To the resulting mixture, 600.0 g of titanium dioxide particles are added and well dispersed with a homogenizer to prepare a titanium dioxide particle coating solution.

A coating with the resulting titanium dioxide particle coating solution is realized by a fluidized bed process to obtain particles having an inner charged layer coated with a titanium dioxide particle layer.

Then, 300.0 g of shellac is dissolved in 3000 g of ethanol to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer Examples 1a to 1 g are called "Examples 1" in the following text.

Example 2

The same procedure as in Example 1g is repeated to the step for forming a titanium dioxide particles layer.

Thereafter, to a mixed solution of 400.0 g of methylene chloride and 400.0 g of ethanol, 20.0 g of ceramide and 20.0 g of hydrogenated lecithin are added and dissolved at 40° C.

To the resulting reaction mixture 500 g of reflective particles J is added and well dispersed with a homogenizer to prepare a green color coating solution.

A coating with the resulting charged coating solution is realized by a fluidized bed process at 500 ml/h of feeding rate of the coating solution to obtain particles having a titanium dioxide particle layer coated with a reflective particle charged layer.

Then, 200.0 g of polymethacrylate (Eudragit RSPO) is dissolved in 4000 g of ethanol to prepare an outer layer coating solution. A coating with the resulting outer layer coating solution is realized by a fluidized bed process at 100 ml/h of feeding rate of the coating solution to obtain a microcapsule having an inner layer encapsulating a reflective particle and being coated with a polymeric outer layer.

Example 3

By using the ingredients and contents described in the below table, a microcapsule having a core and 2 layers is prepared by the procedure provided in any of Examples 1 or example 2, especially in example 1b:

(1) reflective particle F (2) Ingredients: Core seed—reflective particle inner layer—$TiO_2$ particle layer

| | | |
|---|---|---|
| Core | Mannitol | 16.45% |
| 1st layer | reflective particle F | 50.0% |
| | Lecithin | 0.5% |
| | Corn Starch binder | 2.0% |
| 2nd layer | Titanium dioxide | qsp. 100% |
| | Lecithin | 0.2% |
| | Corn Starch binder | 0.8% |

Percentages indicate weight percent relative to the total microcapsule weight.

Example 4

By using the ingredients and contents described in the below table, a microcapsule having a core and 3 layers is prepared by the procedure provided in any of Examples 1 or example 2, especially in example 1b:

(1) reflective particle C (2) Ingredients: Core seed—reflective particle inner layer—$TiO_2$ particle layer—outer color layer

| | | |
|---|---|---|
| Core | Mannitol | 6.5% |
| 1st layer | reflective particle C | 17.8% |
| | Sunpuro Yellow | 2.00% |
| | Lecithin | 5.0% |
| | Eudragit RSPO | 4.0% |
| 2nd layer | Titanium dioxide | qsp. 100% |
| | Lecithin | 5.0% |
| | Eudragit RSPO | 4.0% |
| 3rd layer | D&C Red30 | 0.8% |
| | Cornstarch binder | 0.4% |

Percentages indicate weight percent relative to the total microcapsule weight.

Example 5

By using the ingredients and contents described in the below table, a microcapsule having a core and 2 layers is prepared by the procedure provided in any of Examples 1 or example 2, especially in example 1b:

(1) reflective particle A (2) Ingredients: Core seed—reflective particle inner layer—$TiO_2$ particle layer

| | | |
|---|---|---|
| Core | Mannitol | 17.8% |
| 1st layer | Reflective particle A | 19.8% |
| | Lecithin | 0.2% |
| | Corn Starch binder | 0.8% |
| 2nd layer | Titanium dioxide | qsp. 100% |
| | Mannitol | 5.0% |
| | Corn Starch | 5.0% |
| | Lecithin | 0.3% |
| | Corn Starch binder | 1.2% |

Percentages indicate weight percent relative to the total microcapsule weight.

Example 6

By using the ingredients and contents described in the below table, a microcapsule having a core and 2 layers is prepared by the procedure provided in any of Examples 1 or example 2, especially in example 1b:

(1) Ingredients: Core seed—Reflective particle inner color layer—$TiO_2$ particle layer

| | | |
|---|---|---|
| Core | Mannitol | 13.7% |
| 1st layer | Reflective particle D | 21.64% |
| | Lecithin | 0.20% |
| | Corn Starch Binder | 1.0% |
| 2nd layer | Titanium dioxide | qsp. 100% |
| | Lecithin | 0.3% |
| | Corn Starch Binder | 1.5% |

Percentages indicate weight percent relative to the total microcapsule weight.

Example 7

By using the ingredients and contents described in the below table, a microcapsule having a core and 3 layers is prepared by the procedure provided in any of Examples 1 or example 2, especially in example 1b:

(1) Reflective particle H (2) Ingredients: Core seed—reflective particle inner layer—$TiO_2$ particle layer—Outer color layer

| | | |
|---|---|---|
| Core | Mannitol | 16.81% |
| 1st layer | reflective particle H | 49.15% |
| | Lecithin | 0.29% |
| | Corn Starch Binder | 1.97% |
| 2nd layer | Titanium dioxide | qsp100%% |
| | Lecithin | 0.1% |
| | Corn Starch Binder | 0.49% |
| 3rd layer | Sunpuro Yellow | 1.0% |
| | Sunpuro Red | 0.2% |
| | Corn Starch Binder | 0.5% |

Percentages indicate weight percent relative to the total microcapsule weight.

Example 8

By using the ingredients and contents described in the below table, a microcapsule having a core and 3 layers is prepared by the procedure provided in any of Examples 1 or example 2, especially in example 1b:

(1) reflective particle H (2) Ingredients: Core seed—reflective particle inner layer—$TiO_2$ particle layer—Outer color layer

| | | | | |
|---|---|---|---|---|
| Core | Organic core | 4.0% | Cellulose | 1.12% |
| | | | Mannitol | 1.0% |
| | | | *Zea Mays*(corn) starch | 1.84% |
| | | | Hydrogenated Lecithin | 0.04% |
| 1st layer | reflective particle H | 55.0% | reflective particle | 55 |
| | Lecithin | 0.50% | Hydrogenated Lecithin | 0.50% |
| | Mannitol | 3.5% | Mannitol | 3.5% |
| | Corn Starch Binder | 2.0% | *Zea Mays*(corn) starch | 2.0% |
| 2nd layer | Titanium dioxide | qsp 100%. | Titanium dioxide | qsp 100%. |
| | Corn Starch | 3.62% | *Zea Mays*(corn) starch | 3.62% |
| | Cellulose | 9.0% | Cellulose | 9.0% |
| | Mannitol | 13.0% | Mannitol | 13.0% |
| | Lecithin | 0.25% | Hydrogenated Lecithin | 0.25% |

-continued

| | | | | |
|---|---|---|---|---|
| | Corn Starch Binder | 1.8% | *Zea Mays*(corn) starch | 1.8% |
| 3rd Layer | Satin White | 1.8% | Synthetic Fluorphlogopite | 1.035% |
| | | | Tin oxide | 0.009% |
| | | | Titanium Dioxide | 0.756% |
| | D&C Red30 | 0.03% | Red30 Al. Lake | 0.03% |
| | Corn Starch Binder | 0.5% | *Zea Mays*(corn) starch | 0.5% |

Percentages indicate weight percent relative to the total microcapsule weight.

Example 9

By using the ingredients and contents described in the below table, a microcapsule having a core and 3 layers is prepared by the procedure provided in any of Examples 1 or example 2, especially in example 1b:

(1) reflective particle G (2) Ingredients: Core seed—reflective particle inner layer—$TiO_2$ particle layer—Outer color layer

| | | |
|---|---|---|
| Core | Mannitol | 34.4% |
| 1st layer | reflective particle G | 50.0% |
| | Lecithin | 0.50% |
| | Mannitol | 4.0% |
| | Corn Starch Binder | 2.0% |
| 2nd layer | Titanium dioxide | qsp 100% |
| | Lecithin | 0.1% |
| | Corn Starch Binder | 0.4% |
| 3rd Layer | C. Monarch gold | 3.0% |
| | Corn Starch Binder | 0.6% |

Percentages indicate weight percent relative to the total microcapsule weight. (3) Ingredient of each layer (in details):

| | | | | |
|---|---|---|---|---|
| Core | Organic core | 34.4% | *Zea Mays*(corn) Starch | 14.3% |
| | | | Mannitol | 10.5% |
| | | | Cellulose | 9.6% |
| 1st layer | reflective particle E | 50.0% | reflective particle | 50 |
| | Lecithin | 0.50% | Hydrogenated Lecithin | 0.50% |
| | Mannitol | 4.0% | Mannitol | 4.0% |
| | Corn Starch Binder | 2.0% | *Zea Mays*(corn) Starch | 2.0% |
| 2nd layer | Titanium dioxide | qsp. 100% | Titanium dioxide | qsp. 100% |
| | Lecithin | 0.1% | Hydrogenated Lecithin | 0.1% |
| | Corn Starch Binder | 0.4% | *Zea Mays*(corn) Starch | 0.4% |
| 3rd Layer | C. Monarch gold | 3.0% | Mica | 1.575% |
| | | | Titanium Dioxide | 1.29% |
| | | | Iron oxide Red | 0.12% |
| | | | Tin Oxide | 0.015% |
| | Corn Starch Binder | 0.6% | *Zea Mays*(corn) Starch | 0.6% |

Percentages indicate weight percent relative to the total microcapsule weight.

Example 10

By using the ingredients and contents described in the below table, a microcapsule having a core and 2 layers is prepared by the procedure provided in any of Examples 1 or example 2, especially in example 1b:

(1) Ingredients: Core seed—reflective particle layer—Outer color layer

| | | |
|---|---|---|
| Core | Mannitol | 27.85% |
| $1^{st}$ layer | reflective particle I | qsp. 100% |
| | Lecithin | 0.5% |
| | Corn Starch Binder | 1.5% |
| $2^{nd}$ layer | D&C Red30 | 0.145% |
| | Satin White | 4.55% |
| | Corn Starch Binder | 0.3% |

Percentages indicate weight percent relative to the total microcapsule weight.

(2) Ingredient of each layer (in details):

| | | | | |
|---|---|---|---|---|
| Core | Mannitol | 27.85% | Mannitol | 27.85% |
| $1^{st}$ layer | reflective particle B | qsp. | reflective particle | qsp. 100% |
| | Lecithin | 0.5% | Lecithin | 0.5% |
| | Corn Starch Binder | 1.5% | Corn Starch Binder | 1.5% |
| $2^{nd}$ layer | D&C Red30 | 0.145% | D&C Red30 | 0.145% |
| | Satin White | 4.55% | Synthetic Fluorphlogopite | 2.66% |
| | Sunshine Fine White | | Tin oxide | 0.023% |
| | | | Titanium Dioxide | 1.867% |
| | Corn Starch Binder | 0.3% | Corn Starch Binder | 0.3% |

Percentages indicate weight percent relative to the total microcapsule weight.

Example 11

By using the ingredients and contents described in the below table, a microcapsule having a core and 3 layers is prepared by the procedure provided in any of Examples 1 or example 2, especially in example 1b:

(1) reflective particle E (2) Ingredients: Core seed—reflective particle inner layer—TiO2 particle layer—Outmost shell

| | | | | |
|---|---|---|---|---|
| Core | Organic core | 4.0% | Cellulose | 1.0% |
| | | | Mannitol | 1.0% |
| | | | *Zea Mays*(corn) Starch | 2.0% |
| $1^{st}$ layer | reflective particle E | 50.0% | reflective particle | 50% |
| | Lecithin | 0.50% | Hydrogenated Lecithin | 0.50% |
| | Mannitol | 3.5% | Mannitol | 3.5% |
| | Corn Starch Binder | 2.0% | *Zea Mays*(corn) Starch | 2.0% |
| $2^{nd}$ layer | Titanium dioxide | qsp. 100% | Titanium dioxide | qsp. 100% |
| | Corn Starch | 2.0% | *Zea Mays*(corn) Starch | 2.0% |
| | Cellulose | 5.0% | Cellulose | 5.0% |
| | Mannitol | 6.5% | Mannitol | 6.5% |
| | Lecithin | 0.25% | Hydrogenated Lecithin | 0.25% |
| | Corn Starch Binder | 1.0% | *Zea Mays*(corn) Starch | 1.0% |
| $3^{rd}$ Layer | Iron oxide Red | 0.05% | Iron oxide Red | 0.05% |
| | Iron oxide Yellow | 0.01% | Iron oxide Yellow | 0.01% |
| | Cellulose | 5.0% | Cellulose | 5.0% |
| | Mannitol | 6.5% | Mannitol | 6.5% |
| | Corn Starch | 7.44% | *Zea Mays*(corn) Starch | 7.44% |
| | Lecithin | 0.25% | Hydrogenated Lecithin | 0.25% |
| | Corn Starch Binder | 1.0% | *Zea Mays*(corn) Starch | 1.0% |

Percentages indicate weight percent relative to the total microcapsule weight.

Example 12

By using the ingredients and contents described in the below table, a microcapsule, as shown in FIG. 1, having a core including notably mannitol and reflective particle, for instance B, is prepared by the procedure provided in any of Examples 1 or example 2, especially in example 1b:

| | | | | |
|---|---|---|---|---|
| Core | Lecithin | 0.9% | Hydrogenated Lecithin | 0.9% |
| | Mannitol | 18.9% | Mannitol | 18.9% |
| | Corn Starch Binder | 4.5% | *Zea Mays*(corn) Starch | 4.5% |
| | Reflective particle B | 75.6% | Reflective particle B | 75.6% |
| $1^{st}$ layer | Reflective particle B | 60.0% | Reflective particle B | 60.0 |
| | Lecithin | 0.04% | Hydrogenated Lecithin | 0.040% |
| | Mannitol | 15.0% | Mannitol | 15.0% |
| | Corn Starch Binder | 0.20% | *Zea Mays*(corn) Starch | 0.20% |
| $2^{nd}$ layer | Lecithin | 0.01% | Hydrogenated Lecithin | 0.01% |
| | Corn Starch Binder | 0.025% | *Zea Mays*(corn) Starch | 0.025% |

Example 13

To a mixed solution of methylene chloride and ethanol (weight ratio=1:1), hydrogenated lecithin and corn starch are added and completely dissolved at 40° C. To the resulting reaction mixture, Reflective particle B is added and well dispersed with a homogenizer to prepare a core.

The same ingredients are prepared and introduced into a fluidized bed coating system (Glatt GPOG 1) for coating the core with an inner coating solution to obtain a core particle coated with an inner layer. In this example the core as well as the first layer includes at least one particle having a high wet point which is dispersed.

Thereafter, to a mixed solution of methylene chloride and ethanol (weight ration=1:1), hydrogenated lecithin, PMMA (Polymethyl methacrylate) and corn starch binder are added and dissolved at 40° C. To the resulting reaction mixture, particular titanium dioxide is added and well dispersed with a homogenizer to prepare a titanium dioxide particle coating solution.

A coating of the core particle coated with an inner layer with the resulting titanium dioxide particle coating solution is carried out by a fluidized bed process to obtain particles having a core—an inner layer—titanium dioxide particle layer, each of the core and the inner layer including a Reflective particle B.

According to the above procedure, a microcapsule having 3 layers is obtained by using ingredients and contents in the below table:

| | | |
|---|---|---|
| Core | Reflective particle B | 40.0% |
| | Lecithin | 0.4 |
| | Corn Starch binder | 4 |
| Inner Layer | Reflective particle B | 30.0% |
| | Lecithin | 0.4% |
| | Corn Starch binder | 3.0% |
| Shell (TiO2 particles layer) | Titanium dioxide | 20.0% |
| | Lecithin | 1.2% |
| | PMMA | 0.7% |
| | Corn Starch binder | 0.3% |

II Compositions

In all examples, <<alcohol>> means <<ethanol>>.

When not specified, the protocol used to prepare the compositions is a conventional protocol.

Example 1: Foundation

| Chemical names | % weight |
|---|---|
| Magnesium Sulfate, 7 H2O | 0.70 |
| Modified Hectorite distearyl dimethyl ammonium | 0.80 |

| Chemical names | % weight |
|---|---|
| Talc: micronized magnesium silicate (particle size: 5 microns) (ci: 77718) | 0.50 |
| Microcapsules of example 1 | 2.00 |
| Ash gray microcapsule containing mannitol, iron oxide red, iron oxide yellow, iron oxide black, hydrogenated lecithin, titanium dioxide, zea mays (corn) starch (Magic 50-BW0105 ® from KPT) | 2.00 |
| Refined plant Perhydrosqualene | 1.00 |
| Protected 2-ethyl hexyle 4-methoxycinnamate | 3.00 |
| Bismuth oxychloride and ethylhexyl hydroxystearate (Timiron liquid silver ® from merck) | 3.00 |
| Microspheres of nylon-12 (particle size: 5 microns) | 0.50 |
| Phenyl trimethylsiloxy trisiloxane (viscosity: 20 cst-pm: 372) | 2.00 |
| Poly dimethylsiloxane with alpha-omega oxyethylene/oxypropylene groups in solution in cyclopentasiloxane | 1.00 |
| Poly dimethylsiloxane oxyethylene (dp: 70-viscosity: 500 cst) | 2.00 |
| Polydimethylsiloxane 2 cst | 27.98 |
| 1,3-butylene glycol | 3.00 |
| Denatured Ethyl Alcohol 96 degrees | 5.00 |
| Hydrophilic gelifying agent | 1.00 |
| Water | qsp 100 |

Protocol of Preparation

Aqueous phase (water, butylene glycol, magnesium sulfate) and fatty phase (silicone surfactants, oils, fillers) are prepared separately.

Both phases are then mixed under Moritz agitation until homogenization.

Then the bismuth oxychloride dispersed in ethylhexylhydroxystearate is added under Moritz agitation until homogenization.

Then the alcohol is added under Moritz agitation.

The microcapsules are then added under low Rayneri agitation until homogenization.

Observations

The composition in the jar or on finger has a white pearly aspect, the microcapsules being covered by the bismuth oxychloride pre-dispersion. The composition is stable for a long time in storing conditions and do exhibit a good dispersion of the particles.

After application and homogenization on the skin, the said composition gives a unifying and luminous make-up effect.

Example 2: Transparent Gel with Microcapsules Care of the Skin

| Phase | INCI name | % weight |
|---|---|---|
| A1 | WATER | qsp 100 |
|  | ACRYLATES/C10-30 ALKYL ACRYLATE CROSSPOLYMER (CARBOPOL ULTREZ 20 POLYMER ® from LUBRIZOL) | 0.70 |
| A2 | GLYCERIN | 4.00 |
|  | DISODIUM EDTA | 0.15 |
|  | BUTYLENE GLYCOL | 6.00 |
|  | CAPRYLYL GLYCOL | 0.25 |
| B | WATER | 31.00 |
|  | BIS-PEG-18 METHYL ETHER DIMETHYL SILANE (DOW CORNING 2501 COSMETIC WAX ® from Dow Coming) | 2.00 |
| C | WATER | 3.00 |
|  | Sodium hydroxide | qs |
| D1 | BIOSACCHARIDE GUM-1 | 1.00 |
|  | PEG/PPG/POLYBUTYLENE GLYCOL-8/5/3 GLYCERIN (WILBRIDE S-753L ® from Nof Corporation) | 0.70 |
| D2 | ALCOHOL | 4.00 |
| E | MICROCAPSULE OF EXAMPLE 3 | 2 |

Protocol of Preparation:

Premix B at 70° C., mix until solution is clear

Main Mix

1. Phase A1 make the polymer well swelled in water, then, heat to 80° C.-85° C.
2. Add A2, mix until fully dissolved
3. Add phase B, fully dissolved, then cool to RT
4. Below 40° C., add in phase C.
5. Vacuum and slow mix, to reduce the gas bubbles in the bulk
6. Add phase D1, D2
7. Vacuum and slow mix, until temp to RT, and with few gas bubbles
8. Slowly add phase E (microcapsules), mix without scraper.
9. When microcapsules are fully dispersed evenly, stop mixing, check the pH and viscosity The viscosity of the gel is around 20 UD (Mobile 3) by Rheomat RM180, at 25° C. according to the protocol disclosed above and is preserved for a long time in storing conditions.

Aspect of the Composition and Evaluation after Application

The gel presents a transparent and caring appearance We obtain a gel with microcapsules in pure and clean appearance, with perfect stability under −20/20° C. (5 cycle), room temperature (25° C., 2 months), 37° C. (2 months) and 45° C. (2 months). The microcapsules release the reflective particles during application on the skin with comfortable feeling during application, and confer natural make-up result as it was a foundation, but with a very good balance of skincare efficacy perception (watery, moisturization and transparent) as well as a proper coverage.

Example 3: O/W Emulsion with Microcapsules

| Phase | INCI name | % weight |
|---|---|---|
| A1 | GLYCERIN | 8.00 |
|  | WATER | qsp 100 |
|  | PRESERVATIVES | 0.50 |
|  | PROPYLENE GLYCOL | 8.00 |
| A2 | POTASSIUM CETYL PHOSPHATE | 1.00 |
| B1 | STEARIC ACID | 2.00 |
|  | GLYCERYL STEARATE (and) PEG-100 STEARATE | 1.50 |
|  | CETYL ALCOHOL | 0.70 |
|  | OCTYLDODECANOL | 4.00 |
|  | ETHYLHEXYL METHOXYCINNAMATE | 9.50 |
| B2 | TRIETHANOLAMINE | 0.40 |
|  | PHENOXYETHANOL | 0.70 |
| B3 | CYCLOHEXASILOXANE | 4.00 |
| B4 | TITANIUM DIOXIDE (and) C9-15 FLUOROALCOHOL PHOSPHATE (and) ALUMINUM HYDROXIDE | 2.00 |
| C | CYCLOHEXASILOXANE | 3.00 |
|  | CARBOMER | 0.30 |
|  | XANTHAN GUM | 0.10 |
| D | WATER | 1.00 |
|  | TRIETHANOLAMINE | 0.30 |
| E | TALC | 0.50 |

-continued

| Phase | INCI name | % weight |
|---|---|---|
| F | MICROCAPSULES OF EXAMPLE 12 | 1.00 |
| | BISMUTH OXYCHLORIDE | 5.00 |

Protocol of Preparation:

1. mixing phase A1 to 75° C.
2. add A2 into A1
3. B3+B4 roll miller
4. Mixing B1+B2+B3+B4 to 75° C.
5. Add Phase B into phase A, homogenize (Rayneri 1000 rpm, 10 min)
6. Cool down to 65° C. add phase C, phase D (1800 rpm, 15 min)
7. Cool down to 45° C. add Phase E
8. Change Rayneri to Ekart, using a small blender, add phase F until the microcapsules are even dispersed.

Aspect of the Composition and Evaluation after Application

The O/W emulsion has a pure and clean appearance in the jar, with perfect stability under −20/20° C. (5 cycle), room temperature (25° C., 2 months), 37° C. (2 months) and 45° C. (2 months). The microcapsules release reflective particles during application on the skin with comfortable feeling during application, and confer natural make-up result as it was a foundation, but with a very good balance of skincare efficacy perception (watery, moisturization and transparent).

Example 4: Skin Care Gel

| INCI name | % weight |
|---|---|
| WATER | Qsp 100 |
| GLYCERIN | 4 |
| DISODIUM EDTA | 0.15 |
| NIACINAMIDE | 4 |
| BUTYLENE GLYCOL | 7 |
| CHLORPHENESIN | 0.25 |
| ACRYLATES/C10-30 ALKYL ACRYLATE CROSSPOLYMER (CARBOPOL ULTREZ 20 POLYMER ® from LUBRIZOL) | 0.7 |
| BIS-PEG-18 METHYL ETHER DIMETHYL SILANE | 2 |
| PEG-60 HYDROGENATED CASTOR OIL | 0.1 |
| BIOSACCHARIDE GUM-1 | 1 |
| SODIUM HYDROXIDE | 0.24 |
| ALCOHOL | 5 |
| CAPRYLOYL SALICYLIC ACID | 0.15 |
| MICROCAPSULES OF EXAMPLE 5 | 0.5 |
| TITANIUM DIOXIDE (and) IRON OXIDES (and) MANNITOL (and) IRON OXIDES (and) *ZEA MAYS* (CORN) STARCH (and) IRON OXIDES (and) HYDROGENATED LECITHIN (M.agic50-BW0105 ® from KPT) | 0.2 |

The gel is prepared as the one disclosed in example 2.

After application on the skin, natural make-up result is obtained with a good balance of skincare efficacy perception (watery, moisturization and transparent) as well as makeup efficacy (proper coverage).

Example 5: Gelly Skin Care Cream

| INCI NAME | % weight |
|---|---|
| WATER | Qsp 100 |
| GLYCEROL | 4 |
| 1,3-BUTYLENE GLYCOL | 8 |
| VITAMINE B3 OR PP: NICOTINIC ACID AMIDE | 4 |
| ETHYLENE DIAMINE TETRACETIC ACID, DISODIUM SALT, 2 H2O | 0.1 |
| CARBOXYVINYLIC POLYMER SYNTHETIZED IN METHYLENE CHLORIDE | 0.6 |
| POLY DIMETHYLSILOXANE (VISCOSITY: 10 CST) | 1 |
| MIXTURE OF RETICULATED POLY DIMETHYLSILOXANE POLYALKYLENE AND POLY DIMETHYLSILOXANE (6 CST) 27/73 | 0.8 |
| MIXTURE OF POLY DIHYDROXYLATED DIMETHYLSILOXANE ALPHA-OMEGA/POLY DIMETHYLSILOXANE 5 CST | 1.2 |
| n-OCTANOYL-5 SALICYLIC ACID | 0.15 |
| NO DENATURATED ABSOLUTE ETHYL ALCOHOL | 5 |
| MICROCAPSULES OF EXAMPLE 6 | 0.5 |

This composition is obtained according to classical method. After application on the skin, a healthy effect is obtained with a good balance of skincare efficacy perception (watery, moisturization and transparent) as well as makeup natural effect.

Example 6: Emulsion (O/W) for Eyes

| INCI name | % weight |
|---|---|
| DISODIUM EDTA | 0.1 |
| MICROCAPSULES OF EXAMPLE 7 | 2 |
| PHENOXYETHANOL | 0.8 |
| CAPRYLIC/CAPRIC TRIGLYCERIDE | 1.26 |
| TITANIUM DIOXIDE (and) MICA (and) SILICA (TIMIRON SPLENDID COPPER ® FROM Merck) | 0.7 |
| PTFE (POLYTETRAFLUOROETHYLENE) | 1.5 |
| AMMONIUM POLYACRYLOYLDIMETHYL TAURATE | 1 |
| PEG-12 DIMETHICONE | 0.6 |
| DIMETHICONE (and) DIMETHICONOL (XIAMETER PMX-1503 FLUID ® from Dow Corning) | 2.5 |
| POLYMETHYLSILSESQUIOXANE (Tospearl 200B ® from Momentive Performance Materials) | 1.5 |
| POLYSILICONE-11 (GRANSIL RPS-D6 ® from Grant Industries) | 21 |
| ETHANOL | 4 |
| WATER | Qsp 100 |
| GLYCERIN | 8 |

This O/W emulsion is obtained according to classical method.

The cream is applied around the eye and confers a natural skin and make-up effect that diminishes the visibility of dark circles. The particles are homogeneously dispersed.

Example 7: Aerosol Foams

| INCI Name | A | B | C | D | E |
|---|---|---|---|---|---|
| TITANIUM DIOXIDE (and) SILICA (and) ALUMINUM HYDROXIDE (and) ALGINIC ACID | 5.6 | 5.6 | 5.6 | 3.8 | 5.6 |

-continued

| INCI Name | A | B | C | D | E |
|---|---|---|---|---|---|
| TALC | 2.2 | 2.2 | 2.2 | 9.50 | 2.20 |
| SILICA (and) METHICONE | 3.00 | 3.00 | 3.00 | 0.00 | 3.00 |
| CALCIUM CARBONATE | 2.00 | 2.00 | 2.00 | 0.00 | 2.00 |
| ETHYLHEXYL METHOXY-CINNAMATE | 7.50 | 7.50 | 7.50 | 7.50 | 7.50 |
| WATER | qsp 95 | qsp 95 | qsp 95 | qsp 95 | qsp 95 |
| HYDROPHILIC GELIFYING AGENT | 1.00 | 1.00 | 1.00 | 1.00 | 1.00 |
| DIPOTASSIUM GLYCYRRHIZATE | 0.20 | 0.20 | 0.20 | 0.20 | 0.20 |
| SODIUM HYALURONATE | 0.01 | 0.01 | 0.01 | 0.01 | 0.01 |
| BETAINE | 1.00 | 1.00 | 1.00 | 1.00 | 1.00 |
| GLYCERIN | 2.00 | 2.00 | 2.00 | 2.00 | 2.00 |
| ETHYLHEXYL-GLYCERIN | 0.20 | 0.20 | 0.20 | 0.20 | 0.20 |
| CAPRYLYL GLYCOL | 0.50 | 0.50 | 0.50 | 0.50 | 0.50 |
| BUTYLENE GLYCOL | 2.00 | 2.00 | 2.00 | 2.00 | 2.00 |
| ALCOHOL | 2.85 | 2.85 | 2.85 | 2.85 | 2.85 |
| PEG-12 DIMETHICONE | 0.95 | 0.95 | 0.95 | 0.95 | 0.95 |
| PHENOXY-ETHANOL | 0.285 | 0.285 | 0.285 | 0.285 | 0.285 |
| MICROCAPSULES OF EXAMPLE 1 | 3.80 | 8.55 | 13.30 | 3.80 | 20.00 |
| LPG (LIQUIFIED PETROLEUM GAS) | 5.00 | 5.00 | 5.00 | 5.00 | 5.00 |

a) Procedure of Preparation

1. Powder phase is mixed by powder mixer
2. Mixed powder phase is added in main kettle
3. Heated water phase (75-85° C.) is added in main kettle
4. Heated oil phase (75-85° C.) is added in main kettle
5. Homogenized in main kettle
6. After mixing, cooled by room temperature
7. Added surfactant and fragrance phase in main kettle
8. Homogenized in main kettle
9. Add the microcapsules and mix gently with paddle
10. Finish to make bulk (Filling Process)

11. Pour bulk in the aerosol package
12. Add LPG (propane/butane mixture (Liquified Petroleum Gas or LPG) in aerosol package (5%, 0.31 MPa)

With A-D compositions, the foams obtained are white, with composition E, a foam is obtained, the capsules are quite invisible in the bulk.

They all confer a natural skin and make-up effect when applied on the skin.

The invention claimed is:

1. A composition comprising, in a physiologically acceptable medium, a microcapsule comprising a core, a layered coating surrounding the core, and a reflective particle, wherein said layered coating comprising at least one inner layer surrounding the core and including the reflective particle, and one outer layer, wherein the reflective particle only is released from the microcapsule when the composition is applied onto a keratin material, wherein the microcapsule comprises from 5% to 80% by weight of the reflective particle relative to the weight of the microcapsule.

2. The composition according to claim 1, wherein the reflective particle is in the form of flakes having a ratio die greater than 10.

3. The composition according to claim 1, wherein the reflective particle is present in the core of the microcapsule.

4. The composition according to claim 1, wherein the core of the microparticle comprises the reflective particle and a binder.

5. The composition according to claim 1, wherein the reflective particle is present in the core of the microcapsule and in at least one inner layer.

6. The composition according to claim 1, wherein the microcapsule comprises a layer comprising a binder.

7. The composition according to claim 1, wherein the outer layer does not comprise the reflective particle.

8. The composition according to claim 1, wherein the core comprises the reflective particle and optionally an organic material, the layered coating comprises at least one binder selected from the group consisting of a polymer and a lipid-based material, and optionally a reflective particle which may be the same or different from the reflective particle contained in the core, and the layered coating comprises an outer layer comprising a hydrophilic polymer.

9. The composition according to claim 1, wherein the core comprises an organic material, the layered coating comprises at least one binder selected from the group consisting of a polymer and a lipid-based material, and at least one reflective particle, and the layered coating comprises an outer layer comprising a hydrophilic polymer.

10. The composition according to claim 9, wherein the organic material is a monosaccharide or a derivative of a monosaccharide.

11. The composition according to claim 1, wherein the layered coating surrounding the core comprises at least one hydrophilic polymer selected from the group consisting of:

acrylic or methacrylic acid homopolymers or copolymers or salts and esters thereof;

copolymers of acrylic acid and of acrylamide and its salts and esters thereof;

polyhydroxycarboxylic acids and its salts and esters thereof;

polyacrylic acid/alkyl acrylate copolymers;

AMPS;

AMPS; acrylamide copolymers;

polyoxyethylenated AMPS/alkyl methacrylate copolymers;

anionic, cationic, amphoteric or nonionic chitin or chitosan polymers;

cellulose polymers and derivatives;

Starch polymers and derivatives, eventually modified;

vinyl polymers and derivatives;

polymers of natural origins and derivatives thereof;

alginates and carrageenans;

glycoaminoglycans, hyaluronic acid and derivatives thereof; and mucopolysaccharides.

12. The composition according to claim 1, wherein the layered coating comprises at least one hydrophilic polymer selected from the group consisting of polysaccharides and derivatives, and acrylic or methacrylic acid homopolymers or copolymers or salts and esters thereof.

13. The composition according to claim 1, wherein the layered coating comprises at least one hydrophilic polymer selected from the group consisting of starch or derivatives, and celluloses or derivatives.

14. The composition according to claim 1, wherein the core comprises a monosaccharide polyol, and the coating comprises a polysaccharide or polysaccharide derivative comprising a D-Glucose unit.

15. The composition according to claim 1, wherein the microcapsule further comprises a lipid based material.

16. The composition according to claim 1, wherein the microcapsule comprises:

the core comprising the reflective particle and/or a monosaccharide-polyol, at least two different layers, a hydrophilic polymer, and optionally a lipid based material.

17. The composition according to claim 1, wherein:

the core comprises the reflective particle, a monosaccharide-polyol, a lipid based material and a hydrophilic polymer, the layered coating comprises an inner layer comprising starch as a binder, a polymer selected from the group consisting of alkylacrylic/alkylmethacrylic acid copolymers and their derivatives, a lipid based material, a plasticizer, microcrystalline cellulose, hydroxypropylcellulose and optionally a reflective particle which may be the same or different from the reflective particle contained in the core, and the layered coating comprises an outer layer comprising $TiO_2$, a polymer and optionally a binder.

18. The composition according to claim 1, wherein:

the core comprises the reflective particle, a monosaccharide-polyol, a lipid based material and a hydrophilic polymer, the layered coating comprises an inner layer comprising a reflective particle, which may be the same or different from the reflective particle contained in the core, a monosaccharide-polyol, and a lipid based material, and the layered coating comprises an outer layer comprising a lipid based material and a hydrophilic polymer.

19. The composition according to claim 1, wherein at least one layer is obtained by a fluid bed process.

20. The composition according to claim 1, wherein the reflective particle is at least one selected from the group consisting of flake particles having at least two parallel faces that consist of a single material which is optically uniform;

multilayer interference pigments; and diffractive pigments.

21. The composition according to claim 20, comprising at least one multilayer interference pigment selected from the group consisting of nacres, reflective interference particles, and goniochromatic pigments.

22. The composition according to claim 1, wherein the reflective particle is an inorganic particle coated with a metallic (poly)oxide(s).

* * * * *

UNITED STATES PATENT AND TRADEMARK OFFICE

CERTIFICATE OF CORRECTION

PATENT NO. : 10,617,609 B2
APPLICATION NO. : 15/306931
DATED : April 14, 2020
INVENTOR(S) : Momoko Shimizu et al.

It is certified that error appears in the above-identified patent and that said Letters Patent is hereby corrected as shown below:

In the Claims

Column 79, Line 64, Claim 2, “ratio die” should read -- ratio d/e --.

Column 80, Line 42, Claim 11, “AMPS; acrylamide” should read -- AMPS/acrylamide --.

Column 80, Line 52, Claim 11, “glycoaminoglycans,” should read -- glycosaminoglycans, --.

Signed and Sealed this
Twenty-eighth Day of July, 2020

Andrei Iancu
*Director of the United States Patent and Trademark Office*